US011725026B2

(12) United States Patent
Mollapour et al.

(10) Patent No.: US 11,725,026 B2
(45) Date of Patent: Aug. 15, 2023

(54) COMPOSITIONS AND METHODS FOR INHIBITING LACTATE DEHYDROGENASE A ACTIVITY

(71) Applicant: Research Foundation for SUNY, Albany, NY (US)

(72) Inventors: Mehdi Mollapour, Fayetteville, NY (US); Gennady Bratslavsky, Fayetteville, NY (US); Mark R. Woodford, Baldwinsville, NY (US); Dimitra Bourboulia, Fayetteville, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 222 days.

(21) Appl. No.: 16/915,966

(22) Filed: Jun. 29, 2020

(65) Prior Publication Data

US 2020/0407397 A1 Dec. 31, 2020

Related U.S. Application Data

(60) Provisional application No. 62/867,978, filed on Jun. 28, 2019.

(51) Int. Cl.
| | |
|---|---|
| *C07K 7/06* | (2006.01) |
| *C07K 7/08* | (2006.01) |
| *A61K 47/60* | (2017.01) |
| *C07K 7/64* | (2006.01) |
| *A61K 38/00* | (2006.01) |

(52) U.S. Cl.
CPC ............... *C07K 7/06* (2013.01); *A61K 47/60* (2017.08); *C07K 7/08* (2013.01); *C07K 7/64* (2013.01); *A61K 38/00* (2013.01)

(58) Field of Classification Search
CPC ... C07K 7/06; C07K 7/08; C07K 7/64; A61K 47/60; A61K 38/00; C12N 9/0006
See application file for complete search history.

(56) References Cited

U.S. PATENT DOCUMENTS

| 11,247,971 B2* | 2/2022 | Maloney | ............... C07D 495/14 |
| 2005/0170357 A1* | 8/2005 | Schmidt | ............... C12N 15/113 |
| | | | 435/6.12 |

FOREIGN PATENT DOCUMENTS

WO WO2006135762 * 12/2006 ............. C07K 14/47

OTHER PUBLICATIONS

Lingaas et al. A mutation in the canine BHD gene is associated with hereditary multifocal renal cystadenocarcinma and nodular dermatofibrosis in the German Shepherd dog. Human Molecular Genetics, 2003, vol. 12, No. 23, pp. 3043-3053. (Year: 2003).*
Roberts et al. Chemistry for peptide and protein PEGylation. Advanced Drug Delivery Reviews, vol. 54, pp. 459-476. (Year: 2002).*
Warburg, O. The Metabolism of Carcinoma Cells. The Journal of Cancer Research 9, 1925, 148.
Vander Heiden, et al., Understanding the Intersections between Metabolism and Cancer Biology. Cell 168, 2017, 657-669.
Dawson, D. M., et al., Lactic Dehydrogenases: Functions of the Two Types. Science 143, 929, 1964.
Hathaway, G. et al., Substrate-dependent association of lactic dehydrogenase subunits to active tetramer. Proc Natl Acad Sci U S A 56, 1966, 680-685.
Preston, R. S. et al. Absence of the Birt-Hogg-Dube gene product is associated with increased hypoxia-inducible factor transcriptional activity and a loss of metabolic flexibility. Oncogene 30, 2011, 1159-1173.
Schmidt, L. S. Birt-Hogg-Dube syndrome: from gene discovery to molecularly targeted therapies. Fam Cancer 12, 2013, 357-364.
Tsun, Z. Y. et al. The folliculin tumor suppressor is a GAP for the RagC/D GTPases that signal amino acid levels to mTORC1. Mol Cell 52, 2013, 495-505.
Petit, C. S., et al., Recruitment of folliculin to 235 lysosomes supports the amino acid-dependent activation of Rag GTPases J Cell Biol 202, 2013, 1107-1122.
Fan, J. et al. Tyrosine phosphorylation of lactate dehydrogenase A is important for NADH/NAD(+) redox homeostasis in cancer cells Mol Cell Biol 31, 2011, 4938-4950.
Jin, L. et al. Phosphorylation-mediated activation of LDHA promotes cancer cell invasion and tumour metastasis. Oncogene 36, 2017, 3797-3806.
Read, J. A., et al., Structural Basis for Altered Activity of M- and H-Isoenzyme Forms of Human Lactate Dehydrogenase. Proteins: Structure, Function, and Genetics 43, 2001, 175-185.
Yamamoto, S., et al., Dissociation-association of lactate dehydrogenase 246 isozymes: influences on the formation of tetramers versus dimers of M4-LDH and H4-LDH. Int J Biochem 20, 1988, 1261-1265.
Zheng, Y., et al., Effects of N-terminal deletion mutation on rabbit muscle lactate dehydrogenase. Biochemistry (Mosc) 69, 2004, 401-406.
Valvona, C. J., et al., The Regulation and Function of Lactate Dehydrogenase A: Therapeutic Potential in Brain Tumor. Brain Pathol 26, 2016, 3-17.
Tarmy, E. M. et al., Kinetics of *Escherichia coli* B D-lactate dehydrogenase and evidence for pyruvate-controlled change in conformation. J Biol Chem 243, 1968, 2587-2596.
Jiang, G. R., et al., Regulation of the IdhA gene, encoding the fermentative lactate dehydrogenase of *Escherichia coli*. Microbiology 147, 2001, 2437-2446.

(Continued)

*Primary Examiner* — Marcela M Cordero Garcia
(74) *Attorney, Agent, or Firm* — Peter Fallon; Lance Reich

(57) ABSTRACT

The present disclosure is directed to one or more engineered peptide inhibitors against the lactate dehydrogenase A (LDHA) activity in cells. The disclosure also provides compositions, and kits including the one or more peptide inhibitors, and methods of using the one or more peptide inhibitors. The peptide inhibitors and compositions can be used for treatment of conditions in which there is abnormally high LDHA activity, such as cancer or metabolic diseases, infectious diseases, mendelian disorders, inflammatory diseases, neurodegenerative and neuropathological diseases, neuropsychological disorders, obesity and eating disorders, chronic diseases and genetic diseases.

16 Claims, 41 Drawing Sheets

Specification includes a Sequence Listing.

(56) References Cited

OTHER PUBLICATIONS

Yamamoto, S. et al., Influence of glycerol on the activity and tetramer-dimer state of lactate dehydrogenase isozymes. Int J Biochem 20, 1988, 1267-1271.
Bohačova, V., et al., Interaction of lactate dehydrogenase with anthraquinone dyes: characterization of ligands for dye-ligand chromatography. Journal of Chromatography B: Biomedical Sciences and Applications 715, 1998, 273-281.
Cahn, R. D., et al., Nature and Development of Lactic Dehydrogenases: The two major types of this enzyme form molecular hybrids which change in makeup during development. Science 136, 1962, 962-969.
Shen, K. et al. Cryo-EM Structure of the Human FLCN-FNIP2-Rag-Ragulator Complex. Cell 179, 2019, 1319-1329.
Lawrence, R. E. et al. Structural mechanism of a Rag GTPase activation checkpoint by the lysosomal folliculin complex. Science 366, 2019, 971-977.
Le, A. et al. Inhibition of lactate dehydrogenase A induces oxidative stress and inhibits tumor progression. Proc Natl Acad Sci U S A 107, 2010, 2037-2042.
Schopper, S. et al. Measuring protein structural changes on a proteome-wide scale using limited proteolysis-coupled mass spectrometry. Nat Protoc 12, 2017, 2391-2410.
Woodford, M. R., et al., Structural and functional regulation of lactate dehydrogenase-A in cancer. Future Medicinal Chemistry 12, 2020, 439-455.
Clarke, A. R. et al. Site-directed mutagenesis reveals role of mobile arginine residue in lactate dehydrogenase catalysis. Nature 324, 1986, 699-702.
Nookala, R. K. et al. Crystal structure of folliculin reveals a hidDENN function in genetically inherited renal cancer. Open Biol 2, 2012.
Nickerson, M. L. et al. Mutations in a novel gene lead to kidney tumors, lung wall defects, and benign tumors of the hair follicle in patients with the Birt-Hogg-Dube syndrome 288 Cancer Cell 2, 2002, 157-164.
Yang, Y. et al. The UOK 257 cell line: a novel model for studies of the human Birt-Hogg-Dube gene pathway. Cancer Genet Cytogenet 180, 2008, 100-109.
Linehan, W. M. et al. The Metabolic Basis of Kidney Cancer. Cancer Discov 9, 2019, 1006-1021.
Unkles, S. E. et al. Physiological and biochemical characterization of AnNitA, the Aspergillus nidulans high-affinity nitrite transporter. Eukaryot Cell 10, 2011, 1724-1732.
Yamamoto, S. S., Dissociation-Association of Lactate Dehydrogenase Isozymes:Influences on the Formation of Tetramers versus Dimers of M4-LDH and H4-LDH. Int. J. Biochem. 20, 1988, 1261-1265.
Fosgerau, K. et al., Peptide therapeutics: current status and future directions. Drug Discovery Today 20, 2015, 122-128.
Cox, J. et al., MaxQuant enables high peptide identification rates, individualized p.p.b.-range mass accuracies and proteome-wide protein quantification Nat Biotechnol 26, 2008, 1367-1372.
Woodford, M. R. et al. The FNIP co-chaperones decelerate the Hsp90 chaperone cycle and enhance drug binding. Nat Commun 7, 2016.
Gay, R. J., et al., Optimum Reaction Conditions for Human Lactate Dehydrogenase Isoenzymes as They Affect Total Lactate Dehydrogenase Activity. Clinical Chemistry 14, 1968, 740-753.
Powers, J. L., et al., Lactate Dehydrogenase Kinetics and Inhibition Using a Microplate Reader. Biochemistry and Molecular Biology Education 35, 2007, 287-292.
Cer, R. Z., et al., IC50-to-Ki: a web-based tool for converting IC50 to Ki values for inhibitors of enzyme activity and ligand binding. Nucleic Acids Res 37, 2009, W441-445.

\* cited by examiner

A

B

A

Lane 2  A Q R M N T A F T P (SEQ ID NO: 10)
Lane 3  <u>N</u> Q R M N T A F T P (SEQ ID NO: 28)
Lane 4  A <u>A</u> R M N T A F T P (SEQ ID NO: 29)
Lane 5  A Q <u>A</u> M N T A F T P (SEQ ID NO: 30)
Lane 6  A Q R <u>A</u> N T A F T P (SEQ ID NO: 31)
Lane 7  A Q R M <u>A</u> T A F T P (SEQ ID NO: 32)
Lane 8  A Q R M N <u>A</u> A F T P (SEQ ID NO: 33)
Lane 9  A Q R M N T <u>N</u> F T P (SEQ ID NO: 34)
Lane 10 A Q R M N T A <u>A</u> T P (SEQ ID NO: 35)
Lane 11 A Q R M N T A F <u>A</u> P (SEQ ID NO: 36)
Lane 12 A Q R M N T A F T <u>A</u> (SEQ ID NO: 37)

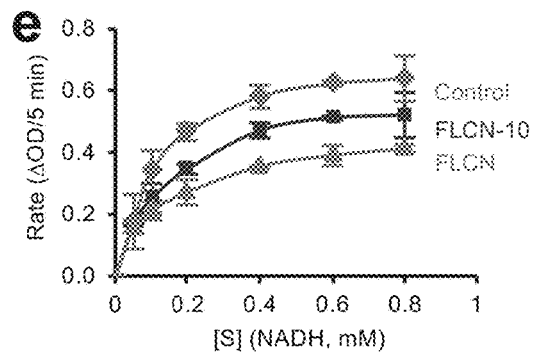
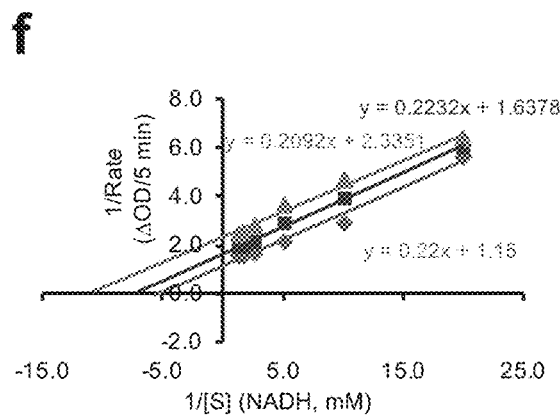
FIG. 10E - 10H

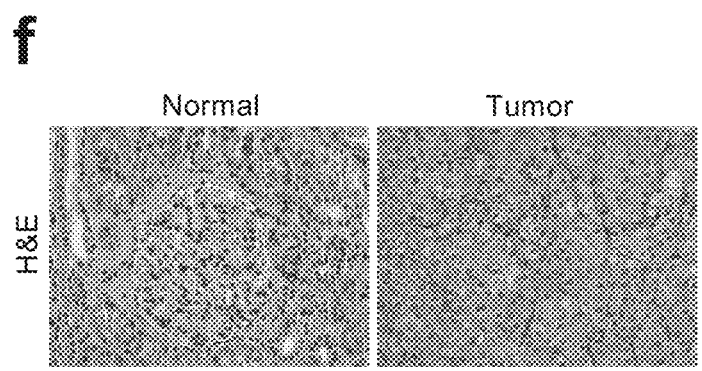
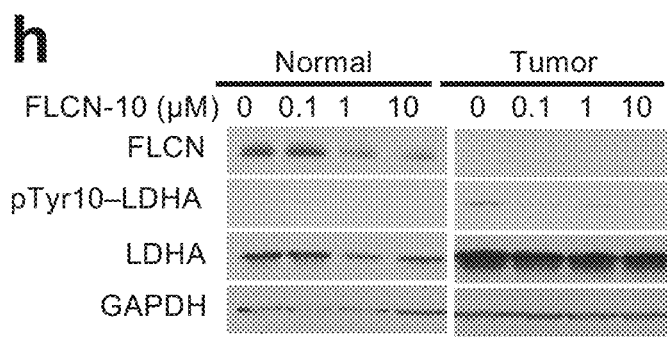
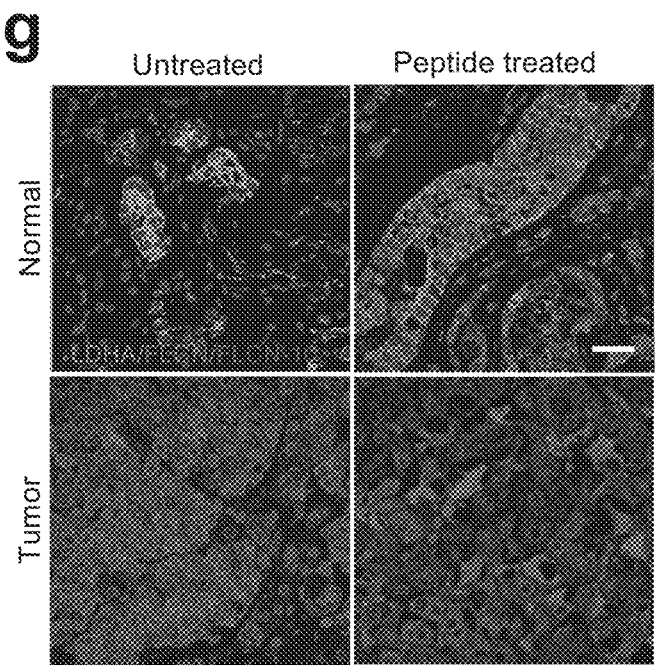
FIG. 11F - 11G a

```
LDHA  MATLKDQLIYNLLKEEQT-PQNKITVVGVGAVGMACAISILMKDLADELALVDVIEDKLK  59
LDHB  MATLKEKLIAPVAEEEATVPNNKITVVGVGQVGMACAISILGKSLADELALVDVLEDKLK  60
      ****:;**    ;:** * *;************ *********;*****

LDHA  GEMMDLQHGSLFLRTPKIVSGKDYNVTANSKLVIITAGARQQEGESRLNLVQRNVNIFKF  119
LDHB  GEMMDLQHGSLFLQTPKIVADKDYSVTANSKIVVVTAGVRQQEGESRLNLVQRNVNVFKF  120
      *************;*****.;***.******;*;;***.*****************;***

LDHA  IIPNVVKYSPNCKLLIVSNPVDILTYVAWKISGFPKNRVIGSGCNLDSARFRYLMGERLG  179
LDHB  IIPQIVKYSPDCIIIVVSNPVDILTYVTWKLSGLPKHRVIGSGCNLDSARFRYLMAEKLG  180
      ***;;*****;*  ;;;**********;**;**;**;*******************.*;**

LDHA  VHPLSCHGWVLGEHGDSSVPVWSGMNVAGVSLKTLHPDLGTDKDKEQWKEVHKQVVESAY  239
LDHB  IHPSSCHGWILGEHGDSSVAVWSGVNVAGVSLQELNPEMGTDNDSENWKEVHKMVVESAY  240
      ;** *****;*********;****;******; *;*;;***;*;**;****** *****

LDHA  EVIKLKGYTSWAIGLSVADLAESIMKNLRRVHPVSTMIKGLYGIKDDVFLSVPCILGQNG  299
LDHB  EVIKLKGYTNWAIGLSVADLIESMLKNLSRIHPVSTMVKGMYGIENEVFLSLPCILNARG  300
      *********.**********;**;;***  *;****** *;***;;;;****;****. .*

LDHA  ISDLVKVTLTSEEEARLKKSADTLWGIQKELQF-  332   (SEQ ID NO.39)
LDHB  LTSVINQKLKDDEVAQLKKSADTLWDIQKDLKDL  334   (SEQ ID NO.40)
      ;;.;;; .*,,;* *;*********.***;*;
```

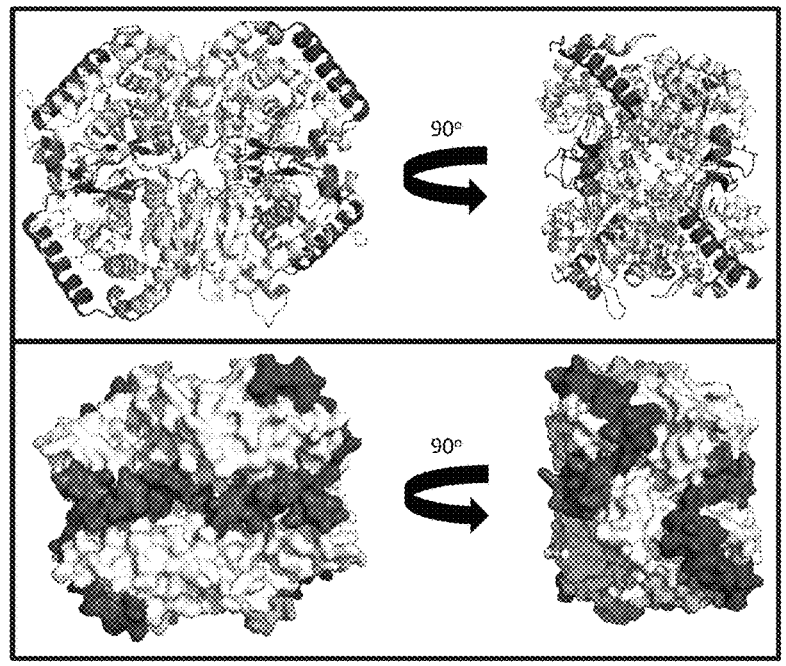

FIG. 14A - 14B e
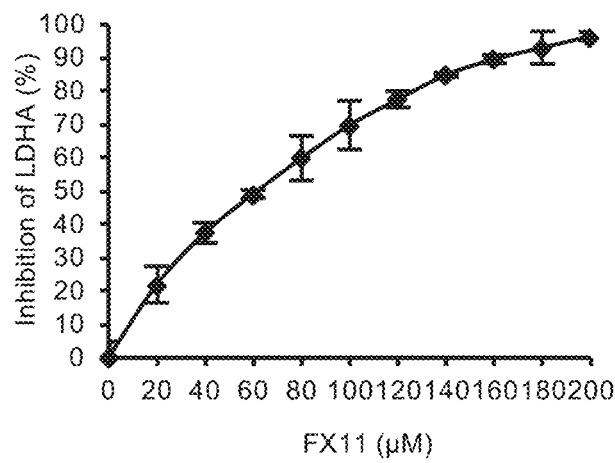
f
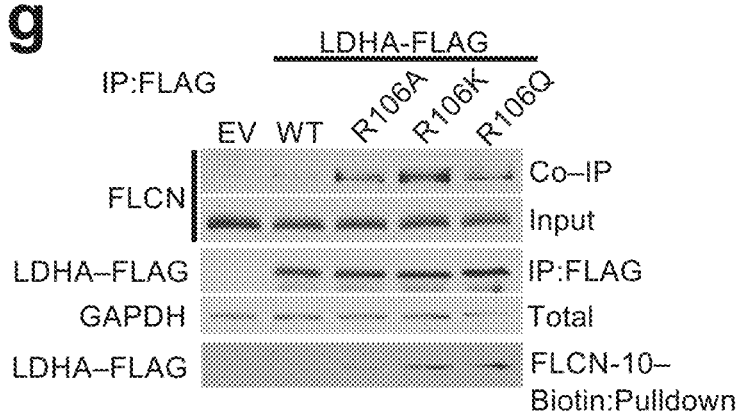
g
FIG. 17E - 17G

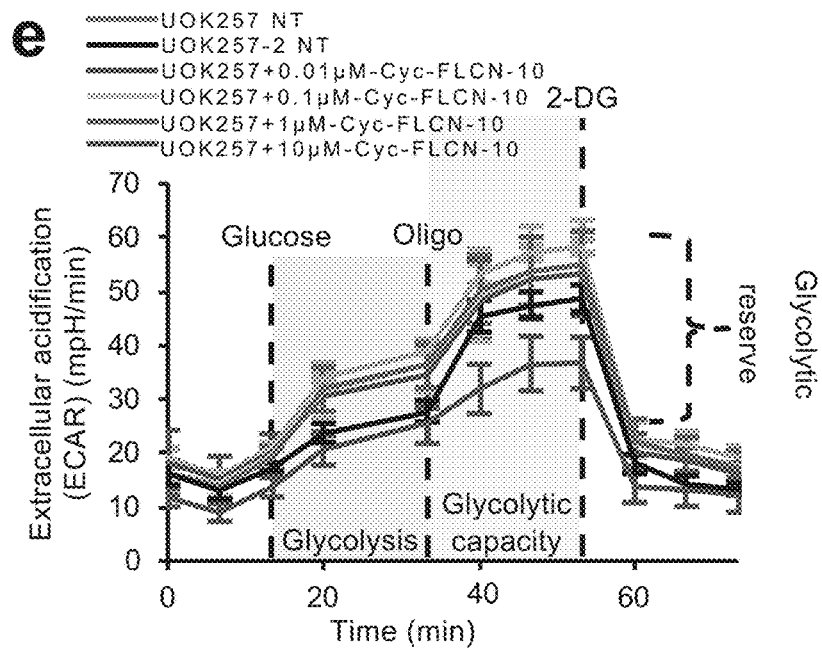
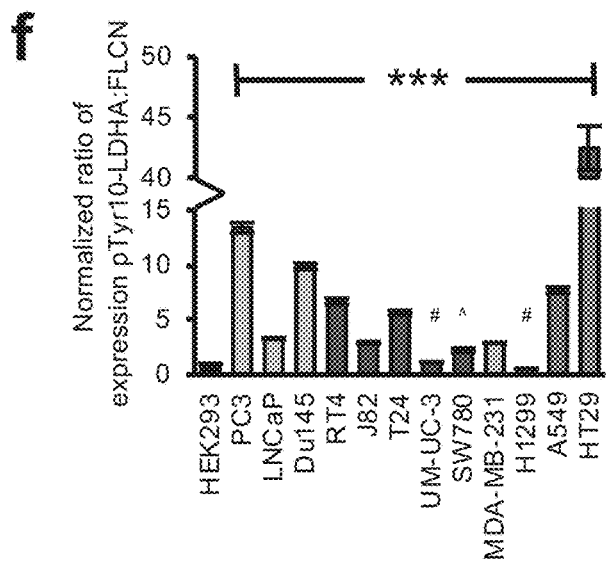
FIG. 20E - 20G
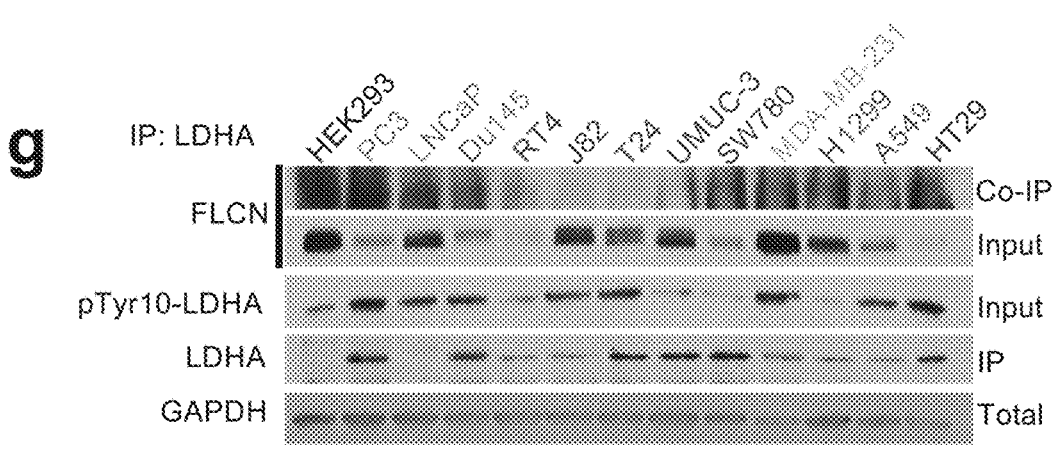

COMPOSITIONS AND METHODS FOR INHIBITING LACTATE DEHYDROGENASE A ACTIVITY

CROSS-REFERENCES TO RELATES APPLICATIONS

This application claims priority benefit to U.S. Provisional Application No. 62/867,978 filed Jun. 28, 2019, the contents of which are fully incorporated herein by reference.

REFERENCE TO A SEQUENCE LISTING

This application contains a Sequence Listing in computer readable form, which is incorporated herein by reference.

FIELD OF THE INVENTION

The present disclosure relates to compositions and methods including peptides that inhibit the activity of lactate dehydrogenase A (LDHA).

BACKGROUND

Lactate dehydrogenase A (LDHA) is a key metabolic enzyme that catalyzes the interconversion of pyruvate and lactate. LDHA is an important mediator of the "Warburg effect", a phenomenon where cancer cells preferentially utilize the glycolytic pathway to fuel cell growth and division. Increased LDHA expression and/or activity has been implicated in numerous disease processes including diabetes, Bid-Hogg-Dubé syndrome (BHDS), and cancer.

Bid-Hogg-Dubé (BHD) syndrome is a rare inherited cancer syndrome that predisposes affected individuals to develop kidney tumors, pulmonary cysts and benign skin tumors (fibrofolliculomas) (Birt A R. et al., *Archives of dermatology*. 1977; 113(12):1674-7). Germ line mutations in the tumor suppressor gene Folliculin (FLCN) lead to BHD syndrome (Nickerson M L. et al., *Cancer Cell*. 2002; 2(2):157-64; Schmidt L S. et al., *Familial Cancer*. 2013; 12(3):357-64). Surprisingly, FLCN acts as a haploinsufficient tumor suppressor in skin lesions, whereas a loss of function of both alleles is reported in the kidney tumors (van Steensel M A et al., *The Journal of investigative dermatology*. 2007; 127(3):588-93). FLCN is an evolutionarily conserved, nuclear and cytoplasmic, phosphoprotein. FLCN interacts with the co-chaperones Folliculin Interacting Proteins 1 and 2 (FNIP1 and FNIP2) in a phosphorylation-dependent manner, and together they form a complex with AMPK (Baba M et al., *PNAS*. 2006; 103(42):15552-7; Woodford M R. et al., *Nature communications*. 2016; 7:12037).

Given LDHA's important role in cell metabolism, there is a continuing need to identify agents that specifically alter the activity of LDHA, e.g. compositions and methods that reduce or inhibit the activity of LDHA in a cell.

SUMMARY

The present disclosure relates to compositions, and methods for altering the activity of LDHA. In embodiments, the present disclosure relates to a one or more peptides including a core sequence that differs from SEQ ID NO: 10 by a single amino acid substitution.

In some embodiments, the present disclosure relates to a variant peptide, comprising: an amino acid sequence having at least 70% sequence identity to SEQ ID NO: 10, wherein the amino acid sequence includes at least one alteration, and wherein the variant peptide reduces or inhibits LDHA activity in a cell.

In embodiments, the present disclosure relates to a composition including one or more peptides or one or more synthetic peptides in accordance with the present disclosure.

In embodiments, the present disclosure relates to a method of inhibiting lactate dehydrogenase A (LDHA) activity in a cell, including contacting the cell with an effective amount of one or more peptides in accordance with the present disclosure.

In embodiments, the present disclosure relates to a method of treating an individual having elevated levels of lactate dehydrogenase A (LDHA) activity including administering to the individual a therapeutically effective amount of a peptide including a core sequence that differs from SEQ ID NO: 10 by a single amino acid substitution.

In some embodiments, the present disclosure relates to a method including: (a) obtaining a biological sample from an individual; (b) measuring the level of activity of the lactate dehydrogenase A (LDHA) enzyme in the biological sample; (c) comparing the activity measured in (b) to a reference standard; (d) administering to the individual a therapeutically effective amount of a peptide including a core sequence that differs from SEQ ID NO: 10 by a single amino acid substitution if the LDHA activity in the sample is higher than the LDHA activity in the reference standard.

In embodiments, the present disclosure relates a kit including a peptide including a core sequence that differs from SEQ ID NO: 10 by a single amino acid substitution; and instructions for use.

In some embodiments the present disclosure relates to a synthetic amino acid sequence, including, or consisting of SEQ ID NOS: 1-38.

The illustrative aspects of the present disclosure are designed to solve the problems herein described and/or other problems not discussed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIG. 6E presents illustrative data relating peptides screened for $K_a$ or ability to inhibit LDHA.

FIG. 10A depicts a structure of FLCN N-terminus solved by cryo-electron microscopy (aa 2-268; PDB ID: 6nzd), wherein FIG. 10E depicts Michaelis-Menten kinetics of LDHA activity alone or in the presence of FLCN protein or FLCN-10 peptide (n=3). FIG. 10F presents illustrative data showing FLCN-10 is an uncompetitive inhibitor of LDHA based on Lineweaver-Burke plot of enzyme kinetics (n=3). FIG. 10G presents illustrative data relating to measured values for LDHA binding and kinetic data. FIG. 10H depicts structural information of dimeric LDHA, wherein individual monomers have been colored light or dark blue (PDB ID: 4okn), wherein limited proteolysis-couple MS identified LDHA catalytic loop region perturbation (red) in response to FLCN-10 peptide binding, wherein the green α-helix represents peptides unchanged by the presence of FLCN-10, wherein the LDHA catalytic R106 is highlighted in orange. Data shown as mean±s.d. Structures rendered using Chimera v1.12 (USCF).

FIG. 11F presents illustrative data relating to H+E staining of normal and tumor renal tissues from a patient with BHD. FIG. 11G illustrative data relating to illustrative data relating to fluorescence microscopy of normal and tumor renal tissues. FIG. 11H illustrative data relating to Western blots of lysates.

FIG. 14A depicts an alignment between human LDHA and human LDHB. FIG. 14B depicts structural information relating to chimeric constructs.

FIGS. 17A-G presents illustrative data relating to the present disclosure as described below.

FIGS. 18A-H presents illustrative data relating to the present disclosure as described below.

FIGS. 20A-G presents illustrative data relating to the present disclosure as described below.

DETAILED DESCRIPTION

Figures 1A, 1B, 1C:
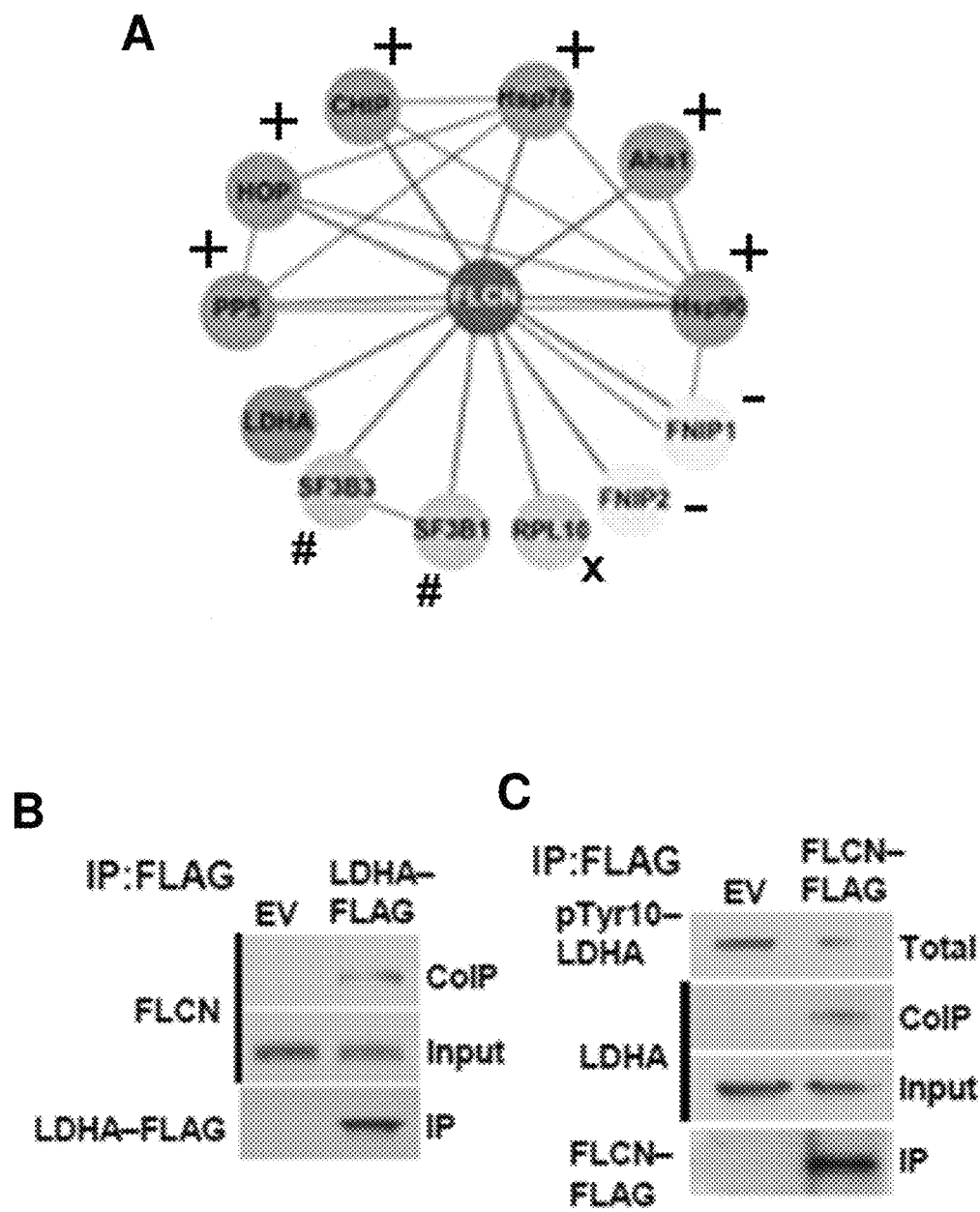
FIG. 1A presents illustrative MALDI-TOF data for FLCN-FLAG immunoprecipitated (IP) from HEK293 cells subjected to MALDI-TOF in accordance with some embodiments of the present disclosure.
FIG. 1B presents illustrative immunoblotting data for LDHA-FLAG immunoprecipitated from HEK293 cells immunoblotted for FLCN.
FIG. 1C presents illustrative immunoblotting data for FLCN-FLAG immunoprecipitated from HEK293 cells immunoblotted for LDHA.

The present disclosure relates to compositions, and methods for altering the activity of LDHA. In embodiments, the present disclosure relates to a one or more peptides including a core sequence that differs from SEQ ID NO: 10 by a single amino acid substitution. In some embodiments, the present disclosure relates to a variant peptide, including: an amino acid sequence having at least 70% sequence identity to SEQ ID NO: 10, wherein the amino acid sequence includes at least one alteration, and wherein the variant peptide reduces or inhibits LDHA activity in a cell. Advantages of the present disclosure include altering such as lowering LDHA activity in one or more cells, especially where high levels of LDHA activity is a marker of or relates to a disease. In embodiments, the compositions and methods described herein include administering a therapeutically effective amount of peptide in accordance with the present disclosure to a subject in need thereof. In embodiments, the methods of the present disclosure provide a prompt and effective treatment to reduces or inhibits LDHA activity.

Although claimed subject matter will be described in terms of certain embodiments/examples, other embodiments/examples, including embodiments/examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

All sections of this application, including any supplementary sections or figures, are fully a part of this application.

Definitions

As used in the present specification, the following words and phrases are generally intended to have the meanings as set forth below, except to the extent that the context in which they are used indicates otherwise.

As used herein, the singular forms "a", "an", and "the" include plural references unless the context clearly dictates otherwise. Thus, for example, references to "a compound" include the use of one or more compound(s). "A step" of a method means at least one step, and it could be one, two, three, four, five or even more method steps.

As used herein the terms "about," "approximately," and the like, when used in connection with a numerical variable, generally refers to the value of the variable and to all values of the variable that are within the experimental error (e.g., within the 95% confidence interval [CI 95%] for the mean) or within ±10% of the indicated value, whichever is greater.

cDNA: The term "cDNA" means a DNA molecule that can be prepared by reverse transcription from a mature, spliced, mRNA molecule obtained from a eukaryotic or prokaryotic cell. cDNA lacks introns or intron sequences that may be present in corresponding genomic DNA.

As used herein the terms "drug," "drug substance," "active pharmaceutical ingredient," and the like, refer to a compound (e.g., one or more peptides in accordance with the present disclosure) that may be used for treating a subject in need of treatment.

As used herein the term "excipient" or "adjuvant" refers to any inert substance.

As used herein the terms "drug product," "pharmaceutical dosage form," "dosage form," "final dosage form" and the like, refer to a pharmaceutical composition that is administered to a subject in need of treatment and generally may be in the form of tablets, capsules, sachets containing powder or granules, liquid solutions or suspensions, patches, and the like.

As used herein the term "fragment" means a polypeptide having one or more (e.g., several) amino acids absent from the amino and/or carboxyl terminus of a mature polypeptide or domain; wherein the fragment is able inhibit LDHA activity. In one aspect, a fragment contains at least 70% to 99%, at least 90% to 99% or about 95 to 99% of the number of amino acids of the mature polypeptide of SEQ ID NOS: 1-38.

The terms "inhibits", "inhibiting" or "inhibitor" of LDHA, as used herein, refer to inhibition of enzymatic LDHA activity.

The term "isolated" means a substance in a form or environment that does not occur in nature. Non-limiting examples of isolated substances include (1) any non-naturally occurring substance, (2) any substance such as an enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated.

As used herein, the terms "lactate dehydrogenase A" or "LDHA" or "L-lactate dehydrogenase A chain" refers to an oxidoreductase enzyme (of EC 1.1.1.27) which in humans is encoded by the LDHA gene. This enzyme is a monomer of Lactate dehydrogenase b, which exists as a tetramer.

As used herein the term "LDHA activity" may be typically reported as nmole/min/mL=milliunit/mL. One unit of LDHA activity is defined as the amount of enzyme that catalyzes the conversion of lactate into pyruvate to generate 1.0 μmole of NADH per minute at 37° C.

The term "mature polypeptide" means a polypeptide in its final form such as following translation and any post-translational modifications, if any, such as N-terminal processing, C-terminal truncation, glycosylation, etc.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) Computational Molecular Biology (Lesk, A. M., Ed.) Oxford University: NY (1988); 2) Biocomputing: Informatics and Genome Projects (Smith, D. W., Ed.) Academic: NY (1993); 3) Computer Analysis of Sequence Data, Part I (Griffin, A. M., and Griffin, H. G., Eds.) Humana: NJ (1994); 4) Sequence Analysis in Molecular Biology (von Heinje, G., Ed.) Academic (1987); and 5) Sequence Analysis Primer (Gribskov, M. and Devereux, J., Eds.) Stockton: NY (1991), all of which are incorporated herein by reference.

In embodiments, methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, CABIOS. 5: 151-153 (1989); Higgins, D. G. et al., Comput. Appl. Biosci., 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be K-TUPLE=1, GAP PENALTY=3, WINDOW=5 and DIAGONALS SAVED=5. For nucleic acids, these parameters can be K-TUPLE=2, GAP PENALTY=5, WINDOW=4 and DIAGONALS SAVED=4. Additionally, the Clustal W method of alignment can be used (described by Higgins and Sharp, CABIOS. 5:151-153 (1989); Higgins, D. G. et al., Comput. Appl. Biosci. 8:189-191 (1992); Thompson, J. D. et al, Nucleic Acids Research, 22 (22):4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

In embodiments, sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al, 2000, *Trends Genet.* 16: 276-277), preferably version 5.0.0 or later. The parameters used include gap open penalty of 10, gap extension penalty of 0.5 EBLOSUM62 (EMBOSS version of BLOSUM62) substitution matrix. In embodiments, the percent identity and is calculated as follows: (Identical Residues×100)/(Length of Alignment−Total Number of Gaps in Alignment).

As used herein the term "solvate" describes a molecular complex including the drug substance (e.g., peptide in accordance with the present disclosure) and a stoichiometric or non-stoichiometric amount of one or more pharmaceutically acceptable solvent molecules.

The term "hydrate" describes a solvate including the drug substance and a stoichiometric or non-stoichiometric amount of water.

As used herein the term "pharmaceutically acceptable" substances refers to those substances which are within the scope of sound medical judgment suitable for use in contact with the tissues of subjects without undue toxicity, irritation, allergic response, and the like, and effective for their intended use.

As used herein the term "pharmaceutical composition" refers to the combination of one or more drug substances such as e.g., one or more peptides in accordance with the present disclosure and one or more excipients and one or more pharmaceutically acceptable vehicles with which the one or more peptides in accordance with the present disclosure is administered to a subject.

As used herein, the term "pharmaceutically acceptable salt" refers to a salt of a compound, which possesses the desired pharmacological activity of the parent compound. Non-limiting examples of pharmaceutically acceptable salts include: acid addition salts, formed with inorganic acids such as hydrochloric acid, hydrobromic acid, sulfuric acid, nitric acid, phosphoric acid, and the like; or formed with organic acids; and salts formed when an acidic proton present in the parent compound is replaced by a metal ion, for example, an alkali metal ion, an alkaline earth ion, or an aluminum ion.

As used herein the term "pharmaceutically acceptable vehicle" refers to a diluent, adjuvant, excipient or carrier with which a compound is administered.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

As used herein the term "subject" includes humans, animals or mammals. The terms "subject" and "patient" may be used interchangeably herein.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "therapeutically effective amount" as used herein refers to an amount of an agent sufficient to achieve, in a single or multiple doses, the intended purpose of treatment. A "therapeutically effective amount" can vary depending, for example, on the compound, the severity of the disease, the amount of LDHA activity, the age of the subject to be treated, comorbidities of the subject to be treated, existing health conditions of the subject, and/or weight of the subject to be treated. A "therapeutically effective amount" is an amount sufficient to alter the subjects' natural state.

The term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

Variant: The term "variant" means a polypeptide including an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-10 amino acids, adjacent to the amino acid occupying a position.

CERTAIN EMBODIMENTS OF THE PRESENT DISCLOSURE

In embodiments, the present disclosure relates to one or more peptide inhibitors of LDHA. In embodiments, the one or more peptide inhibitors are synthetic such as an engineered peptide that is capable of inhibiting LDHA activity. In some embodiments, the peptide of the present disclosure preferentially inhibits the LDHA activity and displays no significant inhibition on LDHB activity. In some embodiments, the one or more peptides include a core sequence that differs from amino acids 219-228 of the folliculin (FLCN) protein shown by GenBank Accession number NP_001340159.1, incorporated by reference herein, by at least a single amino acid. SEQ ID NO: 10 represents the residues 219-228 of the wild type FLCN protein (NP_001340159.1). In some embodiments, the peptide includes a core sequence that differs from SEQ ID NO: 10 by at least a single amino acid substitution. In some embodiments, the peptide of the disclosure comprises a core sequence that differs from SEQ ID NO: 10 by at least two, at least three or at least four amino acid substitutions. In some embodiments, the peptide of the present disclosure includes a core sequence and additional amino acids in the amino- and/or carboxy-terminal of the core sequence. In some embodiments, the peptide consists of the core sequence only. In some embodiments, the present disclosure relates to a variant peptide, including: an amino acid sequence having at least 70%, at least 80%, at least 90%, at least 95% or at least 97% sequence identity to SEQ ID NO: 10, wherein the amino acid sequence includes at least one alteration, and wherein the variant peptide reduces or inhibits LDHA activity in a cell.

In embodiments, the present disclosure relates to amino acid substitutions in the core sequence and flanking the core sequence. In some embodiments, the amino acid substitutions of the peptide of the instant disclosure include conservative substitutions. In embodiments, a "conservative substitution" (also called "a conservative mutation" or "a conservative replacement") refers to an amino acid replacement in a protein that changes a given amino acid to a different amino acid with similar biochemical properties (e.g., charge, hydrophobicity and size). In embodiments, the peptides of the present disclosure may include several conservative substitutions such as 1-5 conservative substitutions. In some embodiment, the amino acid substitutions of the peptide of the instant disclosure includes non-conservative substitutions. A "non-conservative substitution" (also called "a radical replacement", or "a radical substitution," refers to an amino acid replacement that exchanges an initial amino acid by a final amino acid with different physico-chemical properties.

In some embodiments, the amino acid substitutions of the peptide of the instant disclosure include substitutions involving non-natural amino acids. In some embodiments, the non-natural amino acid substitution includes substitution of a native amino acid with a non-natural amino acid selected from the group consisting of a D-amino acid, a homo-amino acid, a beta homo amino acid, an N-methyl amino acid, and an alpha-methyl amino acid. The term "D-amino acid" refers to a non-natural amino acid that has the mirror image structure of the corresponding naturally-occurring L-isomer amino acid. The term "homo-amino acid" refers to a non-natural amino acid that has a methylene ($CH_2$) group added to the α-carbon of the amino acid. The term "beta-homo amino acid" refers to a non-natural amino acid in which the carbon skeleton has been lengthened by insertion of one carbon atom immediately after the acid group. The term "N-methyl amino acid" refers to a non-natural amino acid that carry a methyl group at the nitrogen instead of a proton. The term "alpha-methyl amino acid" refers to a non-natural amino acid in which the proton on the α-carbon atom of the natural original (in between the amino and carboxy group) has been substituted by a methyl group.

In some embodiments, the one or more peptides of the present disclosure include a core sequence that differs from SEQ ID NO: 10 by a single amino acid substitution. In some embodiments, the single amino acid substitution includes an alanine (A) residue (e.g., one of positions 1 and 7 of SEQ ID NO: 10, or positions A219 and A225 of NP_001340159.1 (SEQ ID NO: 41) substituted with an asparagine (N), or any non-alanine residue (e.g., one of positions 2-6 and 8-10 of SEQ ID NO: 10, or positions Q220, R221, M222, N223, T224, F226, T227 and P228 of NP_001340159.1) substituted with an alanine. In some embodiments, the core sequence of the peptide is selected from the group consisting of SEQ ID NOs: 28-37. In some embodiments, the core sequence of the peptide is selected from the group consisting of SEQ ID NOs: 29, 31-33, 36. In a specific embodiment, the core sequence of the peptide is SEQ ID NO: 31.

Examples of alterations or mutations of the core sequence are represented by SEQ ID NOs: 28-37. These FLCN-mutants inhibit LDHA activity. The sequences of SEQ ID NOs: 28-37 are provided below. The amino acid changed from SEQ ID NO: 10 is underlined.

```
                        (SEQ ID NO: 28)
NQRMNTAFTP (SEQ ID NO: 29)
AARMNTAFTP (SEQ ID NO: 30)
AQAMNTAFTP (SEQ ID NO: 31)
AQRANTAFTP (SEQ ID NO: 32)
AQRMATAFTP (SEQ ID NO: 33)
AQRMNAAFTP (SEQ ID NO: 34)
AQRMNTNFTP (SEQ ID NO: 35)
AQRMNTAATP (SEQ ID NO: 36)
AQRMNTAFAP (SEQ ID NO: 37)
AQRMNTAFTA
```

In some embodiments, the disclosure provides a peptide comprising or consisting of one of the core sequences defined by SEQ ID NOs: 28-37.

In some embodiments, the disclosure provides a peptide comprising or consisting of any one of the core sequences defined by SEQ ID NOs: 1-27. SEQ ID NO: 1 is a sequence from the wild-type FLCN protein. SEQ ID NOs: 1, 3, 7-9, 15-18, 20 and 22 are variations of this core sequence in which there are amino acid substitutions, truncations, and/or additional flanking amino acids. Single amino acid changes from the wild-type are underlined. Flanking amino acids are in bold. The amino acid that is changed over the corresponding wild-type sequence is shown as underlined.

```
                        (SEQ ID NO: 1)
QRMNTAFTPFL (SEQ ID NO: 3)
QRMNTGFTPFL (SEQ ID NO: 7)
QRMNTAFSPFL (SEQ ID NO: 8)
QRMDTAFTPFL (SEQ ID NO: 9)
ERMNTAFTPFL (SEQ ID NO: 15)
RMNTAFTP (SEQ ID NO: 16)
RMNTAFTPF (SEQ ID NO: 17)
RMNTAFTPFL (SEQ ID NO: 18)
TAFTPFL (SEQ ID NO: 20)
FTPFLHQ (SEQ ID NO: 22)
EQFGCPQRAQRMNTAFTPFL
```

In some embodiments, the disclosure provides a peptide comprising or consisting of any one of the core sequences defined by SEQ ID NOs: 2, 4-6, 11-14, 19, 21, 23-27. SEQ ID NO: 11 is a sequence from the wild-type FLCN protein. SEQ ID NOs: 4-6, 11-14, 19, 21, 23-27 are variations of this core sequence consisting of amino acid substitutions, truncations, or additional flanking amino acids. Single amino acid changes from the wild-type are underlined. Flanking amino acids are in bold. In some embodiments, the tyrosine at position 8 of SEQ ID NO: 27 is phosphorylated. These peptides may be used as controls for testing, such as for in vitro testing, or animal testing:

QRMNT<u>S</u>FTPFL (SEQ ID NO: 2)

QRMNTA<u>Y</u>TPFL (SEQ ID NO: 4)

QRMNTAFTP<u>Y</u>L (SEQ ID NO: 5)

QRMN<u>S</u>AFTPFL (SEQ ID NO: 6)

AQRMNTAFTPFL (SEQ ID NO: 11)

QRAQRMNTAFT (SEQ ID NO: 12)

QRMNTA (SEQ ID NO: 13)

RMNTAFT (SEQ ID NO: 14)

RMNTAFTPFLHQRNG (SEQ ID NO: 19)

EQFGCPQRAQ (SEQ ID NO: 21)

QR<u>A</u>NTAFTPFL (SEQ ID NO: 23)

CPQRAQRMNTA (SEQ ID NO: 24)

AFTPFLHQRNG (SEQ ID NO: 25)

CPQRAQRMNTAFTPFL (SEQ ID NO: 26)

QRMNTAFpTPFL (SEQ ID NO: 27)

Peptide Modifications

In some embodiments, the peptide of the present disclosure is modified to alter its properties (e.g., stability, binding affinity). As used herein, the term "stability" refers to resistance to cellular proteases and proteasomes (a peptide with increased, or improved stability is more resistant to degradation by cellular enzymes).

In some embodiments, the modification is selected from the group consisting of PEGylation, cyclization, retro-inversion, glycosylation, acylation, acetylation, lysine methylation, amidation, carbamoylation, cysteine oxidation, methionine oxidation, and phosphorylation.

As used herein, the term "PEGylation" refers to the process of both covalent and non-covalent attachment or amalgamation of polyethylene glycol (PEG) polymer chains to a molecule.

As used herein, the term "cyclization" refers to a process in which one part of a molecule (e.g., a peptide) becomes linked to another part of the molecule to form a closed ring.

As used herein, the term "retro-inversion" is a process where the amino acid sequence of the peptide is reversed and the α-center chirality of the amino acid subunits is inverted as well (from L to D isomers). As used herein, the term "glycosylation" refers to addition of a sugar molecule to a molecule (e.g., a peptide).

As used herein, the term "acylation" refers to the addition of an acyl group to a molecule (e.g., a peptide).

As used herein, the term "acetylation" refers to the addition of an acetyl group to a molecule (e.g., a peptide).

As used herein, the term "lysine methylation" refers to the addition of a methyl group to a lysine amino acid.

As used herein, the term "amidation" refers to the addition of an amide group to a molecule (e.g., a peptide).

As used herein, the term "carbamoylation" refers to the addition of a carbamoyl group to a molecule (e.g., a peptide).

As used herein, the term "phosphorylation" refers to the addition of a phosphate group to a molecule (e.g., a peptide).

In some embodiments, the peptide of the instant disclosure is modified by covalent attachment to carriers such as keyhole limpet hemocyanin (KLH), bovine serum albumin (BSA), and rabbit serum albumin (RSA). Conjugation to these carriers can be achieved via an N-terminal cysteine or C-terminal cysteine amide residue added to the peptide's sequence. In some embodiments, the present disclosure provides peptides, fragments thereof, or multimers thereof which has a N-terminal and/or a C-terminal cysteine. Other carriers such as ovalbumin, thyroglobulin, tetanus toxoid, diphtheria toxoid, tuberculin PPD may also be used. In a specific embodiment, the carrier is a nanoparticle, such as, for example, a gold nanoparticle. In some embodiments, the peptide, fragments thereof, or multimers thereof are purified. In some embodiments, the only peptides or proteins attached to the carriers are the peptides disclosed herein.

In some embodiments, the peptide of the present disclosure is conjugated to cell penetrating peptides (CPPs). In some embodiments, the peptide is conjugated to the N-terminus or the C-terminus of a CPP. In some embodiments, the peptide is conjugated to a HIV-TAT peptide. In some embodiments, the sequence of the HIV-TAT comprises YGRKKRRQRRR (SEQ ID NO: 38).

In some embodiments, the peptide is modified by one modification listed above. In some embodiments, the peptide is modified by more than one such as two or more, or several modifications together.

In some embodiments, the peptide comprises a core sequence of SEQ ID NO: 10 and is modified to increase its stability. In some embodiments, the modification is selected from the group consisting of PEGylation, cyclization, and retro-inversion.

Peptide Length

In some embodiments, the peptide of the disclosure is between 10-50 amino acids long (including the core sequence). In some embodiments, the peptide is 10, 11, 12, 13, 14, 15, 20, 25, 30, 35, 40, 45, or 50 amino acids long. In some embodiments, the peptide of the disclosure is between 10-30 amino acids long (including the core sequence).

In some embodiments, the peptide is longer than 10 amino acids, and the additional amino acids over 10 are flanking the N-terminus and/or the C-terminus of the core sequence. In some embodiments, the peptide is longer than 10 amino acids, and the additional amino acids over 10 are to the N terminus of the core sequence. In some embodiments, the peptide is longer than 10 amino acids, and the additional amino acids over 10 are to the C-terminus of the core sequence.

The peptide of this disclosure can be synthesized through methods known in the art (e.g., recombinant expression or solid phase peptide synthesis (SPPS)).

Pharmaceutical Compositions

In an aspect, the present disclosure also provides a pharmaceutical composition comprising a pharmaceutically acceptable carrier and one or more peptides of the present disclosure. Examples of carriers include solutions, suspensions, emulsions, solid injectable compositions that are dissolved or suspended in a solvent before use, and the like. The injections may be prepared by dissolving, suspending or emulsifying one or more of the active ingredients in a diluent. Examples of diluents include, but are not limited to distilled water for injection, physiological saline, vegetable oil, alcohol, dimethyl sulfoxide, and a combination thereof. Further, the injections may contain stabilizers, solubilizers, suspending agents, emulsifiers, soothing agents, buffers, preservatives, etc. The injections may be sterilized in the final formulation step or prepared by sterile procedure.

The composition of the disclosure may also be formulated into a sterile solid preparation, for example, by freeze-drying, and can be used after sterilized or dissolved in sterile injectable water or other sterile diluent(s) immediately before use. Additional examples of pharmaceutically include, but are not limited to, sugars, such as lactose, glucose, and sucrose; starches, such as corn starch and potato starch; cellulose, including sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Additional non-limiting examples of pharmaceutically acceptable carriers can be found in: *Remington: The Science and Practice of Pharmacy* (2005) 21*st Edition, Philadelphia, Pa. Lippincott Williams & Wilkins.*

Methods of Use and Treatment

The proteins and peptides of the present disclosure, or composition comprising the proteins and peptides may be used to alter (e.g., decrease) a cell's LDHA activity. The activity may be altered in vitro or in vivo. As such, the present compositions may be administered to an individual exhibiting an abnormal LDHA activity. The phrase "abnormal LDHA activity" refers to both increased LDHA activity as compared to the LDHA activity in a healthy control. In some embodiments, an individual may be exhibiting increased LDHA activity when the target cell's or organ's utilization of the glycolysis pathway is enhanced. Examples of conditions in which the present compositions can be used include any condition in which LDHA activity is abnormal. Conditions in which LDHA activity is abnormal include, but are not limited to, cancer and metabolic disorders. Specific examples of conditions include renal cancer, prostate cancer, breast cancer, lung cancer, melanoma, Birt-Hogg-Dubé syndrome, infectious diseases (e.g., malaria), and diabetes, mendelian disorders (e.g., hereditary disorders that show a Mendelian pattern of transmission between generations), inflammatory diseases, neurodegenerative and neuropathological disease, neuropsychological disorders, obesity and eating disorders, chronic diseases and genetic diseases.

In one aspect, the disclosure provides a method for treating an individual having or suspected of having cancer whose cancer has elevated LDHA activity. In some embodiments, a sample of the individual's tumor (e.g., biopsy sample) is used to measure LDHA activity. In some embodiments, if the tumor is found to have elevated LDHA activity as compared to the LDHA activity from a normal, healthy (i.e., non-cancerous) individual, a suitable (e.g., a therapeutically effective) amount of the peptide therapy is administered to the individual using a suitable route. In a specific embodiment, the peptide of the present disclosure is administered using intratumoral injection. In some embodiments, the treatment (administration of the peptide of the present disclosure) is carried out without first sampling of the tumor LDHA level. In some embodiments, a patient in need of treatment is administered a composition comprising a therapeutically effective amount of a peptide comprising a core sequence that differs from SEQ ID NO: 10 by a single amino acid substitution. In some embodiments, the individual is administered a composition comprising one or more peptides comprising or consisting of any one of SEQ ID NOs: 28-37.

In some embodiment, treating LDHA activity is decreasing the activity of the individual's LDHA enzymes. An individual in need of treatment may be a human or non-human mammal. Non-limiting examples of non-human mammals include cows, pigs, mice, rats, rabbits, cats, dogs, or other agricultural, pet, and service animals, and the like.

The compositions comprising one or more proteins or peptide of the present disclosure (e.g., one or more peptides of the present disclosure that are the same or different), may be administered or used in combination with additional anti-cancer treatments, drugs, or therapies, such as, surgery, chemotherapy, radiation therapy, small molecule inhibitors, immunotherapy, or any other suitable anti-cancer therapy or combinations thereof. In some embodiments, the peptide is administered before, during or after the additional therapy.

In some embodiments, one or more peptides of present disclosure (e.g., one or more peptides of the present disclosure that are the same or different) are administered to treat metabolic disorders (e.g., diabetes). In some embodiments, one or more compositions comprising a peptide of the present disclosure (e.g., one or more peptides of the present disclosure that are the same or different), are administered or used in combination with additional treatments, drugs, or therapies, such as, surgery, insulin, metformin, sulfonylureas, thiazolidinediones, GLP-1 receptor agonists, DPP-4 inhibitors, SGLT2 inhibitors, and meglitinides or any other suitable diabetes therapy or combinations thereof.

In some embodiments, the peptides of the instant disclosure are used or administered in combination, and the use or administration occurs simultaneously or sequentially. Any of the foregoing may be formulated in a combined formulation or in separate formulations.

In some embodiments, the peptides of present disclosure are administered to the subject in one or more ways including, but not limited to, injection by the intravenous, intra-arterial, intraperitoneal, intramuscular, intradermal, intrapulmonary, intranasal or oral, sublingual, dermal, and subcutaneous routes.

The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated. The compositions may be administered to an individual in need of treatment such as a human, or a non-human animal.

In an embodiment, a subject in need of treatment is administered a therapeutically effective amount of a peptide of the present disclosure. A dose of a therapeutically effective amount of a peptide of the present disclosure may have a concentration of 10 nM to 10 mM, including all 0.1 nM values and ranges therebetween. In some embodiments, a dose of a therapeutically effective amount of a peptide of the present disclosure has a concentration of 1-500 µM, 50-500 µM, 1-250 µM, 10-250 µM, 25-250 µM, 25-150 µM, 50-250

μM, or 50-150 μM. In a specific embodiment, the therapeutically effective amount of the peptide is 100 μM.

In some embodiments, a subject in need of treatment is administered a peptide of the present disclosure as a single dose (e.g., a single administration step). Following a single dose, the individual's LDHA hyperactivity is decreased for 1-120 hours (hr(s) or h) (e.g., 24-120 hours, 1-48 hours, 12-48 hours, or 24-48 hours), including all second values and ranges there between.

In an embodiment, a subject in need of treatment is administered a peptide of the present disclosure, a composition thereof, in multiple doses (e.g., multiple administration steps). Following the multiple doses, the individual's LDHA hyperactivity is ameliorated for 1-120 hours (e.g., 24-120 hours, 1-48 hours, 12-48 hours, or 24-48 hours), including all second values and ranges there between. In some embodiments, each does is administered to the patient in need of treatment every hour, every 2 hours, every 3 hours, every 4 hours, every 6 hours, every 8 hours, every 12 hours, every 24 hours, every 36 hours, and every 48 hours.

Kits

The disclosure also provides kits. A kit may comprise pharmaceutical preparations containing any one or any combination of compounds of the present disclosure. In an embodiment, the kit comprises a package (e.g., a closed or sealed package) that contains a pharmaceutical preparation in, for example, one or more closed or sealed vials, bottles, blister (bubble) packs, or any other suitable packaging for the sale, distribution, or use of the pharmaceutical compounds and compositions comprising them.

In an embodiment, the printed material includes, but not limited to, printed information. The printed information may be provided on a label, or on a paper insert, or printed on the packaging material itself. The printed information may include information that, for example, identifies the composition in the package, the amounts and types of other active and/or inactive ingredients, and instructions for taking the composition, such as, for example, the number of doses to take over a given period of time, and/or information directed to a pharmacist and/or another health care provider, such as a physician, or a patient. The printed material may include, for example, an indication that the pharmaceutical composition and/or any other agent provided with it is for treatment of an individual with a disease characterized by elevated LDHA activity. In an example, the product includes a label describing the contents of the container and providing indications and/or instructions regarding use of the contents of the container to treat an individual with a disease characterized by elevated LDHA activity.

In some embodiments, the present disclosure relates to a complementary deoxynucleotide (cDNA) sequence encoding an amino acid sequence having at least at least 90%, at least 95%, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38.

In some embodiments, the present disclosure relates to a composition including the variant peptide, or a synthetic amino acid sequence, including, or consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38.

In embodiments, the one or more peptides in accordance with the present disclosure are purified according to pharmaceutically acceptable techniques and added to pharmaceutically acceptable composition or formulations such as dosage forms. In embodiments, the concentration of one or more peptides in a composition, such as an powder formulation, can vary a great deal, and will depend on a variety of factors, including the type and severity of symptoms such as elevated LDHA activity, the desired duration of relief from elevated LDHA, possible adverse reactions, the effectiveness of the one or more peptides in lowering LDHA activity, and other factors within the particular knowledge of the patient and physician. In certain embodiments, compositions of the present disclosure can include an amount of one or more peptides of the present disclosure ranging from about 0.5 percent weight (wt %) to about 50 wt % of the total composition, in certain embodiments from about 0.5 wt % to about 5 wt % or the total composition, and in certain embodiments from about 5 wt % to about 20 wt % of the total composition. In embodiments, a single dosage may comprise about 2 to 3 micrograms/mL of one or more peptides in accordance with the present disclosure. In embodiments, a single about 2 to 3 micrograms/mL of one or more peptides in accordance with the present disclosure such as the polypeptides of SEQ ID NOS: 1-38, including SEQ ID NO: 10. In embodiments, the balance of the composition may include excipients, or adjuvants suitable for making a pharmaceutically acceptable formulation.

In embodiments, to prepare the drug product, the components of the pharmaceutical composition are blended and fabricated by methods known in the art. The resulting mixture is subsequently compacted in a press to yield individual (unit) dosages (blisters, tablets or capsules). To prepare the final drug product, the compressed dosage forms may undergo further processing, such as polishing, coating, and the like. In some embodiments, the peptides of the present disclosure are formulated into a pharmaceutically effective amount in a lyophilized formulation. In embodiments, one or more peptides are LDHA inhibitors and are disposed within a pharmaceutically acceptable vehicle. Accordingly, administration of the peptides such as isolated and purified peptides that inhibit LDHA activity of the present disclosure may be by oral, intravenous, intranasal, suppository, intraperitoneal, intramuscular, intradermal or subcutaneous administration or by infusion or implantation. When administered in such manner, the peptides of the present disclosure may be combined with other ingredients, such as carriers and/or adjuvants. There are no limitations on the nature of the other ingredients, except that they must be pharmaceutically acceptable, efficacious for their intended administration, cannot degrade the activity of the active ingredients of the compositions, and cannot impede importation of a subject peptide into a cell. The peptide compositions may also be impregnated into transdermal patches, or contained in subcutaneous inserts, such as in a liquid or semi-liquid form which patch or insert time-releases therapeutically effective amounts of one or more of the subject synthetic peptides. The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include but are not limited to a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents. Examples of such agents include paraben, chlorbutanol, phenol, sorbic acid or thimerosal. Isotonic agents such as sugars or sodium chloride may also be incorporated into the subject compositions.

In embodiments, methods of treating symptoms of elevated LDHA activity of the present disclosure can include administering to the subject a therapeutically effective amount of one or more peptides of the present disclosure to a patient in need of such treatment. In some embodiments, the present disclosure relates to a method of inhibiting lactate dehydrogenase A (LDHA) activity in a cell, including contacting the cell with an effective amount of the peptide of the present disclosure. In some embodiments, the cell has increased LDHA activity. In some embodiments, the cell is from an individual having or suspected of having cancer. In some embodiments, the cancer is renal, prostate, or breast cancer. In some embodiments, the cell is from an individual having or suspected of having a metabolic disorder. In some embodiments, the metabolic disorder is diabetes. In some embodiments, the cell is from an individual having or suspected of having Birt-Hogg-Dube syndrome.

In some embodiments, the present disclosure relates to a method of treating an individual having elevated levels of lactate dehydrogenase A (LDHA) activity including administering to the individual a therapeutically effective amount of a peptide including a core sequence that differs from SEQ ID NO: 10 by a single amino acid substitution. In some embodiments, the single amino acid substitution includes a non-natural amino acid substitution. In some embodiments, the non-natural amino acid substitution includes a substitution with a non-natural amino acid selected from a D-amino acid, a homo-amino acid, abeta homo amino acid, an N-methyl amino acid, and an alpha-methyl amino acid. In some embodiments, the core sequence is selected from the group consisting of SEQ ID NOs: 28-37. In some embodiments, the core sequence is selected from the group consisting of SEQ ID NOs: 29, 31, 32, 33 and 36. In some embodiments, the core sequence includes or consists of SEQ ID NO: 31. In some embodiments, the peptide includes a modification or alteration to increase stability. In embodiments, the modification is selected from the group consisting of PEGylation, cyclization, and retro-inversion. In embodiments, the peptide is between 10 and 30 amino acid long.

In some embodiments, the present disclosure relates to a method including: (a) obtaining a biological sample from an individual; (b) measuring the level of activity of the lactate dehydrogenase A (LDHA) enzyme in the biological sample; (c) comparing the activity measured in (c) to a reference standard; (d) administering to the individual a therapeutically effective amount of a peptide including a core sequence that differs from SEQ ID NO: 10 by a single amino acid substitution if the LDHA activity in the sample is higher than the LDHA activity in the reference standard. In some embodiments, the single amino acid substitution comprises a non-natural amino acid substitution. In some embodiments, the non-natural amino acid substitution includes substitution with a non-natural amino acid selected from a D-amino acid, a homo-amino acid, a beta homo amino acid, an N-methyl amino acid, and an alpha-methyl amino acid. In embodiments, the core sequence is selected from the group consisting of SEQ ID NOs: 28-37. In some embodiments, the core sequence is selected from the group consisting of SEQ ID NOs: 29, 31, 32, 33 and 36. In some embodiments, the core sequence comprises SEQ ID NO: 31. In some embodiments, the peptide is modified to increase stability. In some embodiments, the modification is selected from the group consisting of PEGylation, cyclization, and retro-inversion. In some embodiments, the peptide is between 10 and 30 amino acid long. In some embodiments, the method further includes measuring the level of activity of LDHA after the administration step to determine the efficacy of the treatment.

In some embodiments, the present disclosure relates to a kit including: (a) a peptide including a core sequence that differs from SEQ ID NO: 10 by a single amino acid substitution; and (b) instructions for use. In some embodiments, the single amino acid substitution includes anon-natural amino acid substitution. In some embodiments, the non-natural amino acid substitution comprises substitution with a non-natural amino acid selected from a D-amino acid, a homo-amino acid, a beta homo amino acid, an N-methyl amino acid, and an alpha-methyl amino acid. In some embodiments, the core sequence is selected from the group consisting of SEQ ID NOs: 28-37. In some embodiments, the core sequence is selected from the group consisting of SEQ ID NOs: 29, 31, 32, 33 and 36. In some embodiments, the core sequence includes SEQ ID NO: 31. In some embodiments, the peptide includes a modification or alteration to increase stability. In embodiments, the modification is selected from the group consisting of PEGylation, cyclization, and retro-inversion. In embodiments, the peptide is between 10 and 30 amino acid long.

In some embodiments, the present disclosure relates to a variant polypeptide including the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38. In embodiments, the variant is characterized as an LDHA inhibitor as the variant is able to inhibit or reduce LDHA activity when contacted with one or more cells.

In some embodiments, variants of the present disclosure have least 70% amino acid sequence identity to an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO:

38. In embodiments, the variant is characterized as an LDHA inhibitor as the variant is able to inhibit or reduce LDHA activity when contacted with one or more cells.

In some embodiments, variants of the present disclosure have at least 80% amino acid sequence identity to an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38. In embodiments, the variant is characterized as an LDHA inhibitor as the variant is able to inhibit or reduce LDHA activity when contacted with one or more cells.

In some embodiments, variants of the present disclosure have at least 90% amino acid sequence identity to an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38. In embodiments, the variant is characterized as an LDHA inhibitor as the variant is able to inhibit or reduce LDHA activity when contacted with one or more cells.

In some embodiments, variants of the present disclosure have at least 95%, 97%, or 99% amino acid sequence identity to an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38. In embodiments, the variant is characterized as an LDHA inhibitor as the variant is able to inhibit or reduce LDHA activity when contacted with one or more cells.

In some embodiments, the present disclosure relates to a variant polypeptide consisting of the amino acid sequence of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38. In embodiments, the variant is characterized as an LDHA inhibitor as the variant is able to inhibit or reduce LDHA activity when contacted with one or more cells.

In some embodiments, the present disclosure relates to a synthetic amino acid sequence, including, or consisting of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO:14, SEQ ID NO:15, SEQ ID NO:16, SEQ ID NO:17, SEQ ID NO:18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 38. In embodiments, the synthetic amino acid sequence is characterized as an LDHA inhibitor and able to inhibit or reduce LDHA activity when contacted with one or more cells. In some embodiments, the synthetic amino acid sequence is characterized as recombinant.

In some embodiments, the present disclosure relates to a composition including a polypeptide or variant described herein. In embodiments, a method of treating, ameliorating, or preventing one or more symptoms including elevated LDHA activity includes: administering a therapeutically effective amount of a polypeptide of the present disclosure to a subject in need thereof. The method of the present disclosure, wherein the polypeptide is a pharmaceutically acceptable salt, hydrate or solvate thereof. In embodiments, polypeptide is disposed within a pharmaceutically acceptable vehicle.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

Unless defined otherwise, all technical and scientific terms used herein have the same meaning as commonly understood by one skilled in the art to which this invention belongs.

Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The following non-limiting examples are presented to illustrate the present disclosure.

Example 1

Materials and Methods
Mass Spectrometry

Visible bands were excised from the gel manually and cut into small pieces approximately 1 mm×1 mm. These gel pieces were destained using 1:130 mM potassium ferricyanide: 100 mM sodium thiosulfate for 10 minutes. The destained gel pieces were then washed with 25 mM ammonium bicarbonate and acetonitrile alternatively for 5 minutes each wash. This cycle of 5-minute 25 mM ammonium bicarbonate wash followed by 5 minute acetonitrile wash was repeated 3 times. To further prepare the gel pieces for digestion, the gel pieces were then dehydrated in 100% acetonitrile. After removing all acetonitrile, 25 ml of porcine trypsin (Promega) dissolved in 25 mM ammonium bicarbonate at a concentration of 4 mg/ml was added to the gel pieces. The gel pieces were then kept at room temperature overnight (approximately 12-16 hours). Following digestion, the supernatant was transferred to a second tube, and acetonitrile was added to the gel pieces to complete the extraction of digested peptides. This extract was added to the first supernatant and this combined solution, containing the extracted peptides was frozen and lyophilized. The peptides were resuspended in 5 ml of 100:99:1 acetonitrile:water: trifluoroacetic acid immediately prior to spotting on the MALDI target. For MALDI analysis, the matrix solution consisted of alpha-cyano-4-hydroxycinnamic acid (Aldrich Chemical Co. Milwaukee, Wis.) saturating a solution of 1:1:0.01 acetonitrile: 25 mM ammonium citrate: trifluoroacetic acid. Approximately 0.15 ml of peptide solution was spotted on the MALDI target immediately followed by 0.15 ml of the matrix solution. This combined solution was allowed to dry at room temperature. MALDI MS and MS/MS data was then acquired using the ABSCIEX TOF/ TOF_5800 Mass Spectrometer. Resultant peptide mass fingerprint and peptide sequence data was submitted to the UniProt database using the Mascot search engine to which relevance is calculated and scores are displayed.

Protein Extraction, Immunoprecipitation, Pulldown and Immunoblotting

Protein extraction from mammalian cells was carried out using methods previously described (Mollapour M. et al., *Mol Cell.* 2010; 37(3):333-43). For immunoprecipitation, mammalian cell lysates were incubated with anti-FLAG or anti-HA antibody conjugated agarose beads (Sigma) for 2 hr at 4° C., or with anti-LDHA or anti-FLCN antibody for 1 hr followed by protein G agarose for 2 hr at 4° C. For biotinylated peptide pulldown, lysates were incubated with biotinylated peptide for 1 hr at 4 C, followed by incubation with streptavidin agarose for 1 hr at 4° C. Immunopellets were washed 4 times with fresh lysis buffer (20 mM Tris-HCl (pH 7.4), 100 mM NaCl, 1 mM MgCl2, 0.1% NP40, protease inhibitor cocktail (Millipore-Sigma), and PhosSTOP (Millipore-Sigma)) and eluted in 5× Laemmli buffer. Precipitated proteins were separated by SDS-PAGE and transferred to nitrocellulose membranes. Co-immunoprecipitated proteins were detected by immunoblotting with primary antibodies followed by secondary antibodies raised against mouse, rabbit, and rat (Cell Signaling) at 1:4000 dilution.

LDH Activity Assay

Lactate dehydrogenase activity was measured according to the manufacturer's protocol (MAK066, Sigma-Aldrich). In brief, 25 ng recombinant LDHA was pre-incubated with either peptide (1 μM) or recombinant FLCN protein (0.05, 0.25, 1, 5 nM) for 30 minutes on ice. Samples were then transferred to an optically clear 96-well plate and substrate mix was added to each well. Absorbance was measured at 450 nm every five minutes until saturation. For measurement of LDH activity in lysates, 1 μg of whole cell lysate was diluted into 50 μl total volume with 1× assay buffer in a 96-well plate. Absorbance at 450 nm was measure every five minutes following addition of substrate mix. All experiments were carried out in triplicate.

Protein Purification

FLCN and LDHA were expressed and purified from *E. coli* strain BL21 (DE3). Transformed cells were grown at 37° C. in LB with 50 mg/L ampicillin or kanamycin until $OD_{600}$=0.6. The cultures were then cooled to 30° C., induced with 1 mM IPTG, and grown to $OD_{600}$=1.2. Cells were harvested by centrifugation and lysed by sonication in fresh lysis buffer without detergent (20 mM Tris-HCl (pH 7.4), 100 mM NaCl, 1 mM MgCl2, protease inhibitor cocktail (Millipore-Sigma) and PhosSTOP (Millipore-Sigma)). After sonication, Triton X-100 was added to a final concentration of 1% prior to pelleting insoluble debris by centrifugation. Supernatant was collected and expression was assessed by immunoblotting. Isolation was accomplished by two sequential Ni-NTA agarose (QIAGEN) pulldowns. Lysate was incubated with Ni-NTA agarose (QIAGEN) for 2 hr at 4° C. Proteins bound to Ni-NTA agarose were washed three times with lysis buffer (as above) followed by two washes with 50 mM imidazole in lysis buffer. They were then eluted in 500 mM imidazole in lysis buffer and concentrated in 10K Amicon Ultra Centrifugal Filters (Millipore). Concentrations were determined using the Micro BCA Protein Assay Kit (Thermo Scientific) per manual protocol. Purified protein was run on an SDS-PAGE gel and Coomassie stained to confirm purity prior to use in assays.

$K_d$ Measurements

LDHA at the indicated concentrations was incubated on ice in 50 mM Tris pH 7.2, 150 mM NaCl, 1 mM TCEP, 4 mM MgCl2 with 1 mM labelled FLCN peptide for 30 min.

Fluorescence anisotropy was measured using a SpectraMax 3 equipped with rhodamine fluorescence polarization module (lex\lem.535 nm/595 nm). Curve fitting was done in KaleidaGraph 4.0.

Seahorse Metabolic Assay

UOK cells were transfected in 100 mm dishes at 50% confluency and incubated for 24 hr. Subsequently, cells were seeded at $10^5$/well 24 hr prior to assay initiation in a 96-well plate. Glycolytic stress test was then carried out on an Agilent Seahorse XF instrument according to the manufacturer's protocol.

Ex Vivo Peptide Treatment

Tumor tissues from the BHD patient were obtained with written informed consent from the Department of Urology at SUNY (State University of New York) Upstate Medical University. At the time of partial nephrectomy, which was done with <15 min of renal ischemia, BHD tumors were dissected into 3-5 $mm^3$ pieces and cultured on a presoaked gelatin sponge (Johnson & Johnson) in 24-well plates containing 2 ml RPMI-1640 with 10% FBS, antibiotic/antimycotic solution. Tissues were cultured at 37° C. for 16 hr, followed by the addition of the indicated concentrations of FLCN-10-Rhod-B and further incubation at 37° C. for 2 hr.

Peptide Synthesis

Peptides were synthesized and HPLC purified by Life Technologies.

Flow Cytometric Analysis

FACS analysis was performed according the protocol in the Annexin V:FITC kit (Bio-Rad). In brief, cells were plated at $0.5 \times 10^8$ and incubated at 37° C. for 16 hr. Cells were subsequently treated with FLCN-10 peptide at indicated concentrations for 2 hr. Cells were trypsinized, collected, and washed once with 1× binding buffer. Annexin V-FITC was added at 1:40 and incubated for 10 minutes at room temperature in the dark. Following one wash with 1× binding buffer, propidium iodide was added and immediately run on a BD Fortessa.

Quantification and Statistical Analysis

All statistics were performed using GraphPad Prism version 7.00 for Windows (GraphPad Software, La Jolla, Calif., USA). Statistical significance was ascertained between individual samples using a parametric unpaired t-test. Significance was denoted as asterisks in each figure: *$p<0.05$; $p<0.01$; *$p<0.001$; ****$p<0.0001$. Error bars represent the standard deviation (SD) for three independent experiments, unless it is indicated.

Results

FLCN Specifically Binds and Inhibits LDHA.

FLCN is a known tumor suppressor, however the exact function of FLCN remains elusive due to opposing reports providing inconclusive evidence towards its bona fide function (Petit C S. et al., *J Cell Biol.* 2013; 202(7):1107-22; Tsun Z Y. et al., *Mol Cell.* 2013; 52(4):495-505). To elucidate the molecular mechanism of FLCN function, the inventors performed a pulldown of FLCN-6xHis from HEK293 cell lysate followed by mass spectrometry. The inventors found several molecular chaperones previously identified, including heat shock protein-90 (Hsp90), Hsp70, protein phosphatase-5, CHIP, and FLCN-Interacting protein 1 (FNIP1) and FNIP2 (Woodford M R. et al., *Nature communications.* 2016; 7:12037) as well as lactate dehydrogenase-A (LDHA) (FIG. 1A). The inventors confirmed the interaction with LDHA by immunoprecipitation (IP) of LDHA-FLAG and co-IP of endogenous FLCN (FIG. 1B). Further, overexpression of FLCN perturbs the activity of LDHA, as evidenced by the decreased signal of the activation-coupled phospho-Tyr10-LDHA (FIG. 1C) (Fan J. et al. *Mol Cell Biol.* 2011; 31(24):4938-50; Jin L. et al. *Oncogene.* 2017; 36(27):3797-806). LDHA and LDHB are highly conserved isoenzymes (Read J A. et al., *PROTEINS: Structure, Function, and Genetics.* 2001; 43:175-85), and both are expressed in HEK293 cells. Interestingly, immunoprecipitation of FLCN-FLAG from whole cell lysate shows FLCN specifically binds to LDHA, but not LDHB (FIG. 1D).

Figure 5:
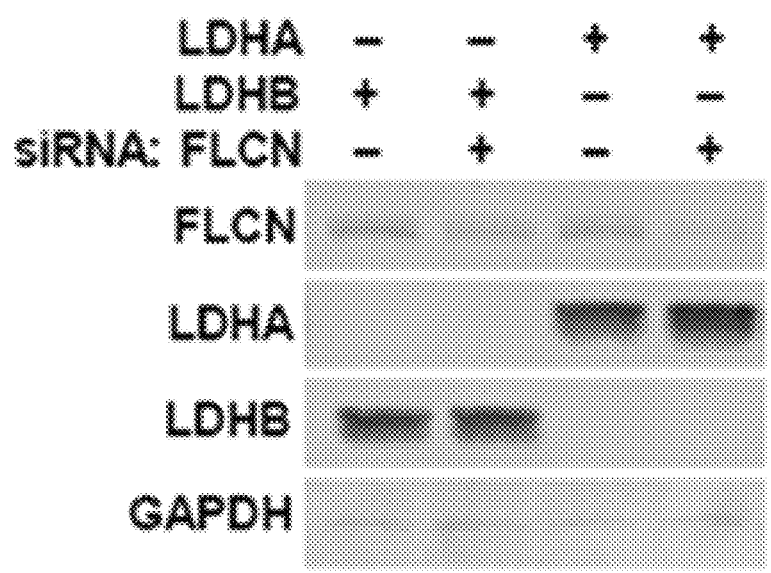
FIG. 5 presents illustrative data relating to Western blot of siRNA knockdown of FLCN for FIG. 1E.

LDHA and LDHB form mixed tetrameric complexes ranging from LDH1 (four LDHB monomers) to LDH5 (four LDHA monomers) (Yamamoto S. et al., *Int J Biochem.* 1988; 20(11):1261-5). These tetramers are often described as a "dimer of dimers" because at steady state LDH is dimeric, while in Warburg-shifted tumors the dimers associate, yielding a hyperactive LDH tetramer (Fan J. et al. *Mol Cell Biol.* 2011; 31(24):4938-50; Jin L. et al. *Oncogene.* 2017; 36(27):3797-806; Zheng Y. et al., *Biochemistry (Mosc).* 2004; 69(4):401-6). Consecutive immunoprecipitation of co-expressed LDHA-HA/LDHA-FLAG or LDHA-HA/LDHB-FLAG allowed isolation of LDHA/LDHA homodimers or LDHA/LDHB heterodimers. Co-immunoprecipitation of FLCN was observed only in the LDHA/LDHA homodimers (FIG. 1E). Further confirming this finding, the inventors performed siRNA knockdown of FLCN in the haploid HAP1 cells, modified by CRISPR to express either LDHA or LDHB as the sole LDH (FIG. 5).

Figures 1D, 1E, 1F, 1G, 1H, 1I, 1J:
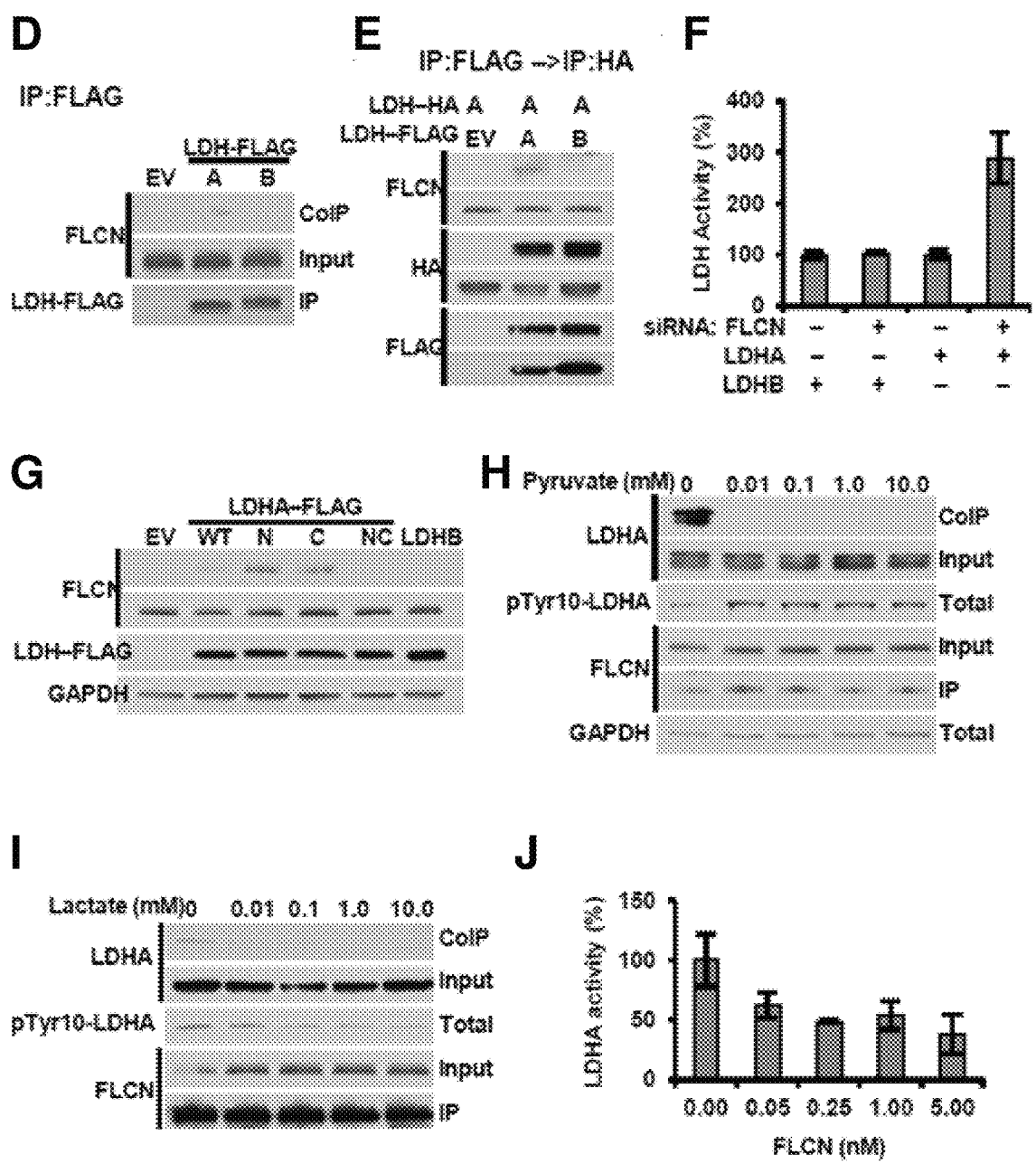
FIG. 1D presents illustrative immunoblotting data for A-FLAG or LDHB-FLAG expressed in HEK293 cells and immunoprecipitated, wherein interaction with FLCN was examined by immunoblotting.
FIG. 1E presents illustrative immunoblotting data for LDHA and LDHB subunits immunoprecipitated and immunoblotted with FLCN.
FIG. 1F presents illustrative data for measurement of LDH activity in lysates from LDHA or LDHB knockout HAP1 cells followed by siRNA knock-down of FLCN.
FIG. 1G presents illustrative data for LDHA/LDHB chimeric constructs transfected into HEK293 cells and immunoprecipitated, wherein co-immunoprecipitation of FLCN was detected by immunoblot.
FIG. 1H presents illustrative data of an immunoblot for FLCN and LDHA following exogenous addition of pyruvate to HEK293s.
FIG. 1I presents illustrative data of an immunoblot for FLCN and LDHA following exogenous addition of lactate to HEK293s.
FIG. 1J presents illustrative data for measurement of LDHA activity in the presence of increasing amounts of FLCN.

Decreased FLCN expression enhanced the activity of LDHA, but not LDHB (FIG. 1F). LDHA and LDHB are 75% identical, and much of the sequence variation is in the first 22 (N) and last 38 (C) amino acids (Valvona, et al., 2016). The inventors therefore asked whether these two regions determine the binding specificity of LDHA to FLCN. The inventors created chimeric LDHA constructs containing either the N-domain or C-domain of LDHB, or both. Swapping the LDHB N-domain or C-domain individually into LDHA did not affect binding of FLCN (FIG. 1G). Exchange of both domains (NC) however completely abrogated FLCN interaction, similar to wild-type LDHB (FIG. 1G). Canonically, LDHA is activated in cells by pyruvate accumulation (Tarmy E M. et al., *J Biol Chem.* 1968; 243(10):2587-96; Jiang G R. et al., *Microbiology.* 2001; 147(Pt 9):2437-46). To evaluate whether the activation of LDH is coupled to its dissociation from FLCN, HEK293 cells were treated with increasing amounts of pyruvate.

LDHA activation resulted in disruption of the FLCN-LDHA complex, as co-immunoprecipitation of LDHA with FLCN was only achieved in the absence of exogenous pyruvate (FIG. 1H). Interestingly, addition of lactate resulted in a dose-dependent dissociation of LDHA from FLCN (FIG. 1I), whereas pre-incubation of LDHA with recombinant FLCN attenuates LDHA activation in a dose-dependent manner in vitro (FIG. 1J). Taken together, the data suggests that the tumor suppressor FLCN specifically binds to LDHA and not LDHB and inhibits its enzyme activity. The data further demonstrates that the tight binding of pyruvate readily causes FLCN to dissociate from LDHA, while the relatively weak binding of lactate does not effectively disrupt the FLCN/LDHA interaction (Cahn R D. et al., *Science.* 1962; 136(3520):962-9).

As described herein, FIGS. 1A-1J relate to the tumor suppressor folliculin (FLCN) specifically binding to and inhibiting LDHA. FIG. 1A shows FLCN-FLAG immunoprecipitated from HEK293 cells was subjected MALDI-TOF. (+) and (−) represent chaperones and co-chaperone interactions. (x) and (#) are ribosomal proteins and splicing factors, respectively. Referring to FIG. 1B, and FIG. 1C, LDHA-FLAG or FLCN-FLAG immunoprecipitated from HEK293 cells was immunoblotted for FLCN and LDHA. Referring to FIG. 1D A-FLAG or LDHB-FLAG were expressed in HEK293 cells and immunoprecipitated. Interaction with FLCN was examined by immunoblotting. Referring to FIG. 1E, LDHA and LDHB subunits were consecutively immunoprecipitated and immunoblotted with FLCN. Referring to FIG. 1F, measurement of LDH activity in lysates is shown from LDHA or LDHB knockout HAP1 cells followed by siRNA knock-down of FLCN. Referring to FIG. 1G LDHA/LDHB chimeric constructs were transfected into HEK293 cells and immunoprecipitated. Co-immunoprecipitation of FLCN was detected by immunoblot. Referring to FIG. 1H, an immunoblot for FLCN and LDHA following exogenous addition of pyruvate is shown or FIG. 1I lactate to HEK293s. Referring to FIG. 1J, measurement of LDHA activity in the presence of increasing amounts of FLCN is shown.

Figure 2A:
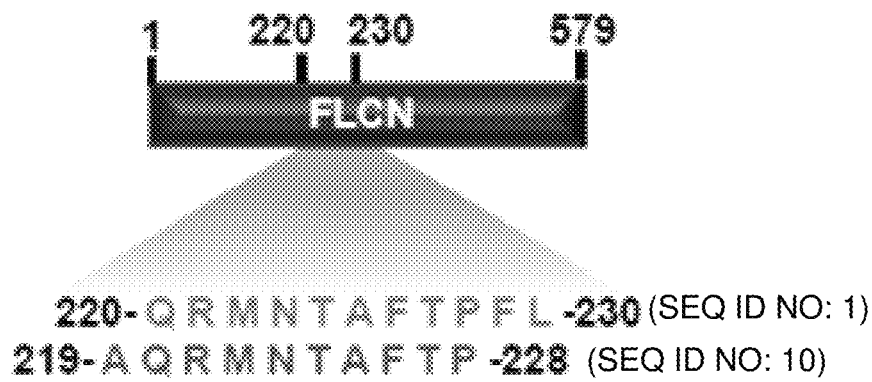
FIG. 2A is a schematic illustration of the amino acid sequence of SEQ ID NO: 1 and SEQ ID NO: 10.
Figure 2B:
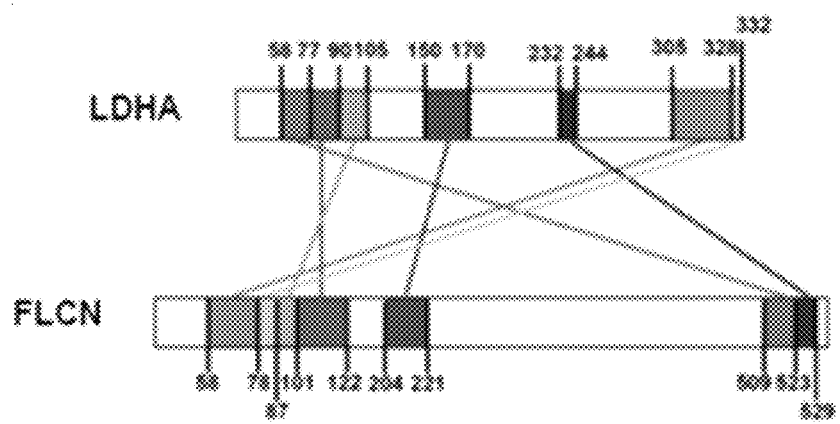
FIG. 2B is a schematic illustration of crosslinking MS identification of interactions between FLCN and LDHA.
Figures 2C, 2D, 2E:
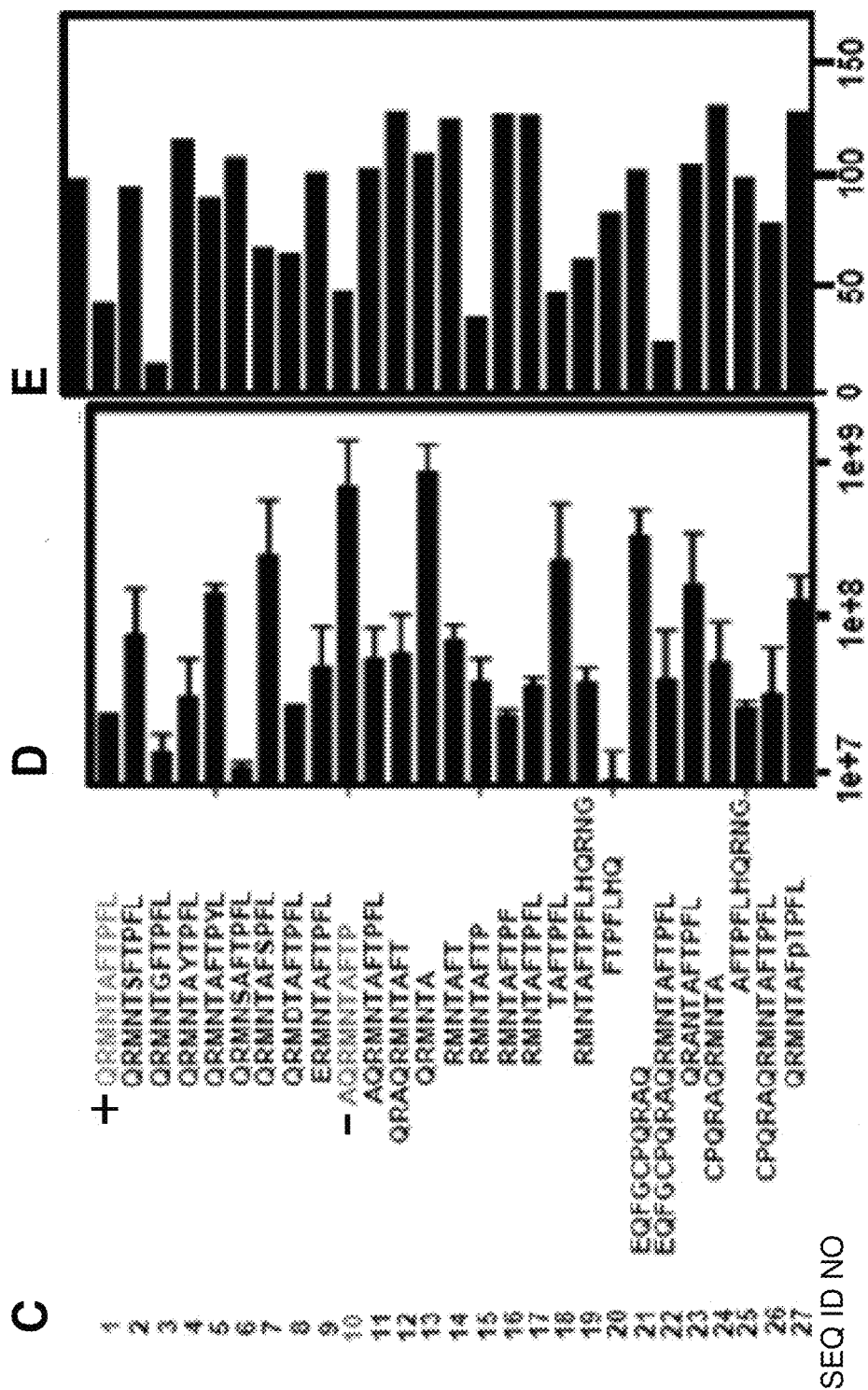
FIG. 2C shows SEQ ID NOS: 1-27.
FIG. 2D presents illustrative data for measurement of equilibrium association constant ($K_a$).
FIG. 2E presents illustrative data for ability to inhibit LDHA activity.
Figure 2F:
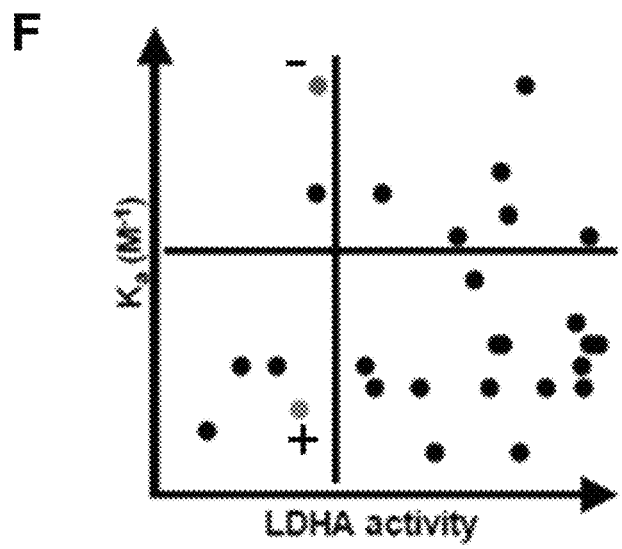
FIG. 2F presents illustrative data for $K_a$ plotted against LDHA activity in the presence of peptides of the present disclosure.
Figure 2G:
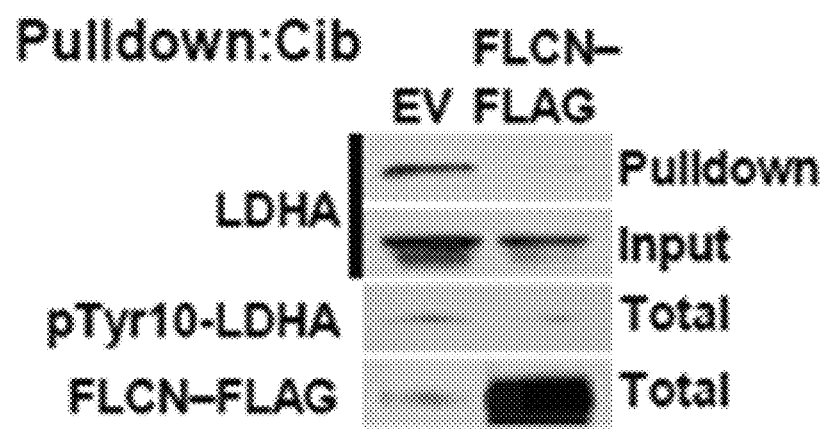
FIG. 2G presents illustrative immunoblot data for LDHA binding to Cibacron blue agarose (analog of AMP mimicking the substrate of LDHA.
Figure 2H:
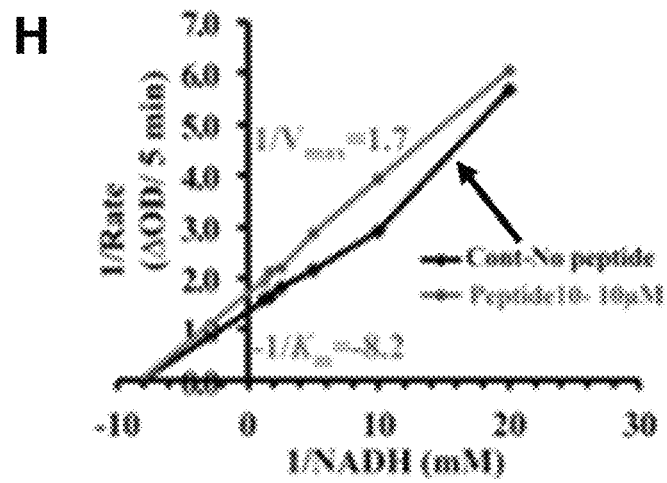
FIG. 2H presents illustrative data relating to FLCN-10 as a non-competitive inhibitor of LDHA based on Lineweaver-Burke plot.
Figure 2I:
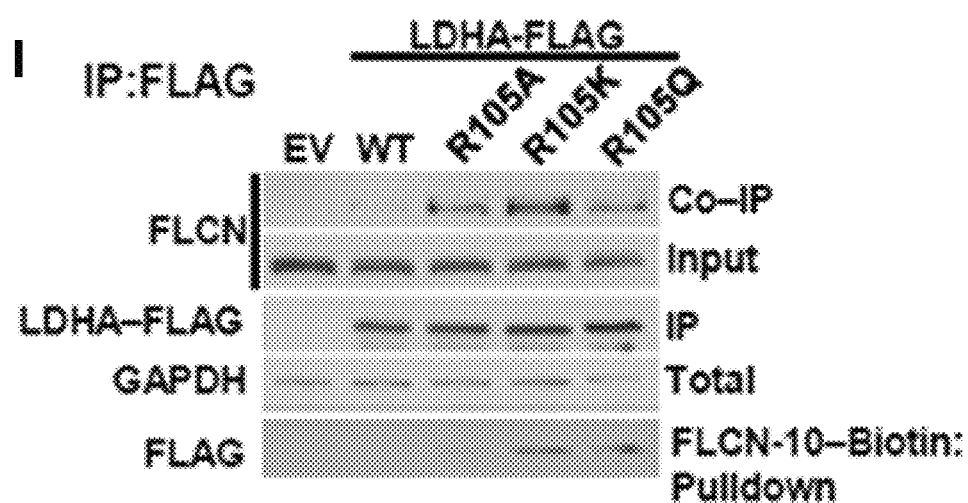
FIG. 2I presents illustrative immunoblot data relating to LDHA-R105-FLAG mutants transiently transfected and isolated from HEK293s, wherein FLCN interaction was assessed by immunoblotting.

Referring now to FIG. 2A-2I decameric peptide of FLCN are shown to non-competitively inhibit LDHA. Referring to FIG. 2A a schematic of FLCN protein highlighting original peptide (+) and FLCN-10 (−) is shown. In FIG. 2B, cross-linking MS identification of interactions between FLCN and LDHA. In FIG. 2C, FLCN peptides screened for (See FIG. 2D), $K_a$ or (see FIG. 2E), ability to inhibit LDHA is shown. The peptides compared in these experiments include: 1—QRMNTAFTPFL (SEQ ID NO: 1), 2—QRMNTSFTPFL (SEQ ID NO: 2), 3—QRMNTGFTPFL (SEQ ID NO: 3), 4—QRMNTAY-TPFL (SEQ ID NO: 4), 5—QRMNTAFTPYL (SEQ ID NO: 5), 6—QRMNSAFTPFL (SEQ ID NO: 6), 7—QRMN-TAFSPFL (SEQ ID NO: 7), 8—QRMDTAFTPFL (SEQ ID NO: 8), 9—ERMNTAFTPFL (SEQ ID NO: 9), 10—AQRMNTAFTP (SEQ ID NO: 10), 11—AQRMN-TAFTPFL (SEQ ID NO: 11), 12—QRAQRMNTAFT (SEQ ID NO: 12), 13—QRMNTA (SEQ ID NO: 13), 14—RMN-TAFT (SEQ ID NO: 14), 15—RMNTAFTP (SEQ ID NO: 15), 16—RMNTAFTPF (SEQ ID NO: 16), 17—RMN-TAFTPFL (SEQ ID NO: 17), 18—TAFTPFL (SEQ ID NO: 18), 19—RMNTAFTPFLHQRNG (SEQ ID NO: 19), 20—FTPFLHQ (SEQ ID NO: 20), 21—EQFGCPQRAQ (SEQ ID NO: 21), 22—EQFGCPQRAQRMNTAFTPFL (SEQ ID NO: 22), 23—QRANTAFTPFL (SEQ ID NO: 23), 24—CPQRAQRMNTA (SEQ ID NO: 24), 25—AFTP-FLHQRNG (SEQ ID NO: 25), 26—CPQRAQRMN-TAFTPFL (SEQ ID NO: 26), 27—QRMNTAFpTPFL (SEQ ID NO: 27). Referring to FIG. 2F, $K_a$ plotted against LDHA activity in the presence of peptides is shown. Referring to FIG. 2G, lysates collected from cells expressing EV or FLCN-FLAG are shown. LDHA binding to Cibacron blue agarose (analog of AMP mimicking the substrate of LDHA) was evaluated by immunoblot. Referring to FIG. 2H, FLCN- 10 is shown as a non-competitive inhibitor of LDHA based on Lineweaver-Burke plot. Referring to FIG. 2I, it is shown that LDHA-R105-FLAG mutants were transiently transfected and isolated from HEK293s. FLCN interaction assessed by immunoblotting.

Figure 3A:
FIG. 3A is a schematic representation of FLCN protein highlighting individual amino acid mutations in FLCN-10 residues (underlined) in accordance with some embodiments of the present disclosure.
Figure 3B:
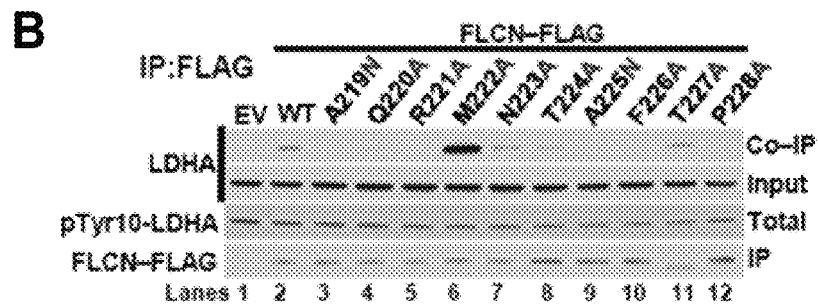
FIG. 3B presents illustrative data relating to mutations of the FLCN peptide region were expressed in HEK293 cells and immunoprecipitated using anti-FLAG agarose.
Figures 3C, 3D:
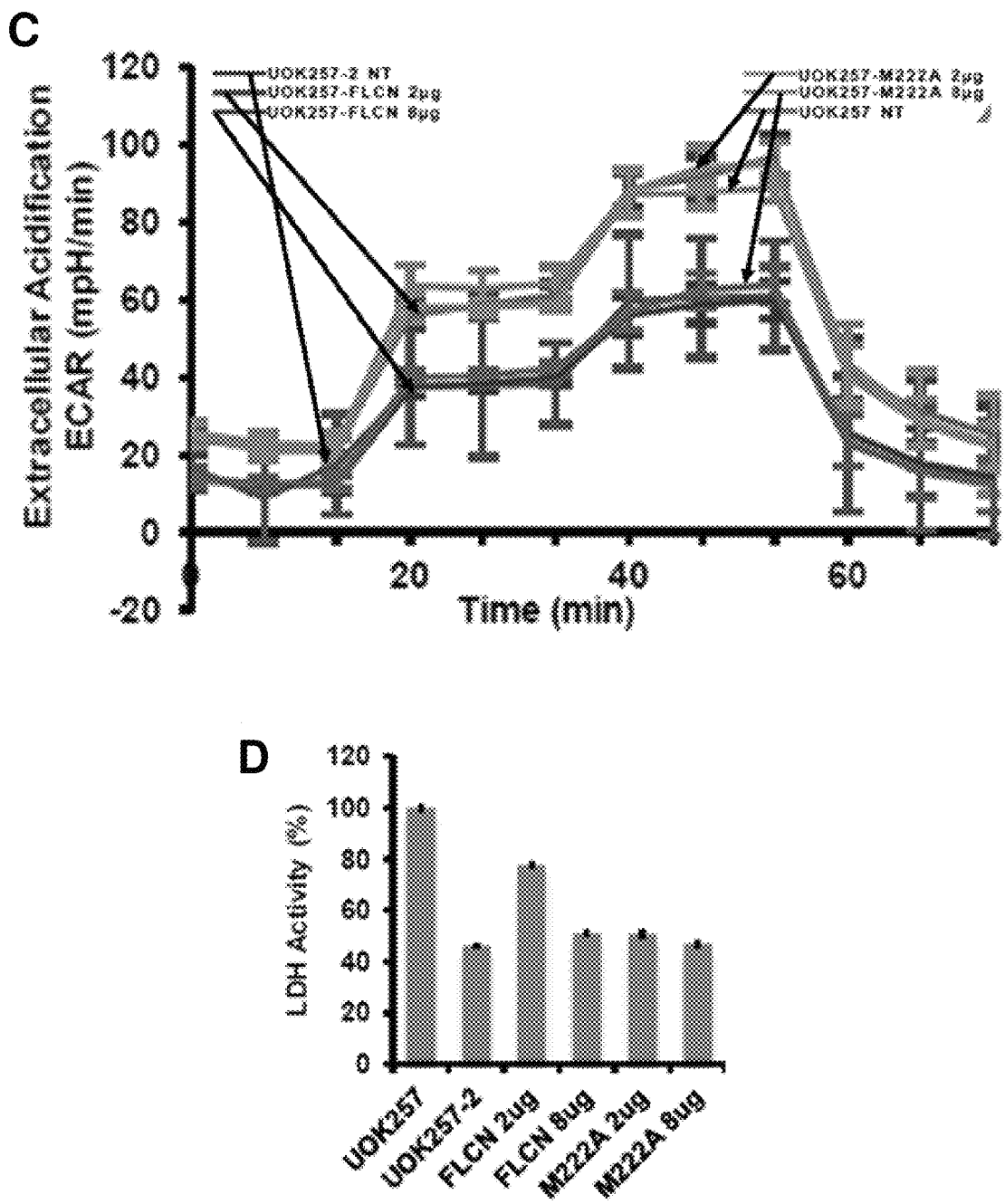
FIG. 3C is a graph referring to extracellular acidification rate of UOK257 cells transfected with 2 μg and 8 μg of WT FLCN or M222A mutant.
FIG. 3D presents illustrative data relating to LDHA activity of lysates collected from UOK257 cells of FIG. 3C.
Figure 3E:
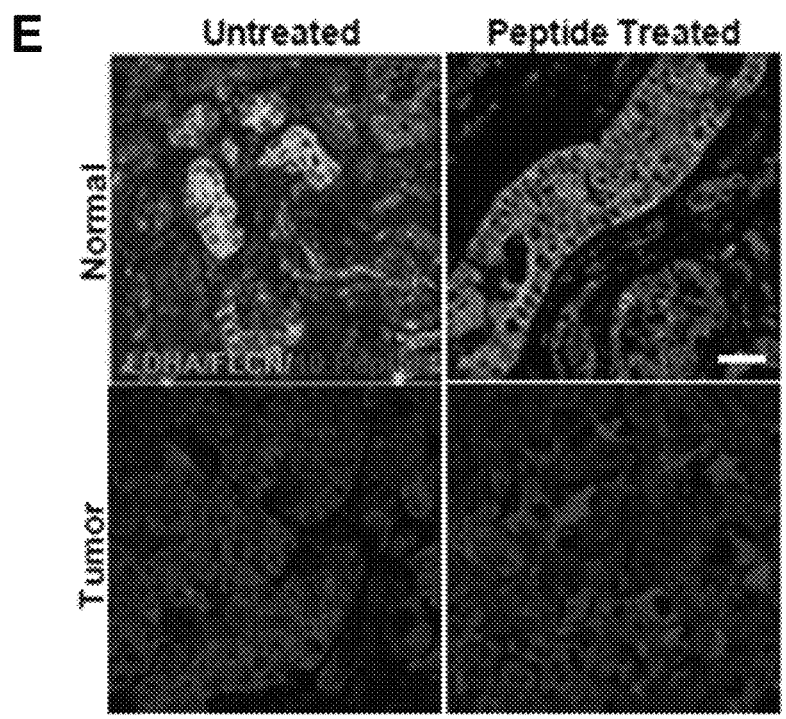
FIG. 3E relates to tumor and normal renal tissues from a BHD patient treated with FLCN-10-Rhodamine B and stained for FLCN, LDHA and DNA by Hoechst 33258, wherein the scalebar is 20 μm.
Figure 3F:
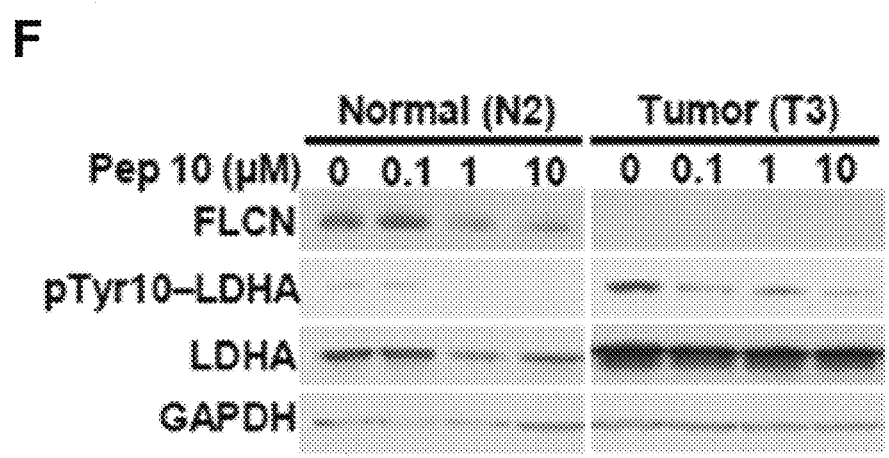
FIG. 3F presents illustrative data relating to western blots of lysates.

Referring now to FIGS. 3A-3F it is shown that LDHA hyperactivity is abrogated by FLCN peptide ex vivo in BHD kidney tumors. FIG. 3A shows a schematic representation of FLCN protein highlighting individual amino acid mutations in FLCN-10 residues (underlined). FIG. 3B refers to mutations of the FLCN peptide region expressed in HEK293 cells and immunoprecipitated using anti-FLAG agarose. Interaction with LDHA was assessed by immunoblot. FIG. 3C refers to extracellular acidification rate of UOK257 cells transfected with 2 µg and 8 µg of WT FLCN or M222A mutant. FIG. 3D refers to LDHA activity of lysates collected from cells of FIG. 3C. FIG. 3E refers to tumor and normal renal tissues from a BHD patient treated with FLCN-10-Rhodamine B and stained for FLCN, LDHA and DNA by Hoechst 33258, scalebar 20 µm. FIG. 3F refers to Western blots of lysates collected from FIG. 3E samples.

Figures 4A, 4B, 4C:
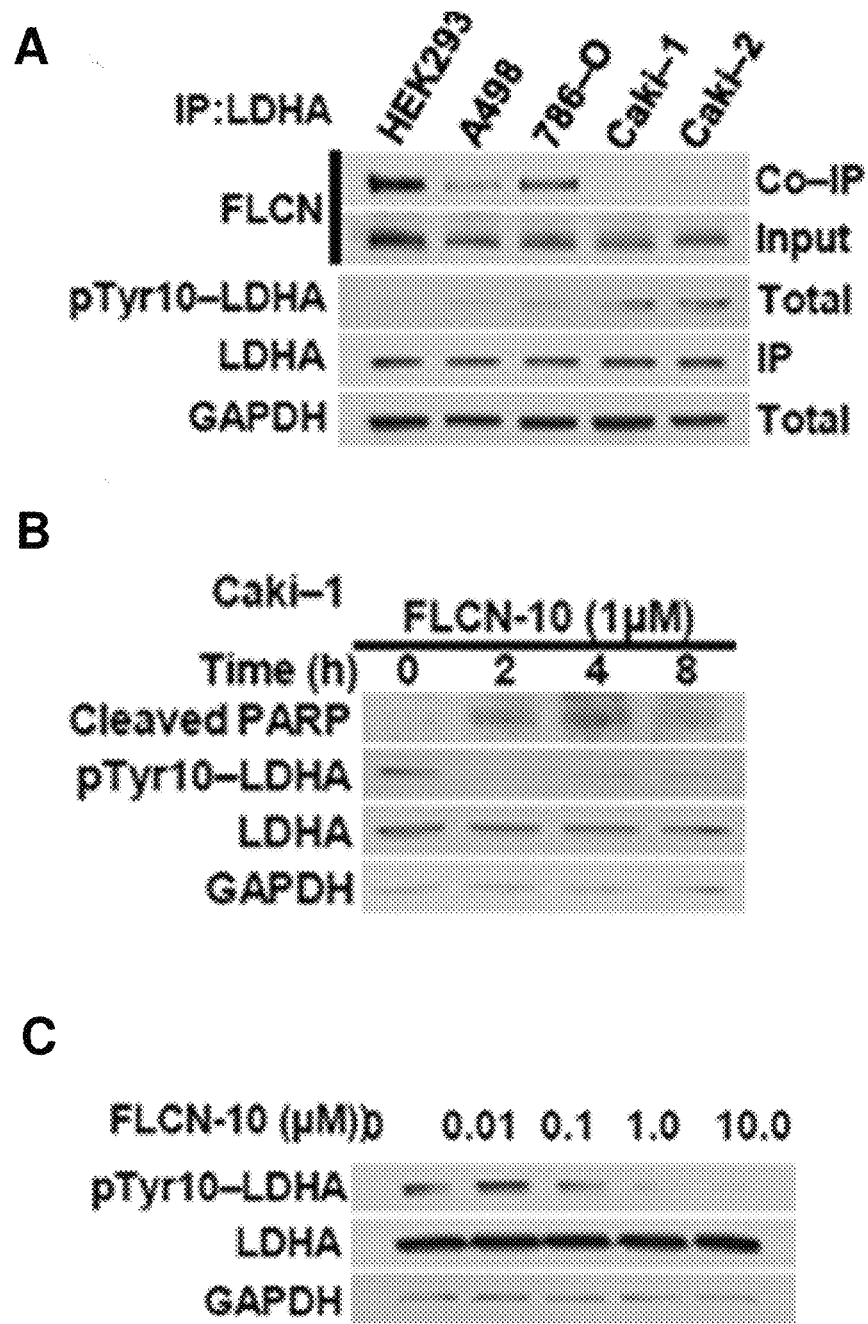
FIG. 4A presents illustrative data relating to endogenous LDHA immunoprecipitated from renal cell lines, wherein interaction with FLCN was observed by immunoblot in accordance with some embodiments of the present disclosure.
FIG. 4B presents illustrative data relating to Caki-1 cells treated with FLCN-10 blotted for cleaved PARP and pTyr10-LDHA.
FIG. 4C presents illustrative data relating to flow cytometric assessment of cell death in renal cell lines following 1 μM FLCN-10 after one- or two-hours treatment as determined by Annexin V/Propidium iodide staining.
Figures 4D, 4E:
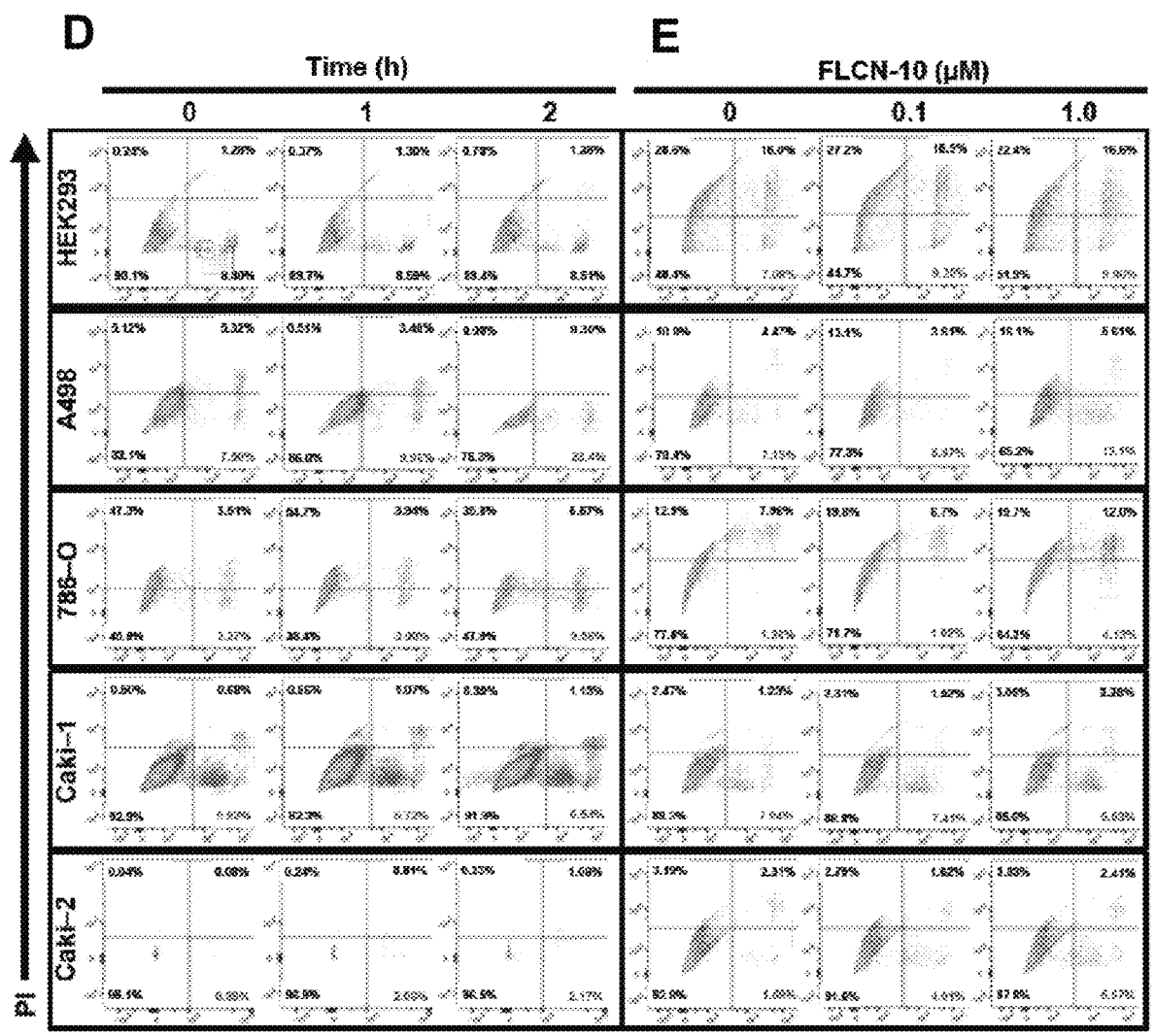
FIG. 4D presents illustrative data relating to flow cytometric assessment of cell death in renal cell lines following 0.1 μM FLCN-10 treatment as determined by Annexin V/Propidium iodide staining.
FIG. 4E presents illustrative data relating to flow cytometric assessment of cell death in renal cell lines following 1.0 μM FLCN-10 treatment as determined by Annexin V/Propidium iodide staining.

Referring now to FIGS. 4A to 4E, it is shown that FLCN peptide induces apoptosis in cancer cell lines. FIG. 4A relates to endogenous LDHA immunoprecipitated from renal cell lines. Interaction with FLCN was observed by immunoblot. FIG. 4B relates to Caki-1 cells treated with FLCN-10 blotted for cleaved PARP and pTyr10-LDHA. FIG. 4C relates to flow cytometric assessment of cell death in renal cell lines following 1 µM FLCN-10 after one or two hours treatment as determined by Annexin V/Propidium iodide staining. FIG. 4D relates to flow cytometric assessment of cell death in renal cell lines following 0.1 µM or FIG. 4E 1 µM FLCN-10 treatment as determined by Annexin V/Propidium iodide staining.

Referring to FIG. 5 a Western blot of siRNA knockdown of FLCN for FIG. 1E.

Figures 6A, 6B:
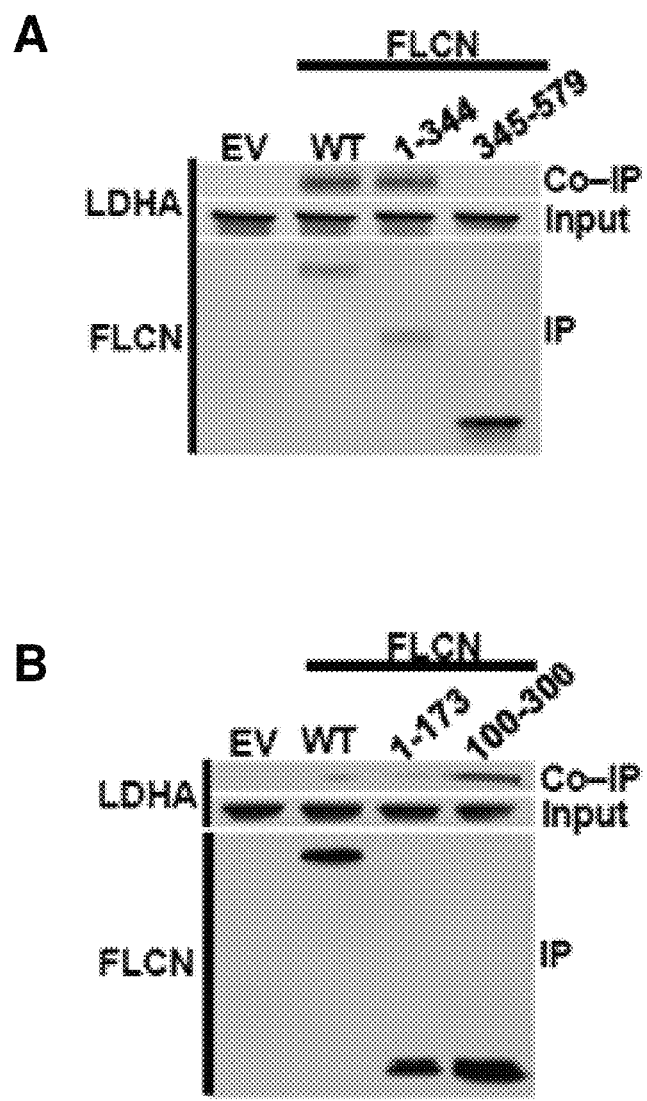
FIGS. 6A, 6B, 6C and 6D relate to immunoprecipitation of transiently expressed small segments of FLCN-FLAG protein demonstrates the critical interacting region with LDHA.
Figures 6C, 6D:
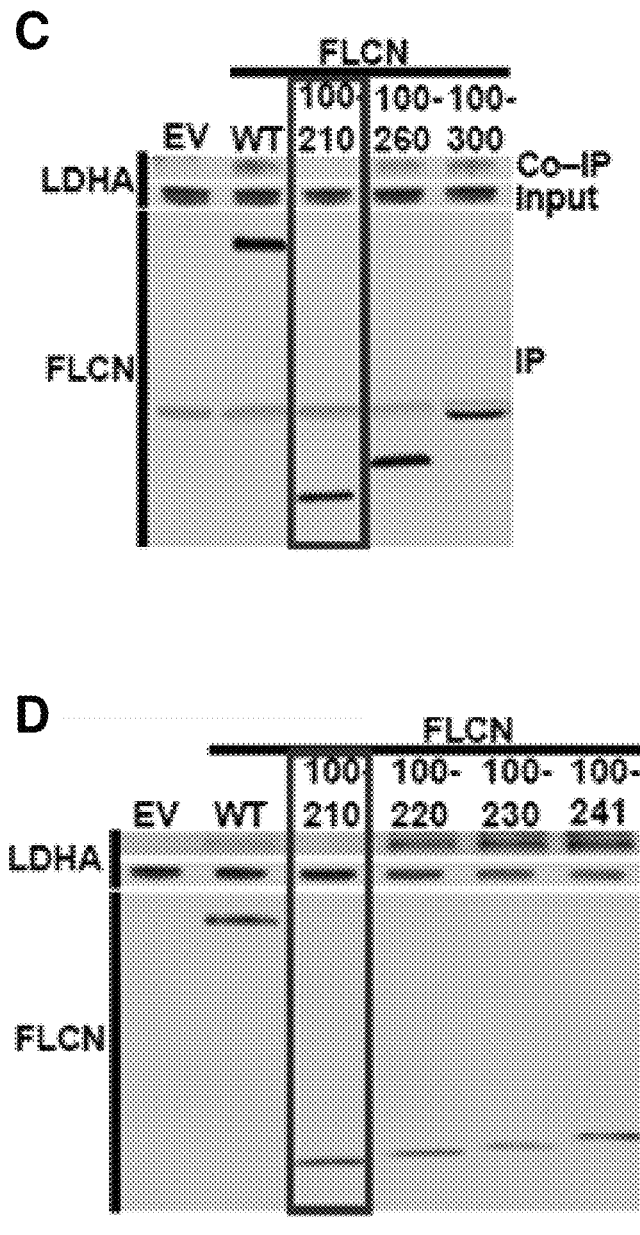
Figure 6E:
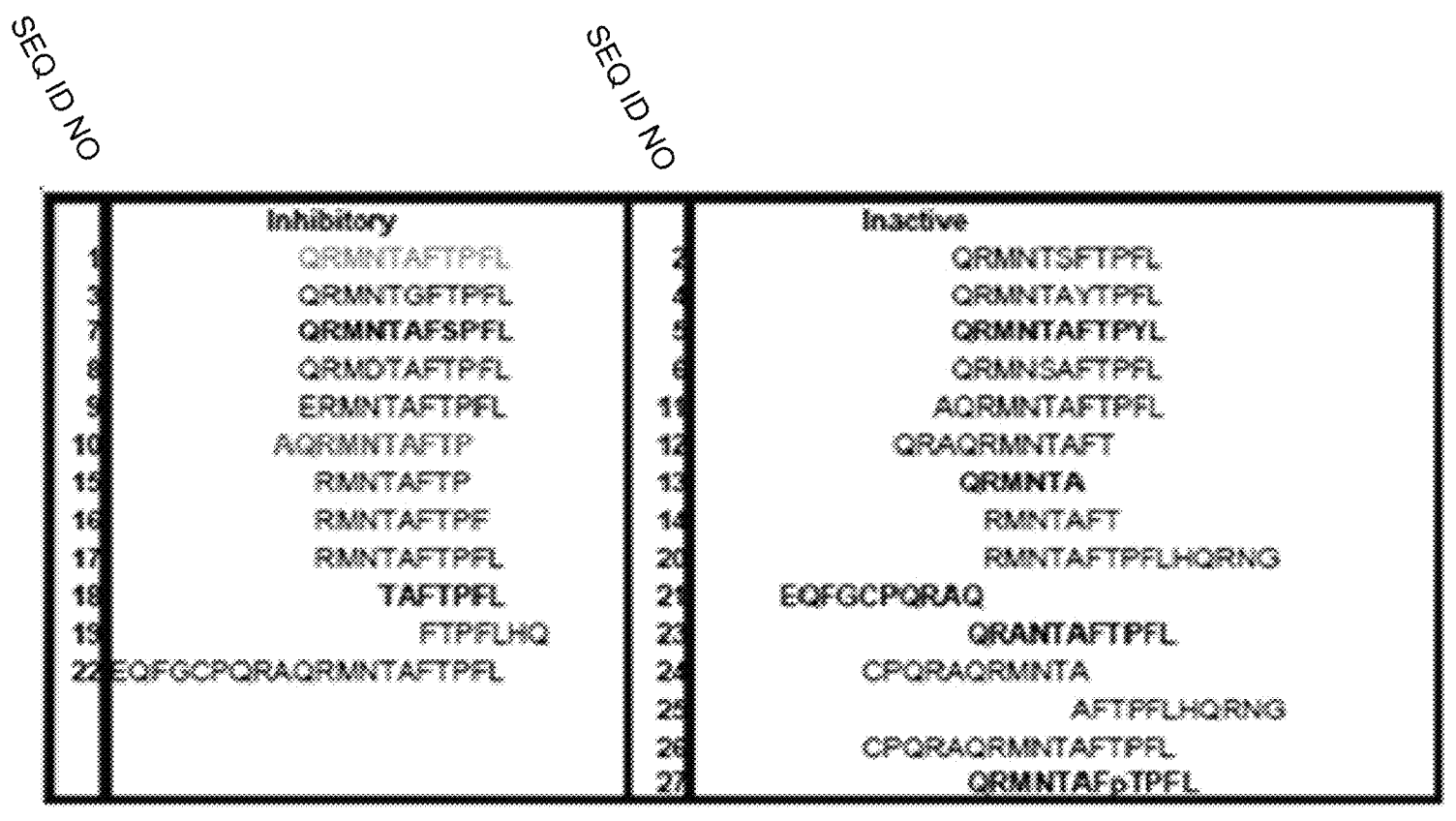
Figures 6F, 6G, 6H:
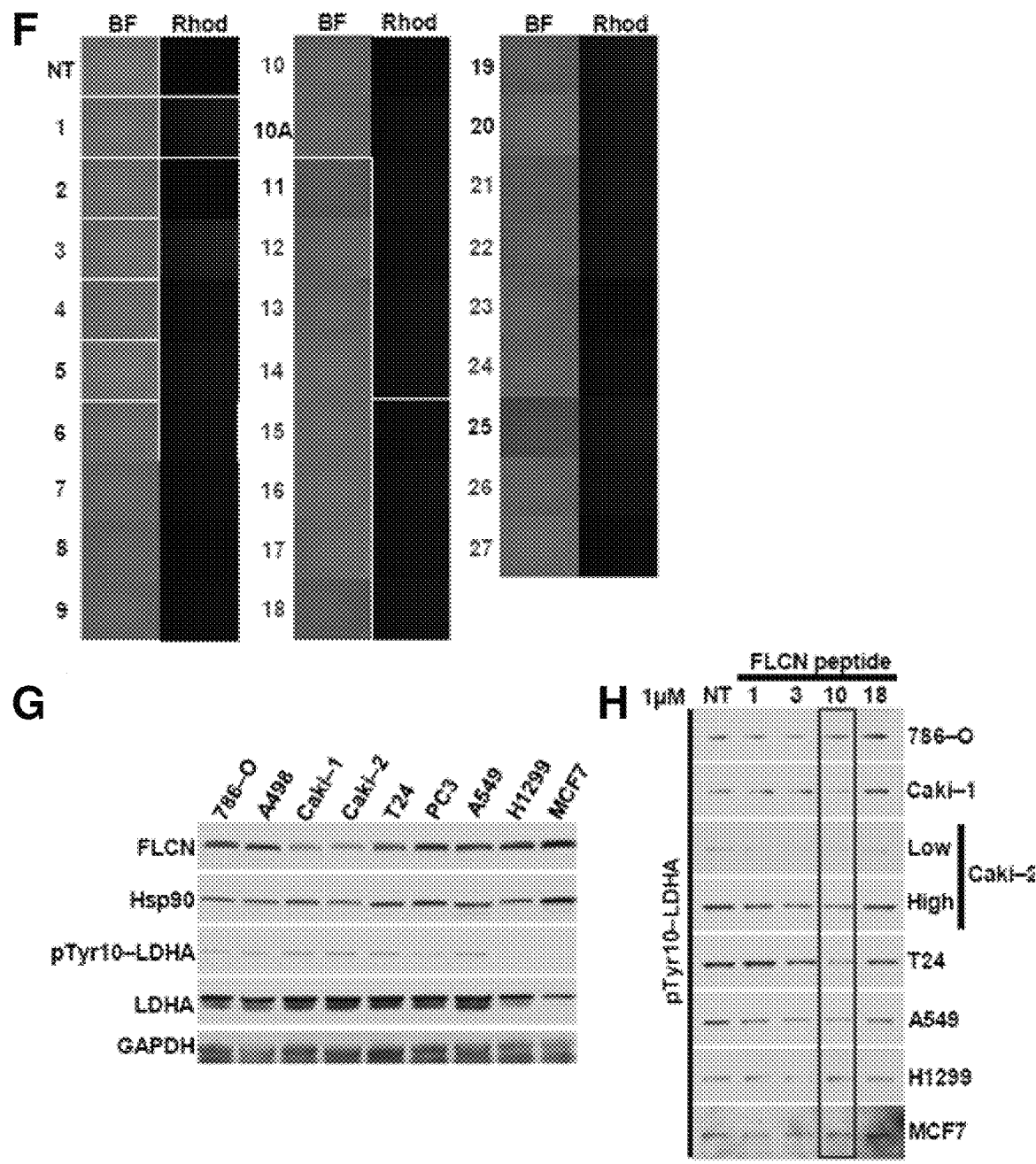
FIG. 6F presents illustrative data relating to HEK293 cells were treated with peptides from FIG. 2C at 1 μM.
FIG. 6G presents illustrative data relating to a panel of cancer cell lines immunoblotted to observe levels of endogenous FLCN and pTyr10-LDHA.
FIG. 6H presents illustrative data relating to cell lines from FIG. 6G treated with candidate FLCN peptides and immunoblotted for pTyr10-LDHA.
Figure 6I:
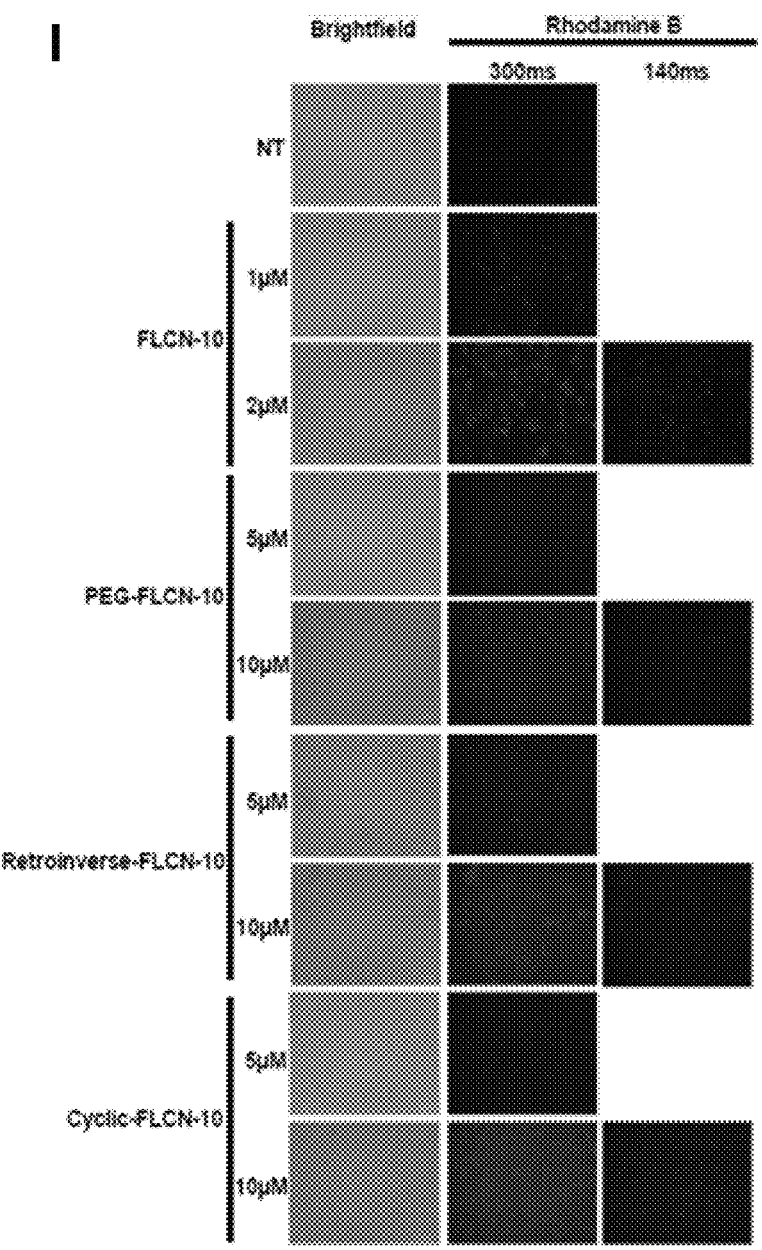
FIG. 6I presents illustrative data relating to rhodamine labeled, modified FLCN-10 peptides added to Caki-1 cells.
Figure 6J:
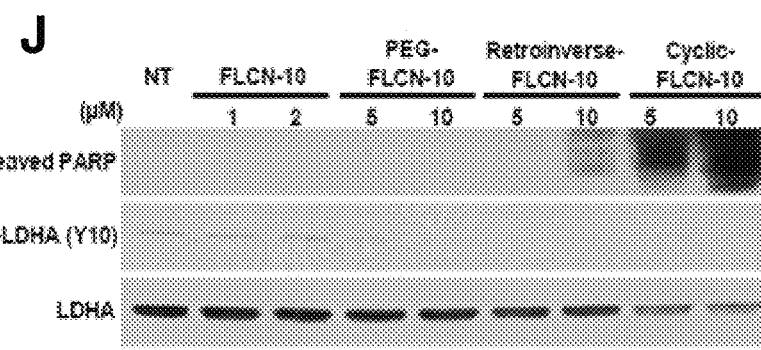
FIG. 6J presents illustrative data relating to Western blot of peptide treatments showing inhibition of LDHA activity and induction of apoptosis in Caki-1 cells.

Referring now to FIGS. 6A-6J. FIGS. 6A-6D show immunoprecipitation of transiently expressed small segments of FLCN-FLAG protein demonstrates the critical interacting region with LDHA. FIG. 6E lists peptides screened for $K_a$ or ability to inhibit LDHA. Peptides that inhibit LDHA activity in vitro are in the left column; those that do not are in the right column. Peptides that bind tightly to recombinant LDHA are in bold. Peptides in this figure include: 1—QRMNTAFTPFL (SEQ ID NO: 1), 2—QRMNTSFTPFL (SEQ ID NO: 2), 3—QRMNTGFTPFL (SEQ ID NO: 3), 4—QRMNTAYTPFL (SEQ ID NO: 4), 5—QRMNTAFTPYL (SEQ ID NO: 5), 6—QRMNSAFTPFL (SEQ ID NO: 6), 7—QRMNTAFSPFL (SEQ ID NO: 7), 8—QRMDTAFTPFL (SEQ ID NO: 8), 9—ERMNTAFTPFL (SEQ ID NO: 9), 10—AQRMNTAFTP (SEQ ID NO: 10), 11—AQRMNTAFTPFL (SEQ ID NO: 11), 12—QRAQRMNTAFT (SEQ ID NO: 12), 13—QRMNTA (SEQ ID NO: 13), 14—RMNTAFT (SEQ ID NO: 14), 15—RMNTAFTP (SEQ ID NO: 15), 16—RMNTAFTPF (SEQ ID NO: 16), 17—RMNTAFTPFL (SEQ ID NO: 17), 18—TAFTPFL (SEQ ID NO: 18), 19—RMNTAFTPFLHQRNG SEQ ID NO: 19), 20—FTPFLHQ (SEQ ID NO: 20), 21—EQFGCPQRAQ (SEQ ID NO: 21), 22 EQFGCPQRAQRMNTAFTPFL (SEQ ID NO: 22), 23—QRANTAFTPFL (SEQ ID NO: 23), 24—CPQRAQRMNTA (SEQ ID NO: 24), 25—AFTPFLHQRNG (SEQ ID NO: 25), 26—CPQRAQRMNTAFTPFL (SEQ ID NO: 26), 27—QRMNTAFpTPFL (SEQ ID NO: 27). Referring to FIG. 6F, HEK293 cells were treated with peptides from FIG. 2C at 1 µM, and were scored using a binary system denoting presence or absence of cellular localization of Rhodamine B fluorescence. Peptide that are resident after two hours treatment are denoted with a red number. Referring to FIG. 6G, a panel of cancer cell lines were immunoblotted to observe levels of endogenous FLCN and pTyr10-LDHA. Referring to FIG. 6H, cell lines from (sample of FIG. 6G) were treated with candidate FLCN peptides and immunoblotted for pTyr10-LDHA. In FIG. 6I, rhodamine labeled, modified FLCN-10 peptides were added to Caki-1 cells. Cell penetrance was assessed by fluorescence microscopy. Referring to FIG. 6J, Western blot of peptide treatments from (FIG. 6I) showing inhibition of LDHA activity and induction of apoptosis in Caki-1 cells.

Figure 7A:
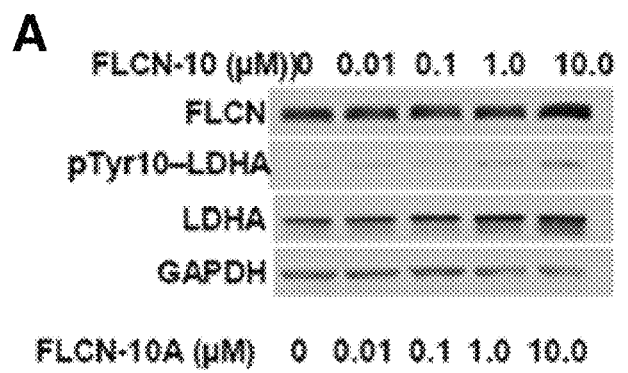
FIG. 7A presents illustrative data relating to dose response of pTyr10-LDHA after treatment with FLCN-10A peptide and FIG. 7B presents illustrative data relating to Western blot confirming transfection of FLCN-WT-FLAG and FLCN-M222A-FLAG in UOK257 cells in FIGS. 3C-D.
Figure 7B:
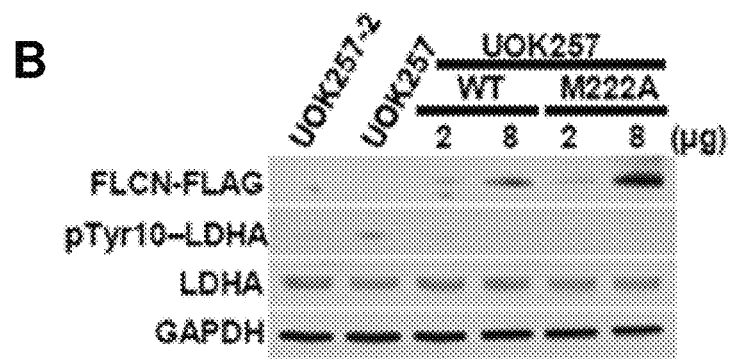

Referring to FIGS. 7A-7B, FIG. 7A relates to a response of pTyr10-LDHA after treatment with FLCN-10A peptide. FIG. 7B relates to Western blot confirming transfection of FLCN-WT-FLAG and FLCN-M222A-FLAG in UOK257 cells in FIGS. 3C-D.

Figure 8A:
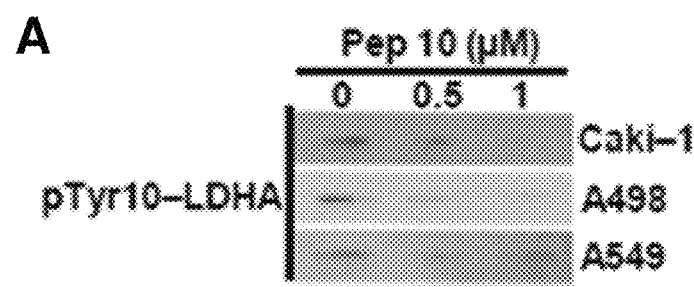
FIG. 8A presents illustrative data relating to dose response of pTyr10-LDHA in selected cancer cell lines after treatment with FLCN-10 peptide and FIG. 8B presents illustrative data relating to PC3 cells treated with FLCN-10 and immunoblotted to observe induction of apoptosis and inhibition of LDHA activity.
Figure 8B:
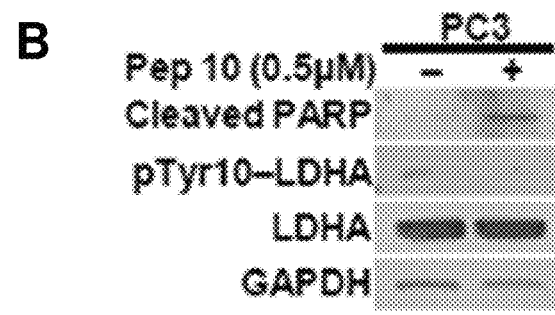

Referring to FIG. 8A-8B. FIG. 8A shows a dose response of pTyr10-LDHA in selected cancer cell lines after treatment with FLCN-10 peptide. FIG. 8B shows PC3 cells treated with FLCN-10 were immunoblotted to observe induction of apoptosis and inhibition of LDHA activity.

FLCN-Derived Peptides are Sufficient to Inhibit LDHA Activity.

To determine the region of FLCN necessary for binding to LDHA, the inventors constructed, transiently expressed and immunoprecipitated a series of FLCN truncation mutants using anti-FLAG agarose and binding to LDHA was assessed by immunoblotting. It was identified amino acids 100-220 within FLCN to be essential for interaction with LDHA (FIG. 6A-6D). The sequence of this region is represented schematically in FIG. 2A. This finding was supported by BS3 crosslinking data, which yielded a crosslink in the region of FLCN between residues 204-221 (FIG. 2B). Upon identifying the approximate binding region for LDHA on FLCN, the inventors made a series of peptides including addition or removal of upstream or downstream amino acids, point mutations, and post-translational modifications (FIG. 2C). The inventors demonstrated that peptide 10 (FLCN-10) (SEQ ID NO: 10) bound tightly to LDHA as determined by anisotropy (FIG. 2D), had a strong inhibitory effect on LDHA activity (FIG. 2E), and was cell permeant (FIG. 6F). This data is summarized by plotting $K_a$ against LDHA activity in FIG. 2F and in the table in FIG. 6E. The inventors also screened the four most effective peptides in vitro for activity against a panel of glycolytic tumor cell lines (FIG. 6G). Only FLCN-10 was capable of reducing LDHA activity (FIG. 6H).

Linear peptides, however, are notoriously unreliable as therapeutic effectors (Fosgerau K. et al., *Drug Discovery Today.* 2015; 20(1):122-8). In light of this, the inventors introduced modifications to the peptide to protect the peptide from digestion by cellular proteases. When normalized for amount of peptide residing in Caki-1 cells (FIG. 6I), the PEGylated FLCN-10 and retroinverse FLCN-10 peptides were effective at inhibiting LDHA activity, but showed minimal pro-apoptotic activity (FIG. 6J). The heterocyclic FLCN-10 peptide however, showed robust induction of apoptosis (FIG. 6J), suggesting cyclization is an effective packaging method for protecting this peptide while maintaining its activity.

The dye Cibacron blue 3GA (Cib) is often used for affinity purification of enzymes that contain NADH cofactor binding sites. LDHA binding to Cib-agarose was greatly diminished in HEK293 cells overexpressing FLCN, suggesting FLCN interference with the cofactor binding site on LDHA (FIG. 2G). This finding is supported by the FLCN:LDHA crosslinking data (FIG. 2B), as several critical residues for cofactor binding, including N168, R171, and T246 are all within or proximal to identified crosslinks. Additionally, R105 is within the catalytic loop of LDHA and it is important for its activity. Therefore, R105 was mutated to alanine, lysine, or glutamine and showed increased binding of these LDHA mutants to the wild-type FLCN (FIG. 2I). Additionally, streptavidin pulldown of a biotinylated analog of FLCN-10 demonstrated enhanced binding inactivated LDHA (FIG. 2I). These data suggest that FLCN possibly binds to inactive LDHA.

FLCN-10 inhibits LDHA in BHD cell lines and ex vivo patient tumors to identify the residues within the FLCN-10 peptide region that are important for binding to LDHA, the inventors made individual point mutations to FLCN-10. All residues were mutated independently to alanine with the exception of the two naturally-occurring alanine residues (positions 1 and 7), which were mutated to asparagine (FIG. 3A). Several mutations in FLCN appear to completely abrogate binding to LDHA, including R221A, F226A and P228A (FIG. 3B). Interestingly, the M222A mutation greatly increased the binding of FLCN to LDHA (FIG. 3B). Another peptide, FLCN-10A, was generated with the same M222A substitution. This peptide was unable to enter cells and thus had no activity against LDHA in Caki-1 cells (FIG. 7A). The inventors examined this mutant further by expressing two different amounts of FLCN-WT-FLAG and FLCN-M222A-FLAG in the UOK257 cell line (FIG. 7B), which was established from a BHD patient and lacks a functional copy of FLCN (Preston R S. et al., *Oncogene.* 2011; 30(10):1159-73). Transient transfection of 2 µg FLCN-WT or FLCN-M222A had little effect on extracellular acidification rate (ECAR), as measured on a Seahorse XFe96 Bioanalyzer. However, expression of 8 µg of either construct reduced ECAR to a similar level as the FLCN-replaced control cell line, UOK257-2 (FIG. 3C). In a parallel experiment, the inventors collected lysates from these transfections to assess their LDH activity. The inventors observed a comparable decrease in LDH activity upon transfection of 2 µg of FLCN-WT, and a significant reduction in LDH activity upon transfection of 2 µg FLCN-M222A (FIG. 3D). This inhibition in LDH activity is similar to that achieved by expressing 8 µg of FLCN-WT (FIG. 3D), suggesting a much greater inhibitory effect of FLCN-M222A on LDHA. This finding is consistent with the increased binding of FLCN-M222A to LDHA observed in FIG. 3B. The inventors' data showed that FLCN-10 peptide is cell permeable. Therefore FLCN-deficient tumor tissue and adjacent normal tissue were ex vivo treated with FLCN-10 peptide. The data revealed that FLCN-10 peptide is able to penetrate both normal and tumor tissues, and LDHA inhibition is evident by both immunofluorescence (FIG. 3E) and immunoblot (FIG. 3F). Taken together, the inventors identified a decapeptide within the amino-domain of FLCN that is able to enter the cancer cells and selectively inhibit LDHA activity.

Loss of FLCN-Mediated LDHA Inhibition in Renal Cell Carcinoma

In addition to FLCN-deficient tumors, the inventors sought to discern whether loss of LDHA control by FLCN was common to other Warburg-shifted cancers. One of the most common types of glycolytic cancers is clear cell renal cell carcinoma (ccRCC). The inventors found that FLCN expression levels are somewhat lower in ccRCC than HEK293 control cells and that these cell lines demonstrate LDHA hyperactivity (FIG. 4A). Immunoprecipitation of endogenous LDHA from these cells lines demonstrates FLCN dissociation from LDHA in ccRCC (FIG. 4A). Indeed an inverse correlation can be seen between LDHA activity and FLCN interaction (FIG. 4A). The inventors then sought to understand the consequence of inhibition of LDHA in these cancer cells. Treatment of ccRCC cell lines with FLCN-10 peptide (SEQ ID NO: 10) led to reduction of LDHA activity and induction of apoptosis after two hours as evidenced by cleavage of poly (ADP-ribose) polymerase (FIG. 4B). This effect was not observed in control HEK293 cells, however it was supported by similar observations in PC3 prostate cancer cells and A549 lung cancer cells (FIGS. 4C, and 8A-8B). Further, FLCN-10 peptide induced early apoptosis in a time- and dose-dependent manner in ccRCC, but not HEK293 cells, as evidenced by increase Annexin V staining (FIG. 4D-E).

Collectively, the data presented here demonstrate that FLCN functions as a bona ide endogenous inhibitor of LDHA. It was also discovered that endogenous FLCN does not bind and inhibit LDHA in cancer cells undergoing the Warburg effect. A small decapeptide within the amino-domain of FLCN is cell permeable and sufficient to inhibit LDHA, and therefore causes apoptosis in metabolically shifted cancer cells. Although the present disclosure has been described with respect to one or more particular embodiments and/or examples, it will be understood that other embodiments and/or examples of the present disclosure may be made without departing from the scope of the present disclosure.

Example 2

Methods
Mass Spectrometry

FLCN was immunoprecipitated from whole cell lysate, subjected to SDS-PAGE and stained with Imperial Protein Stain (ThermoFisher). Visible bands were digested in-gel with trypsin overnight at 37° C. following reduction with dithiothreiotol and alkylation with iodoacetamide. Mass spectrometry was performed at the Weill Cornell Medicine (WCM) Meyer Cancer Center Proteomics & Metabolomics Core Facility. The digests were vacuum centrifuged to near dryness and desalted by C18 Stage-tips. A Thermo Fisher Scientific EASY-nLC 1000 coupled on-line to a Fusion Lumos mass spectrometer (Thermo Fisher Scientific) was used. Buffer A (0.1% FA in water) and buffer B (0.1% FA in 100% ACN) were used as mobile phases for gradient separation. A 75 µm×20 cm column (ReproSil-Pur C18-AQ, 3 µm, Dr. Maisch GmbH, German) was packed in-house for peptide separation. Peptides were separated with a gradient of 3-32% buffer B over 50 min, 32%-80% B over 10 min at a flow rate of 300 nL/min. The Fusion Lumos mass spectrometer was operated in data dependent mode. Full MS scans were acquired in the Orbitrap mass analyzer over a range of 300-1500 m/z with resolution 60,000 at m/z 200. The top 15 most abundant precursors with charge states between 2 and 6 were selected with an isolation window of 1.4 Thomsons and fragmented by higher-energy collisional dissociation with normalized collision energy of 35. MS/MS scans were acquired in the Orbitrap mass analyzer with resolution 15,000 at m/z 200. The automatic gain control target value was 1e6 for full scans and 5e4 for MS/MS scans respectively, and the maximum ion injection time was 50 ms for both. The raw files were processed using the MaxQuant[33] computational proteomics platform version 1.5.5.1 (Max Planck Institute, Munich, Germany) for protein identification. The fragmentation spectra were used to search the UniProt human protein database (downloaded Sep. 21, 2017). Oxidation of methionine and protein N-terminal acetylation were used as variable modifications for database searching. The precursor and fragment mass tolerances were set to 7 and 20 ppm, respectively.

Both peptide and protein identifications were filtered at 1% false discovery rate based on decoy search using a database with the protein sequences reversed.

Limited Proteolysis Mass Spectrometry

Limited proteolysis was achieved by exposing recombinant LDHA (10 ng/μl)+/−FLCN-10 peptide (10 μM) to 20 μg/ml trypsin in 25 mM ammonium bicarbonate solution. At intervals of 5, 10, 15, 30, and 60 mins, 30 μL of the combined protein/trypsin solution was transferred to a second tube with 6 μL of SDS gel buffer and then boiled. This resulting partial-proteolyzed mixture was then run on an SDS-PAGE gel and stained with Coomassie Brilliant Blue. The selected protein gel bands were excised and in-gel digested with trypsin (0.6 μg) and the tryptic peptides were subjected to matrix-assisted laser desorption-ionization mass spectrometry (MALDI-MS) on an in-house ABSCIEX TOF/TOF® 5800 mass spectrometer. Positive mode time of flight was used to identify peptides, and individual peptides were sequenced by MS/MS. All sequence and peptide fingerprint data was searched using the UniProt database and Mascot search engine.

Cell Culture and Transfection

HAP1 cell lines were obtained from Horizon Discovery. UOK257 and UOK257-2 cell lines were provided by LSS. All other cell lines were obtained from the ATCC. Cells were cultured at 37° C. in a CellQ incubator at 5% $CO_2$. HEK293, Du145, J82, UMUC-3, MDA-MB-231, A549, UOK257 and UOK257-2 were grown in Dulbecco's Modified Eagle Medium (DMEM; Sigma-Aldrich), 786-0, PC3, SW780, LNCaP and H1299 were grown in Roswell Park Memorial Institute (RPMI 1640; Sigma-Aldrich), A498 were grown in Minimum Essential Medium (MEM; Sigma-Aldrich), Caki-1, Caki-2, HT29, T24, and RT4 were grown in McCoy's 5A Medium (Sigma-Aldrich), and HAP1 cells were grown in Isocove's Modified Dulbecco's Medium (IMDM; Gibco).

Plasmids and Transient Transfection

Plasmid information is available in the Key Resources Table. Cultured cells were transiently transfected using TransIT®-2020 (Mirus Bio) transfection reagent according to the manufacturer's protocol, incubated at 37° C. for 24 h (HEK293) or 48 h (UOK257, ccRCC cell lines) and subsequently prepared for protein extraction (see below). 50 μM control short interfering RNA (siRNA) or FLCN ON-TARGETplus siRNA (Dharmacon) were transiently transfected in LDHAKO or LDHB KO HAP1 cells for 48 h using TransIT®-2020. LDHA/LDHB chimeric constructs were synthesized by GeneWiz.

Protein Extraction, Immunoprecipitation, Pulldown and Immunoblotting.

Protein extraction from mammalian cells was carried out using methods previously described[34]. Tissues were homogenized with acid-washed glass beads and a mini-Beadbeater 8 (Biospec Products, USA). Samples were agitated for 30 s at maximum speed followed by a 30 s incubation on ice. This procedure was repeated 6× followed by a 10,000×g; 5 min centrifugation to pellet the beads and unbroken cells. The supernatant was transferred to a new microtube and centrifuged (10,000×g; 10 minutes) to pellet insoluble aggregates. The supernatant was then transferred to a fresh microtube. For immunoprecipitation, mammalian cell lysates were incubated with anti-FLAG or anti-HA antibody conjugated agarose beads (Sigma) for 2 h at 4° C., or with anti-LDHA or anti-FLCN antibody for 1 h followed by protein G agarose for 2 h at 4° C. For biotinylated peptide pulldown, lysates were incubated with biotinylated peptide for 1 h at 4° C., followed by incubation with streptavidin agarose for 1 h at 4° C. For Cibacron blue pulldown, mammalian cell lysates were incubated with Cibacron blue agarose for 1 h at 4° C. Immunopellets were washed 4 times with fresh lysis buffer (20 mM Tris-HCl (pH 7.4), 100 mM NaCl, 1 mM $MgCl_2$, 0.1% NP40, complete protease inhibitor cocktail (Millipore-Sigma), and PhosSTOP (Millipore-Sigma)) and eluted in 5× Laemmli buffer. Precipitated proteins were separated by SDS-PAGE and transferred to nitrocellulose membranes. Co-immunoprecipitated proteins were detected by immunoblotting with primary antibodies followed by secondary antibodies raised against mouse, rabbit, and rat (Cell Signaling) at 1:4000 dilution (See Key Resources Table). Densitometry was performed using Image Studio Lite (LI-COR Biosciences).

Native PAGE

Proteins were extracted as above. 5× sample loading buffer was prepared as follows: 250 mM Tris-HCl, pH 6.8, 30% glycerol, 0.05% bromophenol blue. Samples were incubated with sample buffer for 5 min at room temperature and loaded on a prepared Criterion Tris-HCl protein gel (Bio-Rad) in 1× native running buffer (25 mM Tris base, 192 mM glycine). Proteins were subjected to electrophoresis at 100V for 2 h and transferred to a nitrocellulose membrane with an RTA transfer kit according to manufacturer's protocol (Bio-Rad) using the standard 30 min transfer protocol on a TransBlot Turbo (Bio-Rad).

LDH Activity Assay

Lactate dehydrogenase activity was measured according to the manufacturer's protocol (MAK066, Sigma-Aldrich). In brief, 25 ng recombinant LDHA was pre-incubated with either peptide or recombinant FLCN protein for 30 min on ice. Samples were then transferred to an optically clear 96-well plate and substrate mix was added to each well. Absorbance was measured at 450 nm every five min until saturation. For measurement of LDH activity in lysates, 1 μg of whole cell lysate was diluted into 50 μl total volume with 1× assay buffer (included in MAK066) in a 96-well plate. Absorbance at 450 nm was measured every five min following addition of substrate mix.

All experiments were performed using three biological replicates and measured in triplicate.

LDHA Kinetics and Inhibition Assay

The effect of FLCN, FLCN-10 peptide, and FX11 (small molecule inhibitor of LDHA-control) on LDHA activity was examined in reactions previously published[35,36]. The reaction contains 50 mM Tris-HCl buffer (pH 7.0), 2 mM pyruvate, varied concentrations of NADH, and 2 nM FLCN or 100 nM FLCN-10 peptide, or 60 μM FX11. All assays were carried out in triplicate, and at least two independent assays were performed. Graphpad Prism 6 was used to calculate $IC_{50}$. Microsoft Excel was used to calculate kinetic parameters with appropriate nonlinear regression models, including Michaelis-Mention and allosteric sigmoidal models for substrates/cofactors. Only reaction data in the linear range were used in computations, which typically occurred within a reaction time of 5 min. The inhibitor constants ($K_i$) for FLCN, FLCN-10 peptide, and FX11 were calculated by Lineweaver-Burke plot and a web-based tool (://bioinfo-abcc.ncifcrf.gov/IC50_Ki_Converter/index.php) for converting $IC_{50}$ to $K_i$ values for inhibitors of enzyme activity and ligand binding[37].

Protein Purification

LCN and LDHA were cloned into pRSET-A (ThermoFisher) and expressed and purified from *E. coli* strain BL21 (DE3). Transformed cells were grown at 37° C. in LB with 50 mg/L ampicillin until the optical density measured at 600 nM reached 0.6. The cultures were then cooled to 30° C., induced with 1 mM IPTG, and grown overnight. Cells were harvested by centrifugation and lysed by sonication in fresh lysis buffer without detergent (20 mM Tris-HCl (pH 7.4), 100 mM NaCl, 1 mM $MgCl_2$, protease inhibitor cocktail (Millipore-Sigma) and PhosSTOP (Millipore-Sigma)).

After sonication, Triton X-100 was added to a final concentration of 1% prior to pelleting insoluble debris by centrifugation. Supernatant was collected and expression was assessed by immunoblotting. Isolation was accomplished by two sequential Ni-NTA agarose (QIAGEN) pull-downs. Lysate was incubated with Ni-NTA agarose (QIAGEN) for 2 h at 4° C. Proteins bound to Ni-NTA agarose were washed three times with lysis buffer (as above) followed by two washes with 50 mM imidazole in lysis buffer. Proteins were then eluted in 500 mM imidazole in lysis buffer and concentrated in 10K Amicon Ultra Centrifugal Filters (Millipore). Concentrations were determined using the Micro BCA Protein Assay Kit (Thermo Scientific) per manual protocol.

Purified protein was run on an SDS-PAGE gel and Coomassie stained to confirm purity prior to use in assays.

Ex Vivo Peptide Treatment

Tumor and adjacent normal renal tissue from the BHD patient were obtained with written informed consent on an Institutional Review Board (IRB)-approved protocol from the Department of Urology at SUNY Upstate Medical University. At the time of partial nephrectomy, which was done with <15 min of renal ischemia, BHD tumors were dissected into 3- to 5-mm$^3$ pieces and cultured on a pre-soaked gelatin sponge (Johnson & Johnson) in 24-well plates containing 2 ml RPMI-1640 with 10% FBS and antibiotic/antimycotic solution. Tissues were cultured at 37° C. for 16 h, followed by the addition of the indicated concentrations of FLCN-10-Rhod-B and further incubation at 37° C. for 2 h. Following treatment, tissues were either homogenized and lysed for immunoblotting (as above) or fixed in 10% formalin and paraffin embedded. Thin sections were mounted on slides and stained with hematoxylin and eosin or alternatively with anti-FLCN and anti-LDHA for immunofluorescence (below).

Fluorescence Microscopy

For peptide treatments: HEK293 cells were seeded on glass coverslips and grown overnight. The following day, cells were treated with Rhodamine B-labeled peptide for 2 h, followed by fixation in 4% paraformaldehyde for 15 min and mounted on slides using Prolong Gold Anti-fade reagent with DAPI (ThermoFisher). Images were obtained using Leica SP8 Confocal Microscope using LAS X software platform. Cells or thin tissue sections were fixed in 2% paraformaldehyde, permeabilized in 0.2% Triton X-100, and blocked for 2 h in 1% BSA at room temperature prior to staining. After several washes in 1×PBS, slides were incubated with primary antibodies to LDHA (sc-137243, Santa Cruz, 1:50) and FLCN (NBP1-44995, Novus Biologicals, 1:30) overnight at 4° C. Following several washes in 1×PBS, tissues were incubated with secondary antibodies Alexa Fluor® 594 and Alexa Fluor® 488 (Life Technologies) diluted in 1% BSA for 45 min at room temperature. Nuclear staining was achieved using ProLong® Gold antifade reagent with DAPI (Life Technologies). Representative images were captured on a Zeiss LSM710 Confocal Microscope (bar=20 μm).

Binding Measurements

LDHA at the indicated concentrations was incubated on ice in 50 mM Tris pH 7.2, 150 mM NaCl, 1 mM TCEP, 4 mM $MgCl_2$ with 1 mM Rhodamine-B-labeled FLCN peptide for 30 min. Fluorescence anisotropy was measured in triplicate using a SpectraMax i3 equipped with rhodamine fluorescence polarization module (lex\lem.535 nm/595 nm). Curve fitting was done in KaleidaGraph 4.0.

Seahorse Metabolic Assay

UOK cells were transfected in 100 mm dishes at 50% confluency and incubated for 24 h. Subsequently, cells were seeded at $10^5$/well 24 h prior to assay initiation in a 96-well plate and treated for the indicated times immediately preceding to measurement. A glycolytic stress test was then carried out on an Agilent Seahorse XF instrument according to the manufacturer's protocol.

Flow Cytometric Analysis

FACS analysis was performed according the protocol in the Annexin V:FITC kit (Bio-Rad). In brief, cells were plated at $0.5 \times 10^6$ and incubated at 37° C. for 16 h. Cells were subsequently treated with FLCN-10 peptide at indicated concentrations for 1-2 h. Cells were trypsinized, collected, and washed once with 1× binding buffer (included in kit). Annexin V-FITC was added at 1:40 and incubated for 10 min at room temperature in the dark. Following one wash with 1× binding buffer, propidium iodide was added and immediately run on a Becton Dickinson LSRFortessa (BD Biosciences). Data were analyzed using FlowJo software v0.6.2 (BD).

Linear Peptide Synthesis

Linear peptides (FIG. 10b) were synthesized and HPLC-purified to >95% purity by Life Technologies.

Peptide Synthesis: General Procedures (Extended Data FIG. 20a-e)

Resin Loading

Resin (0.5 mmol/g loading) was swollen in $CH_2Cl_2$ for 30 min then washed with DMF (3×3 ml). A solution of entering Fmoc-amino acid, DIC and Oxyme (5:5, 5 equivalents over resin loading) and 5% of DMAP in DMF (3 ml) was added and the resin shaken at RT for 4 h. The resin was washed with DMF (2×3 ml) and capping was performed by treatment with acetic anhydride/DIEA in DCM (1×30 min). The resin was then washed with DMF (2×3 ml), $CH_2Cl_2$ (2×3 ml), and DMF (2×3 ml). The resin was subsequently submitted to fully automated iterative peptide assembly (Fmoc-SPPS).

Peptide Assembly Via Iterative Fully Automated Microwave Assisted SPPS

Peptides were assembled by stepwise microwave-assisted Fmoc-SPPS on a Biotage ALSTRA Initiator+ peptide synthesizer, operating in a 0.1 mmol scale. Activation of entering Fmoc-protected amino acids (0.3 M solution in DMF) was performed using 0.5 M Oxyma in DMF/0.5 M DIC in DMF (1:1:1 molar ratio), with a 5 equivalent excess over the initial resin loading. Coupling steps were performed for 7 min at 75° C. Fmoc-deprotection steps were performed by treatment with a 20% piperidine solution in DMF at room temperature (1×10 min). Following each coupling or deprotection step, peptidyl-resin was washed with DMF (4×3.5 ml). Upon complete chain assembly, resin was washed with DCM (5×3.5 ml) and gently dried under a nitrogen flow.

Cleavage from the Resin

Resin-bound peptide was treated with an ice-cold TFA, TIS, water, thioanisole mixture (90:5:2.5:2.5 v/v/v/v, 4 ml). After gently shaking the resin for 2 h at room temperature, the resin was filtered and washed with neat TFA (2×4 ml). The combined cleavage solutions were worked-up as indicated below.

Work-Up and Purification

Cleavage mixture was concentrated under nitrogen stream and then added dropwise to ice-cold diethyl ether (40 ml) to precipitate the crude peptide. The crude peptide was collected by centrifugation and washed with further cold diethyl ether to remove scavengers. Residual diethyl ether was removed by a gentle nitrogen flow and the crude peptide was purified by RP-HPLC and lyophilized.

Peptide Cyclization

Peptides for head-to-tail cyclization were detached from the resin using 25% HFP in DCM (4×10 min). Collected fractions were combined and dried under reduced pressure. The residue was then dissolved in dry DMF (1.25 mM) and HBTU/DIEA were added (1.1, 2 eq. respectively). Reaction was let overnight and then DMF evaporated. The dry residue was then treated with standard TFA-based cleavage solution to yield the fully unprotected, cyclic peptides.

Synthesis of Fluorescein-Labelled Peptides

Cysteine-bearing peptides were conjugated to bifunctional MAL-FAM (Lumiprobe GmbH, Germany) as follows: peptide (1 eq.) was dissolved in phosphate buffer ($Na_2HPO_4$ 0.4 M, pH 7.8). The resulting solution was ice-cooled and mixed with MAL-FAM solution (1.2 eq., 50:50 acetonitrile/water mixture). The reaction mixture was left to react for under gentle shaking until full reagents conversion (RP-HPLC monitoring). Upon reaction completion, conjugation products were isolated by preparative RP-HPLC and lyophilized.

RP-HPLC Analysis and Purification

Analytical RP-HPLC was performed on a Shimadzu Prominence HPLC (Shimadzu) using a Shimadzu Shimpack GWS C18 column (5 micron, 4.6 mm i.d.×150 mm). Analytes were eluted using a binary gradient of mobile phase A (100% water, 0.1% trifluoroacetic acid) and mobile phase B (30% water, 70% acetonitrile, 0.1% trifluoroacetic) using the following chromatographic method: 10% B to 100% B in 14 min; flow rate, 1 ml/min. Preparative RP-HPLC was performed on a Shimadzu HPLC system using a Shimadzu C18 column (10 micron, 21.2 mm i.d.×250 mm) using the following chromatographic method: 0% B to 100% B in 45 min; flow rate, 14 ml/min. Pure RP-HPLC fractions (>95%) were combined and lyophilized.

Electro-Spray Ionization Mass Spectrometry (ESI-MS)

Electro-spray ionization mass spectrometry (ESI-MS) was performed using a Bruker Esquire 3000+ instrument equipped with an electro-spray ionization source and a quadrupole ion trap detector (QITD).

Quantification and Statistical Analysis

The data presented are the representative of three biological replicates, unless otherwise specified. All statistics were performed using GraphPad Prism version 7.00 for Windows (GraphPad Software, La Jolla, Calif., USA, www.graphpad.com). Statistical significance was ascertained between individual samples using a parametric unpaired t-test. Significance was denoted as asterisks in each figure: *$P<0.05$; $P<0.01$; *$P<0.001$; ****$P<0.0001$. Error bars represent the standard deviation (SD) for three independent experiments, unless otherwise indicated.

Data Availability

The mass spectrometry proteomics data have been deposited to the ProteomeXchange Consortium via the PRIDE partner repository with the dataset identifier PXD018410.

Novel Function of the Tumor Suppressor FLCN

Figure 9A:
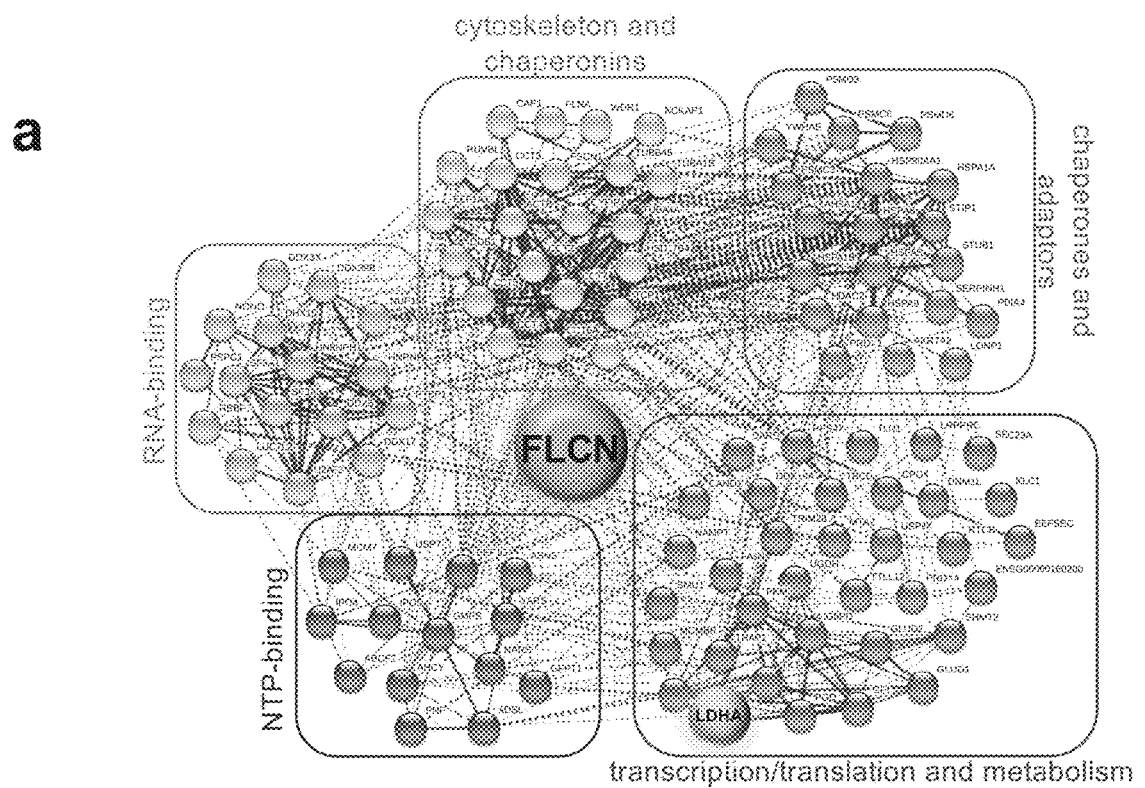
FIG. 9A presents illustrative data relating to FLCN-FLAG immunoprecipitated (IP) from HEK293 cells subjected to MALDI-TOF.
Figure 9B:
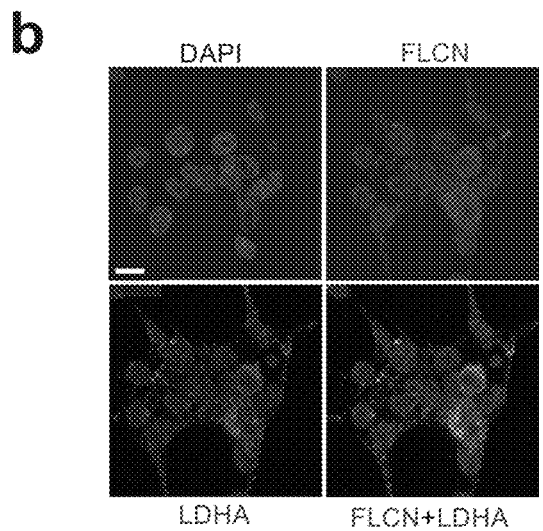
FIG. 9B presents illustrative immunoblotting data relating to embodiments of the present disclosure.

FLCN is a known tumor suppressor, however its exact function remains elusive[7,8]. Our proteomic approach using FLCN-6×His isolated from HEK293 cells identified 114 interacting proteins, including lactate dehydrogenase-A (LDHA) (see FIG. 9A). GO term enrichment analysis revealed that these FLCN binding partners primarily belong to cellular metabolic and RNA processing pathways (See FIG. 13A). The inventors confirmed the interaction with LDHA by immunoprecipitation (IP) of LDHA-FLAG and co-IP of endogenous FLCN (FIG. 13b). Immunofluorescence microscopy shows co-localization of FLCN and LDHA in HEK293 cells, further demonstrating the plausibility of this interaction (see FIG. 9B). Overexpression of FLCN perturbs the activity of LDHA, as evidenced by decreased intensity of the activation-coupled phospho-Tyr10-LDHA[9,10]. This suggests that FLCN interaction has a functional impact on LDHA activity (See FIG. 9C).

Figure 9C:
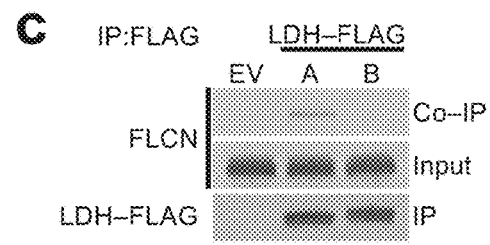
FIG. 9C presents illustrative data relating to IP of LDHA-FLAG or LDHB-FLAG expressed in HEK293 cells immunoblotted with anti-FLCN to assess interaction (Co-IP).
Figure 9D:
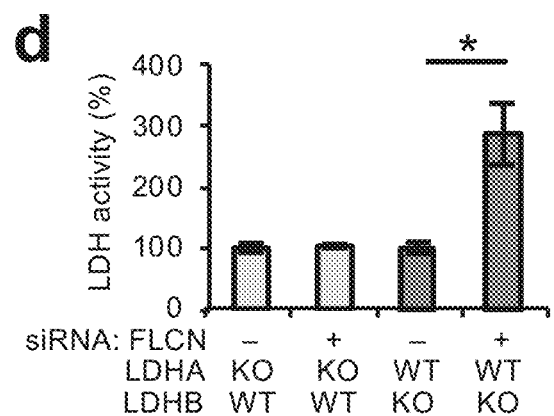
FIG. 9D presents illustrative data relating to LDH activity measured in vitro using whole cell lysates from LDHA or LDHB knockout HAP1 cells following treatment with siRNA targeting FLCN (n=3).
Figure 9E:
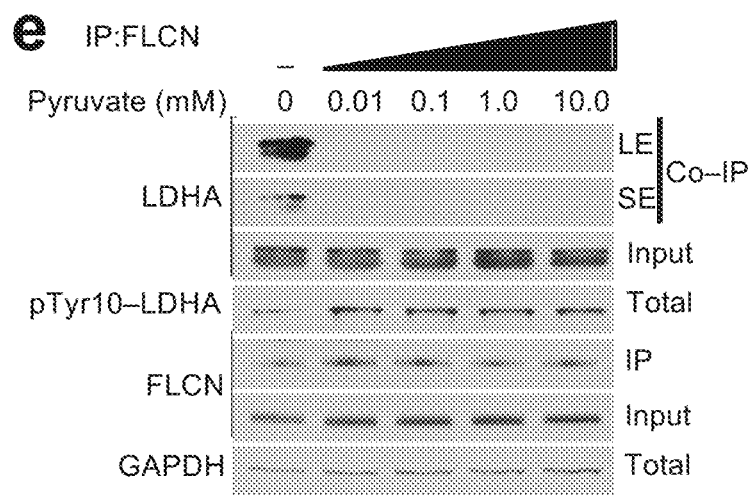
FIG. 9E presents illustrative data relating to immunoblot of anti-FLCN IPs and whole cell extracts following exogenous addition of pyruvate to HEK293s for 6 h (n=3). SE=short exposure, LE=long exposure.

LDHA and LDHB are highly conserved isoenzymes[11], and both are present endogenously in HEK293 cells. Interestingly, immunoprecipitation of LDHA- or LDHB-FLAG from whole cell lysate showed FLCN specifically bound to LDHA, but not LDHB (FIG. 9c). LDHA and LDHB form mixed tetrameric complexes described as a "dimer of dimers"[9,10,12,13]. Consecutive immunoprecipitation of co-expressed LDHA-HA/LDHA-FLAG or LDHA-HA/LDHB-FLAG demonstrated FLCN interaction with LDHA/LDHA homodimers but not LDHA/LDHB heterodimers (See FIG. 9D). The inventors further performed siRNA knockdown of FLCN in haploid HAP1 cells modified by CRISPR to express either LDHA or LDHB as the sole LDH (See FIG. 9E). Decreased FLCN expression in these cells enhanced the activity of LDHA, but not LDHB suggesting FLCN specifically regulates LDHA (FIG. 9D). To examine the selectivity of FLCN for LDHA further, the inventors developed chimeric constructs based on the concentration of natural sequence and structural variation in the first 22 (N) and last 38 (C) amino acids of LDHA and LDHB (See FIGS. 10A-B)[14]. Exchanging the LDHB N-domain or C-domain individually into LDHA preserved binding of FLCN (See FIG. 10C). Replacing both domains (NC), however, completely abrogated FLCN interaction, similar to wild-type LDHB (See FIG. 10C). These observations further reinforce the inherent specificity of FLCN for LDHA over LDHB.

Figure 9F:
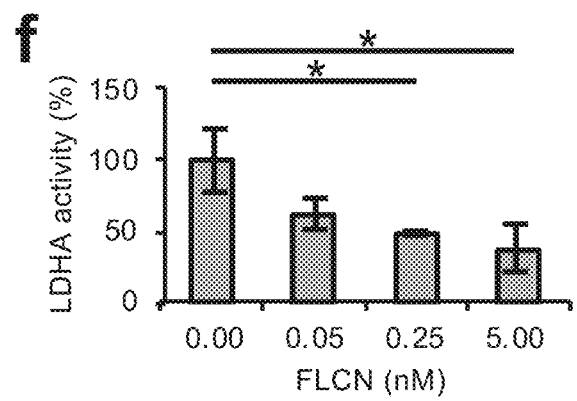
FIG. 9F relates to activity of 10 nM recombinant LDHA measured in the presence of increasing amounts of recombinant FLCN (n=3), wherein data shown as mean±s.d. *P<0.05.

Canonically, LDHA is activated in cells by pyruvate accumulation[15,16]. To evaluate whether the activation of LDHA is coupled to its dissociation from FLCN, the inventors treated HEK293 cells with supraphysiological doses of pyruvate. LDHA activation resulted in disruption of the FLCN-LDHA complex, as co-immunoprecipitation of LDHA with FLCN was only achieved in the absence of exogenous pyruvate (See FIG. 9E). Interestingly, addition of lactate had a much milder effect on dissociation of LDHA from FLCN (See FIG. 10D), consistent with LDHA preference for pyruvate as a substrate[17]. Pre-incubation of LDHA with recombinant FLCN also attenuates LDHA activity in vitro (see FIG. 9F), suggesting FLCN-LDHA interaction precludes substrate binding.

The inventors next examined the impact of FLCN on NADH cofactor binding to LDHA. NADH binding in the active site of LDHA is pre-requisite for substrate binding. The dye Cibacron blue 3GA (Cib) is often used for affinity purification of enzymes that contain NADH cofactor binding sites[18]. LDHA binding to Cib-agarose was greatly diminished in HEK293 cells overexpressing FLCN, suggesting FLCN interference with cofactor binding to LDHA (See FIG. 10E). Taken together, our data suggest that the tumor suppressor FLCN specifically binds to LDHA, but not LDHB[19], and inhibits its enzymatic activity. FLCN uncompetitively inhibits LDHA.

To determine the molecular mechanism of FLCN-mediated inhibition of LDHA, the inventors constructed, transiently expressed, and immunoprecipitated a series of FLCN truncation mutants in HEK293 cells. The inventors identified amino acids (aa) 210-220 within FLCN to be essential for interaction with LDHA (See FIGS. 15A-D). Based on the published cryo-EM structures, this region of FLCN falls within an unstructured loop positioned between two α-helices in the N-terminus (FIG. 10A)[20,21]. The inventors subsequently made a series of overlapping peptides including addition or removal of upstream or downstream amino acids, point mutations, and T227 phosphorylation beginning with aa 220-230, as these residues are definitively within the LDHA-binding region (FIG. 10B; See FIG. 15D). The inventors demonstrated that this peptide derived from aa220-230 (FLCN-1) bound tightly to LDHA ($K_a \approx 1 \times 10^7$; See FIG. 11E). Encouragingly, peptide-10 (FLCN-10; aa219-228) showed greatly enhanced binding (see FIG. 10C), had a strong inhibitory effect on LDHA activity (70%) (See FIG. 10D), and was cell permeant (see FIG. 16). This data is summarized in a plot of $K_a$ against LDHA activity (See FIG. 15F). Using traditional enzyme kinetics, the inventors further showed that FLCN-10 uncompetitively inhibits LDHA (See FIGS. 10E-F), and FIGS. 13A-B. Both full-length FLCN protein and FLCN-10 peptide also showed greatly improved potency as compared to the previously characterized LDHA inhibitor FX11[22] (See FIG. 17C-F). This binding and kinetic data has been summarized in FIG. 10G.

Limited proteolysis-coupled mass spectrometry (LiP-MS) is a technique by which proteolytic cleavage can be used to observe structural changes in a protein induced by small molecule interaction[23]. Upon digestion with trypsin, which cleaves after lysine and arginine residues, a complex of FLCN-10 peptide with full-length recombinant LDHA yielded one unique differential LDHA peptide corresponding to residues $^{91}$LVIITAGAR$^{99}$, that forms the N-terminal portion of the LDHA catalytic loop (FIG. 2h)[24]. Accessibility of the LDHA catalytic loop is likely altered as a result of allosteric effects on the active site secondary to FLCN binding; this is consistent with FLCN interference with cofactor (NADH) binding and uncompetitive inhibition of LDHA.

Based on the crystal structure of LDHA, arginine-106 is within its catalytic loop and is important for its activity, and mutation of R106 to alanine, lysine, or glutamine has been shown to restrict movement of the catalytic loop[25]. These mutants showed increased binding to FLCN (see FIG. 17G). Additionally, streptavidin pulldown of a biotinylated FLCN-10 analog demonstrated enhanced binding to these inactive LDHA mutants (See FIG. 17G). Therefore, the data suggest that FLCN binding can be modulated by changes in the LDHA active site.

Regulation of Glycolysis by FLCN

Figures 12A, 12B, 12C:
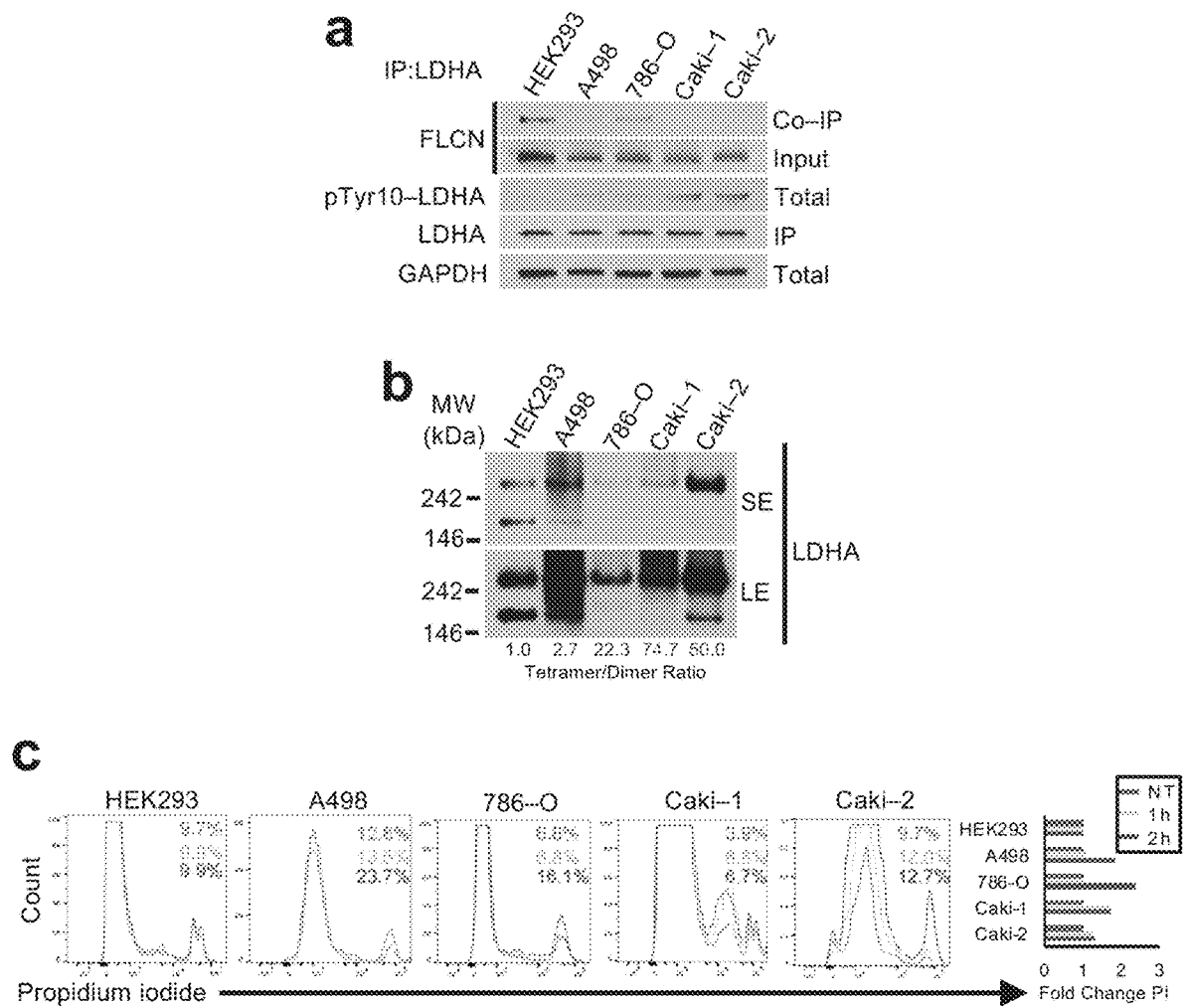
FIG. 12A presents illustrative data relating to endogenous anti-LDHA immunoprecipitation from renal cell lines.
FIG. 12B presents illustrative data relating to Native Western blot using anti-LDHA in renal cell lines. SE=short exposure, LE=long exposure.
FIG. 12C presents illustrative data relating to flow cytometric assessment of cell death in renal cell lines following treatment.

FLCN is a modular protein consisting of an N-terminal intrinsically disordered region (IDR), followed by two structured domains that are linked by a long IDR loop[20,21,26] The identified LDHA binding residues are located on this IDR loop comprised of residues 216-248 of FLCN (FIG. 12A). To gain further insight into the mechanism of FLCN binding and inhibition of LDHA, the inventors made a series of mutations within the FLCN-10 peptide region. Each residue was mutated independently to alanine with the exception of the two naturally-occurring alanines (A219 and A225), which were mutated to asparagine (FIG. 12b). Several mutations in FLCN appeared to completely abrogate binding to LDHA, including R221A, F226A and P228A (see FIG. 12c). Interestingly, the M222A mutation greatly increased the binding of FLCN to LDHA (See FIG. 12C), however the corresponding FLCN-10A peptide, with the same M222A substitution, was cell impermeable and had no activity against LDHA in Caki-1 cells (See FIG. 18A-18B).

Birt-Hogg-Dubé (BHD) syndrome is caused by mutation and inactivation of FLCN and predisposes patients to renal cell carcinoma[27]. The inventors examined the function of the FLCN-M222A mutant by expressing two different amounts of FLCN-WT-FLAG and FLCN-M222A-FLAG in the UOK257 cell line (Extended Data FIG. 6c), which is a FLCN-null cell line established from a patient with BHD syndrome[5,28]. Transient transfection of 2 μg FLCN-WT or FLCN-M222A plasmid had little effect on extracellular acidification rate (ECAR), a measure of glycolytic flux (See FIG. 18D). However, transfection of 8 μg of either construct reduced ECAR to a similar level as the FLCN-replaced control cell line, UOK257-2 (See FIG. 11D, and See FIG. 18d).

Figures 11A, 11B, 11C, 11D, 11E:
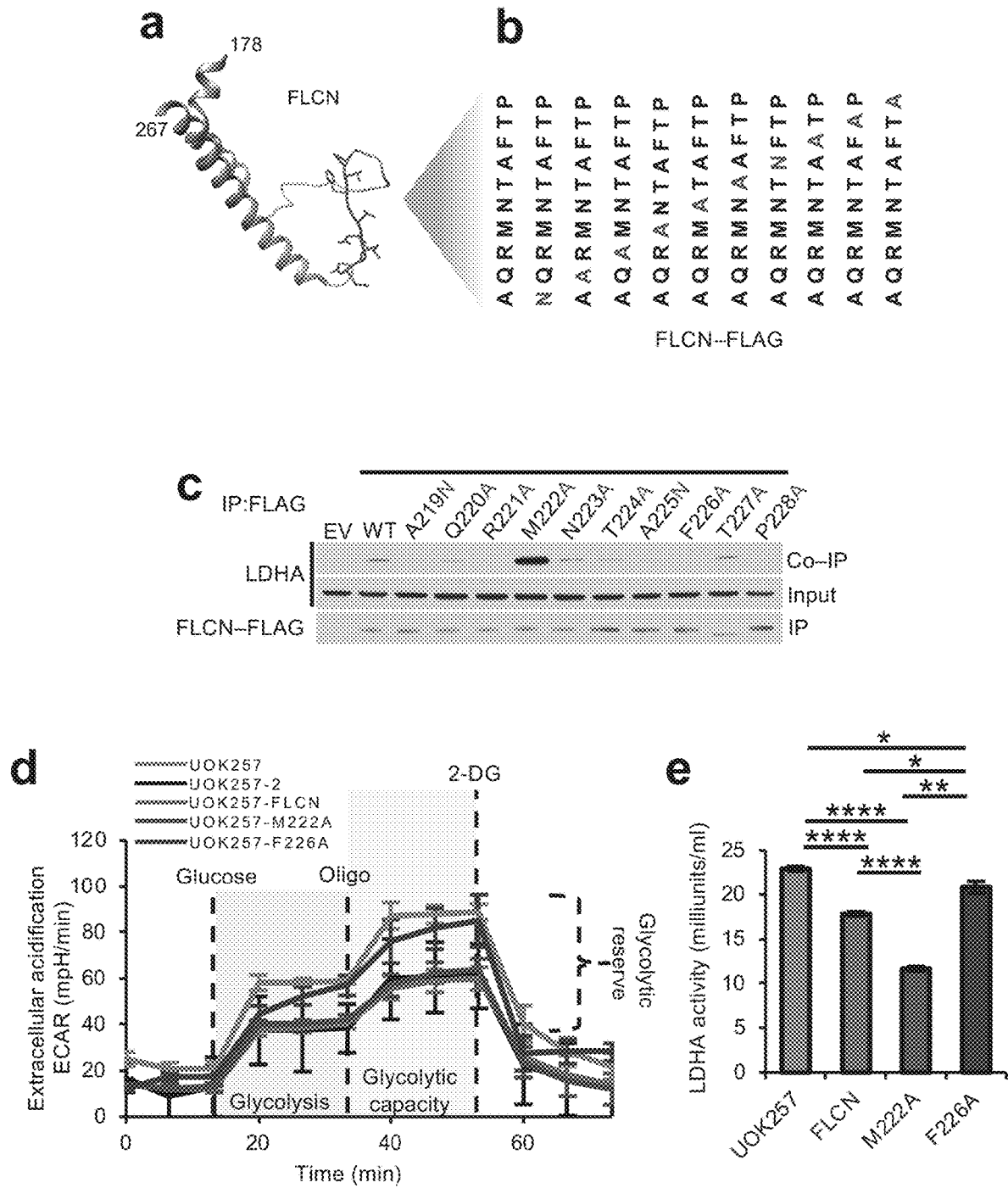
FIG. 11A depicts structure of FLCN flexible loop with flanking α-helices (aa 178-267). Unstructured loop region is highlighted in orange, FLCN-10 peptide region with sidechains displayed in red (PDB ID: 6ulg).
FIG. 11B depicts various amino acid mutations in FLCN-10 residues (blue).
FIG. 11C depicts point mutations within the FLCN peptide region that were transiently expressed in HEK293 cells and immunoprecipitated. Interaction with LDHA (Co-IP) was assessed by immunoblot.
FIG. 11D illustrative data relating to extracellular acidification rate of UOK257 cells transfected with 8 µg of WT FLCN, M222A or F226A mutants (n=6).
FIG. 11E presents illustrative data relating to LDH activity of lysates collected from c (n=3).
Figures 18A, 18B, 18C, 18D:
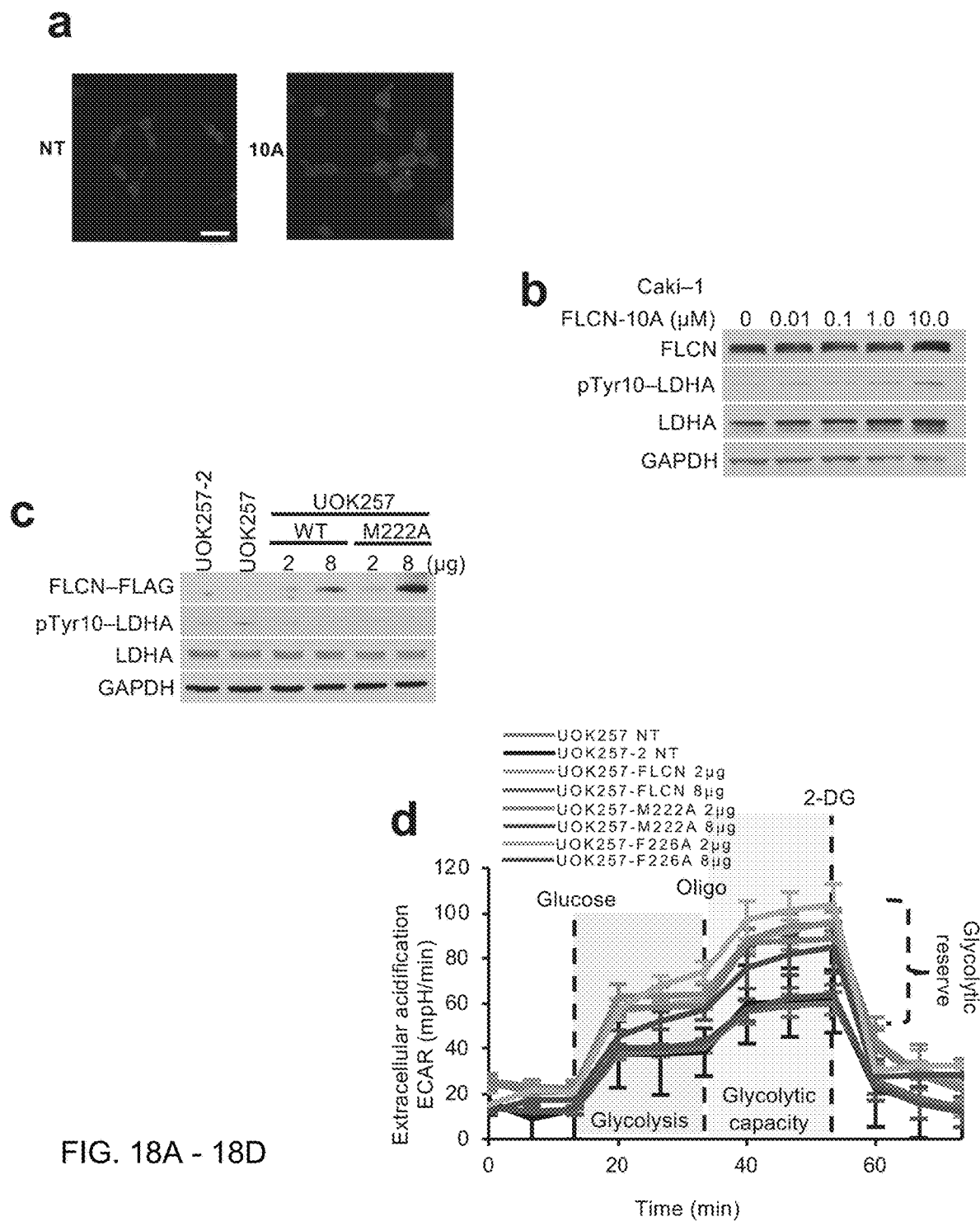
Figures 18E, 18F, 18G:
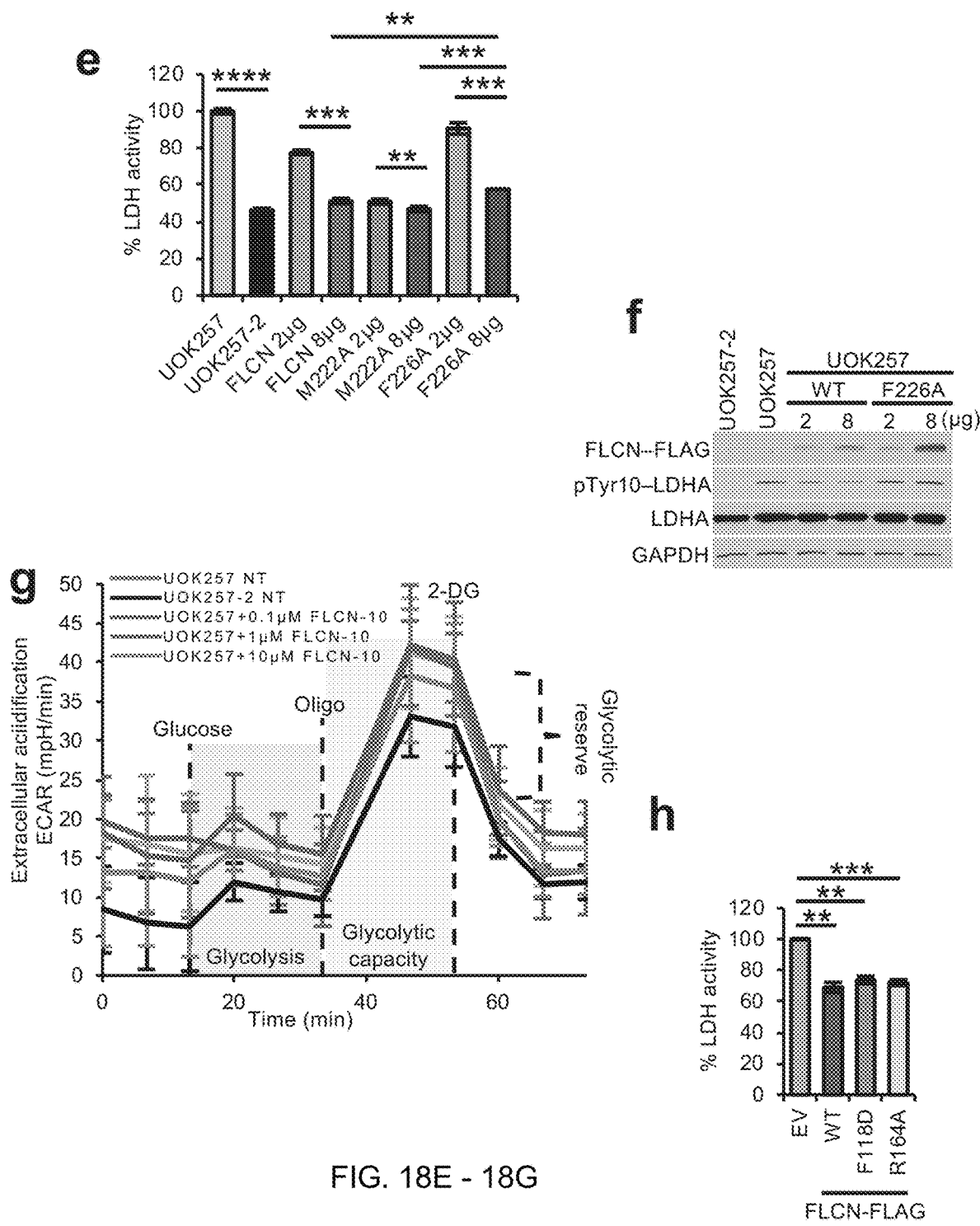

In parallel, the inventors collected lysates from these transfections to assess their LDH activity. The inventors observed a decrease in LDH activity upon transfection of 2 μg of FLCN-WT, and a statistically significant further reduction in LDH activity upon transfection of 2 μg FLCN-M222A (P<0.0001; FIG. 11e). This decreased LDH activity is similar to that achieved by expressing 8 μg of FLCN-WT (See FIG. 18E), suggesting a much greater inhibitory effect of FLCN-M222A. These results were reinforced by the FLCN-F226A mutation, which instead lacked interaction with LDHA and, subsequently had minimal effect on ECAR and inhibited LDHA activity less than WT FLCN (FIG. 11C-E; FIGS. 18D-F). Together, the M222A and F226A mutants demonstrated that the inhibitory function by FLCN on LDHA correlates with FLCN:LDHA binding affinity in cells. The inventors then asked whether FLCN-10 peptide was also capable of modulating ECAR in UOK257 cells. Indeed, a modest decrease in ECAR was observed following treatment with FLCN-10 peptide (See FIG. 18G).

Figure 16:
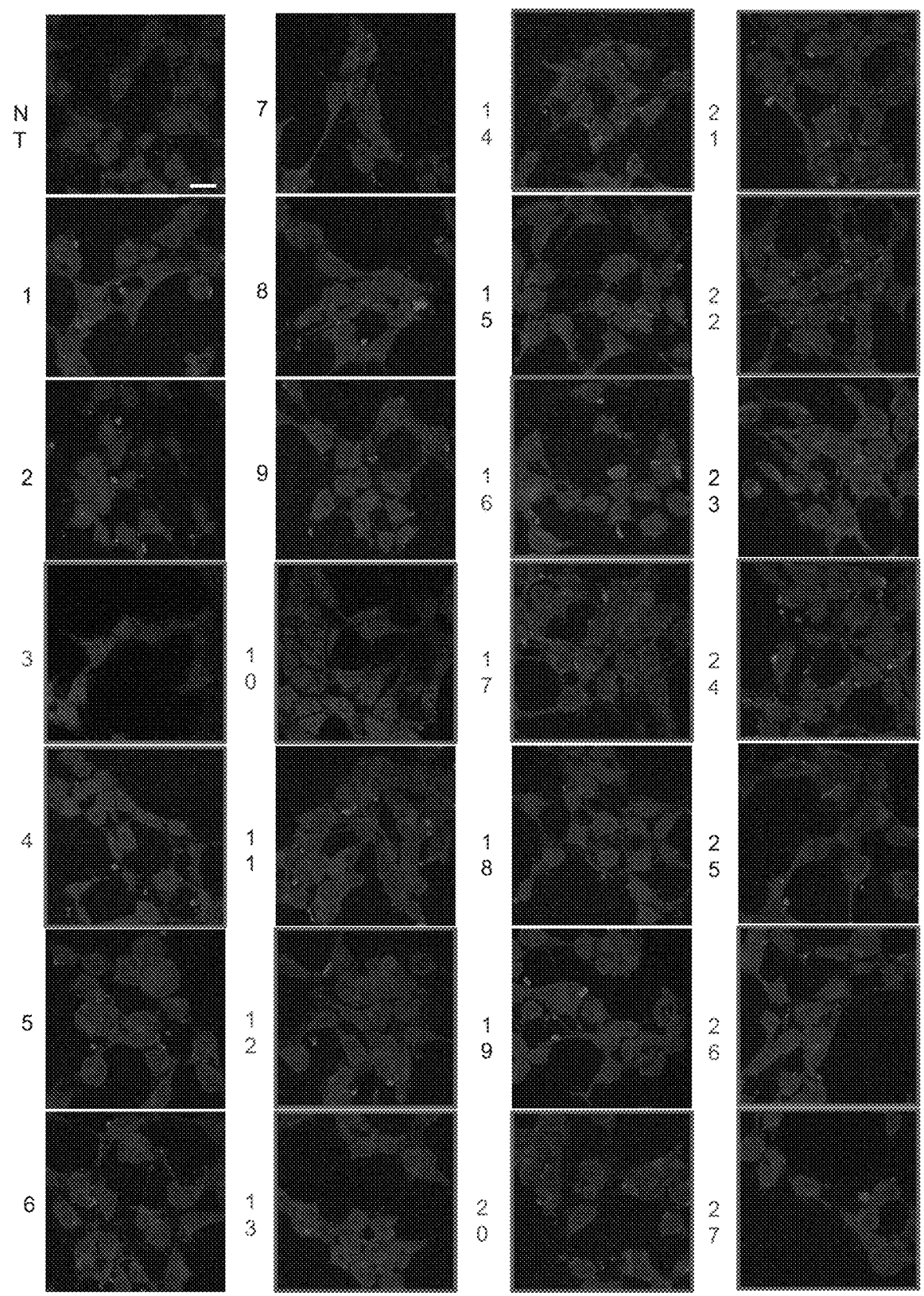
FIG. 16 depicts fluorescence microscopy data of HEK293 cells treated as described below.

Recent reports have demonstrated the role of FLCN-F118 in assembly of the Ragulator complex[21] and FLCN-R164 in the GAP activity of FLCN[20], both of which are outside of the identified LDHA binding region. Neither FLCN-F118D nor R164A mutation affected the FLCN-mediated inhibition of LDHA in HEK293 cell lysates, suggesting exclusivity of these reported FLCN functions (See FIG. 18H). Our data showed that FLCN-10 peptide is cell permeable and can inhibit LDHA (FIG. 10D;—See FIG. 16). The inventors therefore ex vivo treated renal tumor tissue and adjacent normal kidney-tissue from a BHD patient harboring a pathogenic FLCN mutation with FLCN-10 peptide (See FIG. 11F). The data revealed that FLCN-10 peptide is able to penetrate both normal and tumor tissues (See FIG. 11G), and LDHA inhibition is evident by a reduction in phospho-Tyr10-LDHA (See FIG. 11H). Taken together, the inventors identified a decapeptide within the amino domain of FLCN that is able to entercancer cells and selectively inhibit LDHA activity.

FLCN:LDHA Dissociation Causes Warburg Effect

It is well-established that kidney cancers, in general, experience the "Warburg effect"[29]. The inventors found FLCN expression levels reduced in clear cell renal cell carcinoma (ccRCC) cell lines compared to HEK293 control cells, and these ccRCC cell lines demonstrated hyperactive LDHA (See FIG. 12A). The inventors further observed that FLCN dissociation from LDHA in ccRCC correlated with increased LDHA activity (See FIG. 12A). LDH also forms higher order oligomers in cells observable by native-PAGE[30], which likely correspond to the tetrameric and dimeric states of LDHA reported previously[31]. These ccRCC cell lines demonstrated hyperactive LDHA as evidenced by increased tetramer:dimer ratios quantified by native Western blot densitometry (See FIG. 12B).

Figures 19A, 19B, 19C, 19D:
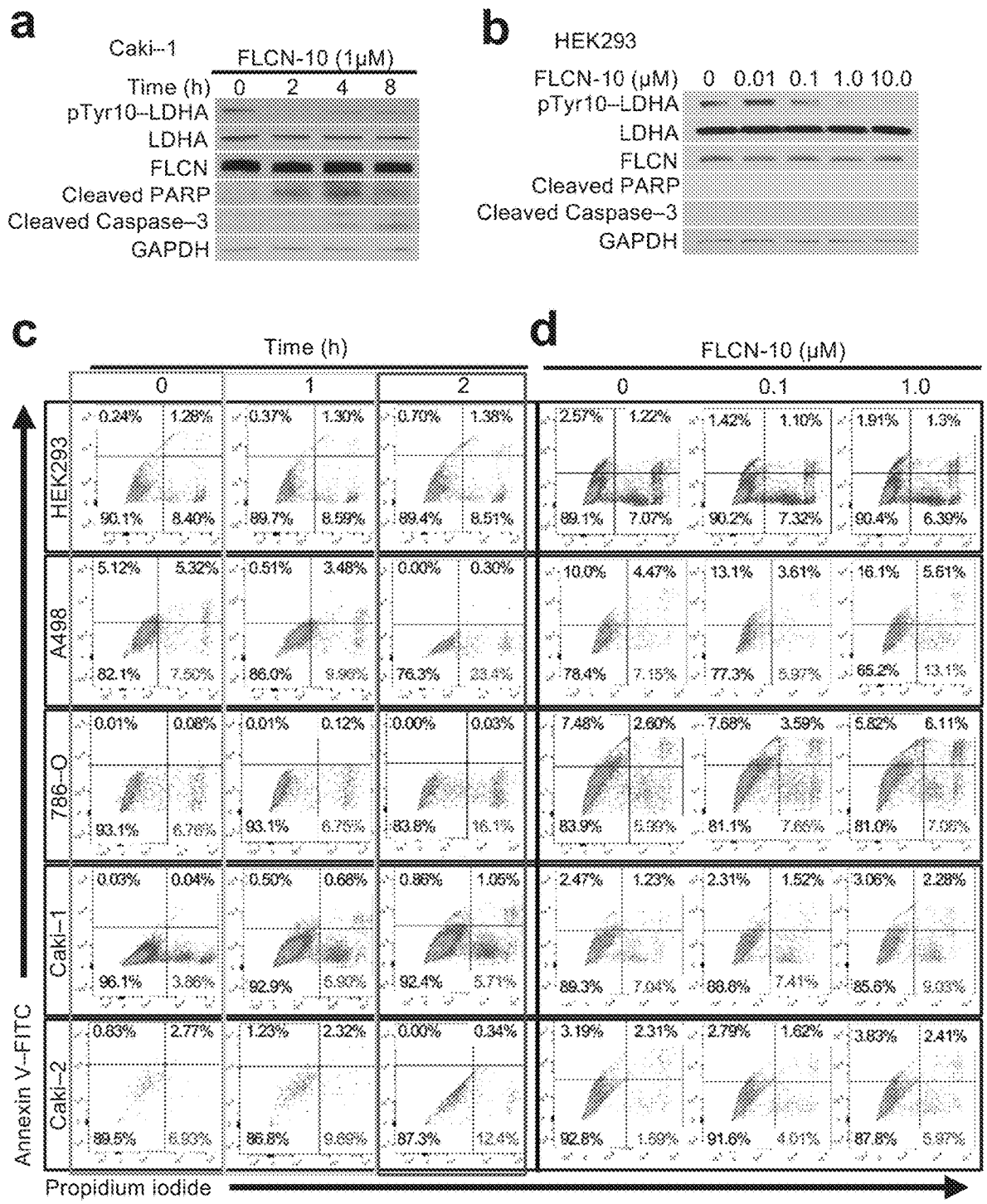
FIGS. 19A-D presents illustrative data relating to the present disclosure as described below.

The inventors next asked whether treatment with the FLCN-10 peptide could affect the survival of ccRCC cell lines, as previous reports show that LDHA inhibition in Warburg-shifted cells induces apoptosis[22]. These ccRCC cell lines treated with the FLCN-10 peptide showed a decrease in LDHA activity and enhanced cell death (See FIG. 12C, FIGS. 19 A and 19C. In control HEK293 cells however the inventors did not observe any apoptosis despite LDHA inhibition (See FIG. 12C, FIG. 19B). Additionally, FLCN-10 peptide treatment induced cell death in a dose-dependent manner in ccRCC, but not HEK293 cells, as evidenced by increased propidium iodide staining (FIG. 19D).

Linear peptides are notoriously unreliable as therapeutic effectors[32]. The inventors therefore created a series of modified peptides to protect them from cellular proteases. Our data showed that both the PEGylated and retroinverse FLCN-10 peptides were effective at inhibiting LDHA activity. However, the heterocyclic FLCN-10 peptide showed increased cell penetrance and cell death in ccRCC relative to linear FLCN-10, as well as a dose-dependent decrease in ECAR (Extended Data FIG. 20A-E). Taken together, cyclization is an effective modification for protecting this peptide while preserving its activity, suggesting potential therapeutic utility that warrants further investigation.

Figures 12D, 12E, 12F:
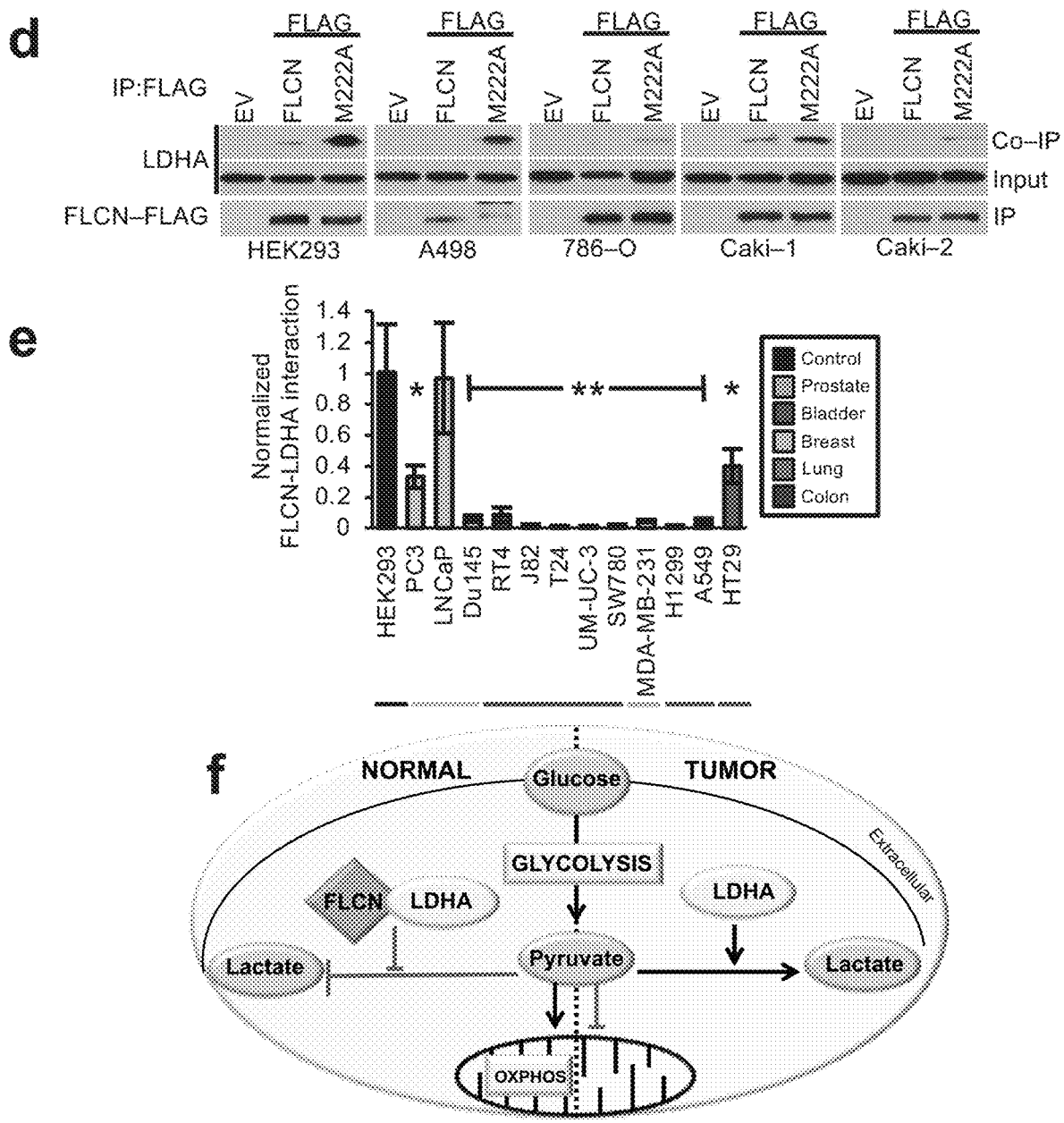
FIG. 12D presents illustrative data relating to IP of WT FLCN and M222A mutant from renal cell lines.
FIG. 12E presents illustrative data relating to normalized FLCN-LDHA interaction from a panel of cancer cell lines (n=3).
FIG. 12F presents a schematic illustration relating to cellular regulation.

As shown in FIG. 11B, FLCN-M222A demonstrates increased binding to LDHA. FLCN-M222A retains the ability to bind LDHA in ccRCC, bypassing the presumed regulatory signaling governing this interaction in kidney cancer (FIG. 12D). The inventors then sought to determine whether dissociation of FLCN from LDHA was a common feature of cancer cells. Across a panel of twelve cancer cell lines, ten demonstrated an increased phospho-Tyr10-LDHA:FLCN ratio, suggesting a link between decreased FLCN expression and increased LDHA activity across cancers (FIGS. 20F-G). Immunoprecipitation of endogenous LDHA from these cancer cell lines confirmed this link, demonstrating a decreased ability of FLCN to interact with LDHA in cancer (FIG. 12E, FIG. 20G). Metabolic imbalance is a hallmark of cancer. While this phenomenon has long been observed, the mechanistic underpinnings of metabolic dysregulation remain poorly understood. Our data demonstrate that FLCN functions as a bona ide endogenous inhibitor of LDHA, responsible for maintaining metabolic homeostasis in normal cells. Loss of FLCN increases glycolytic flux in an LDHA-dependent manner, providing a mechanistic explanation for the kidney tumor formation observed in BHD patients. Cancer cells undergoing the Warburg effect demonstrate loss of FLCN:LDHA interaction and FLCN-mediated LDHA inhibition, which facilitates glycolysis and supports tumor growth (FIG. 12F). A small decapeptide identified in the amino-domain of FLCN is cell-permeant and sufficient to inhibit LDHA, thereby causing cell death in metabolically shifted cancer cells.

Recapitulation of FLCN-mediated LDHA inhibition may be a new avenue for targeted therapy in these cancers.

To summarize FIG. 9, the inventors have shown the tumor suppressor FLCN specifically binds and inhibits LDHA. For example, FIG. 9A shows FLCN-FLAG immunoprecipitated (IP) from HEK293 cells was subjected to MALDI-TOF. Colored circles are interacting proteins: Green—chaperones and adaptors; red—transcription, translation and metabolism; blue—nucleotide-binding; cyan—RNA-binding; beige—chaperonins and cytoskeleton. Interactome was generated using STRING (string-db.org). FIG. 9B shows Immunofluorescence staining with anti-FLCN (red), anti-LDHA (green), nuclei (blue; DAPI) in HEK293 cells. Scale bar=10 μM. FIG. 9C shows IP of LDHA-FLAG or LDHB-FLAG expressed in HEK293 cells immunoblotted with anti-FLCN to assess interaction (Co-IP). FIG. 9D shows LDH activity measured in vitro using whole cell lysates from LDHA or LDHB knockout HAP1 cells following treatment with siRNA targeting FLCN (n=3). FIG. 9E shows Immunoblot of anti-FLCN IPs and whole cell extracts following exogenous addition of pyruvate to HEK293s for 6 h (n=3). SE=short exposure, LE=long exposure. FIG. 9F shows activity of 10 nM recombinant LDHA measured in the presence of increasing amounts of recombinant FLCN (n=3). Data shown as mean s.d. *P<0.05.

Figure 10A:
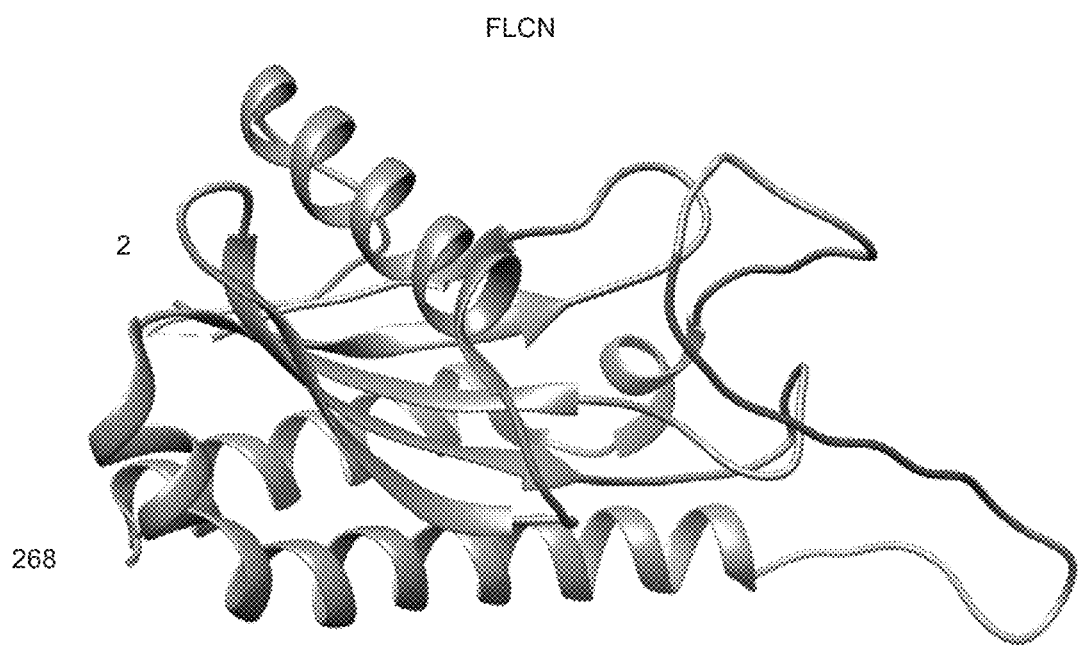
Figures 10B, 10C, 10D:
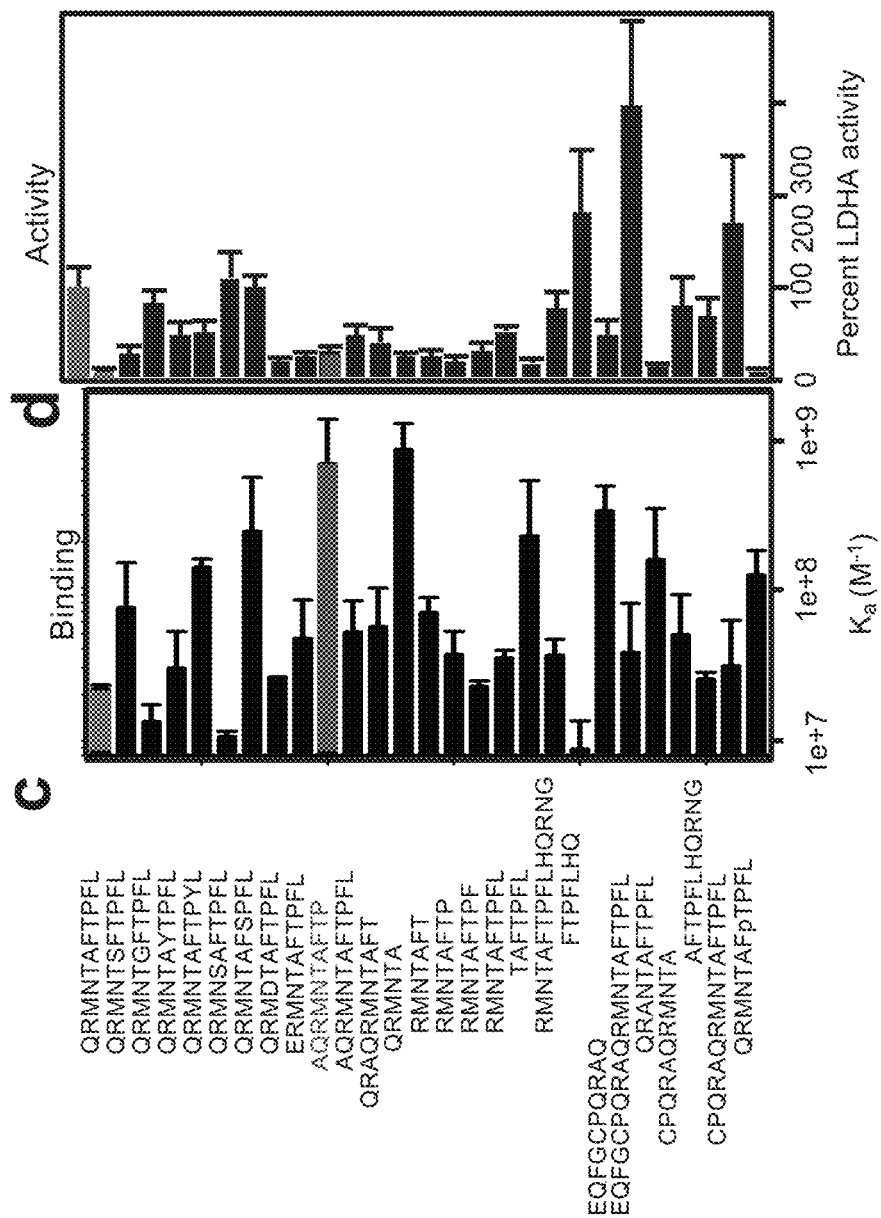
FIG. 10B shows at least FLCN-10 peptide of the present disclosure highlighted in red in accordance with some embodiments of the present disclosure.
FIG. 10C presents illustrative data relating to FLCN peptides screened for $K_a$ (n=3) or FIG. 10D shows the ability to inhibit LDHA (n=3), wherein the green bar represents the activity of LDHA alone (100%), and wherein LDHA activity is highlighted in the presence of FLCN-1 (blue) and FLCN-10 (red).

To summarize FIG. 10, the inventors have shown a decameric peptide of FLCN uncompetitively inhibits LDHA. FIG. 10A refers to structure of FLCN N-terminus solved by cryo-electron microscopy (aa 2-268; PDB ID: 6nzd).FLCN-10 peptide is highlighted in red. FIG. 10B) FLCN peptides screened for FIG. 10C) Ka (n=3) or FIG. 10D) ability to inhibit LDHA (n=3). The green bar represents the activity of LDHA alone (100%). LDHA activity is highlighted in the presence of FLCN-1 (blue) and FLCN-10 (red). FIG. 10E) Michaelis-Menten kinetics of LDHA activity alone or in the presence of FLCN protein or FLCN-10 peptide (n=3). FIG. 10F) FLCN-10 is an uncompetitive inhibitor of LDHA based on Lineweaver-Burke plot of enzyme kinetics (n=3). FIG. 10G) Measured values for LDHA binding and kinetic data from FIG. 10 and FIGS. 12A-E. FIG. 10H) Structure of dimeric LDHA, individual monomers have been colored light or dark blue (PDB ID: 4okn). Limited proteolysis-couple MS identified LDHA catalytic loop region perturbation (red) in response to FLCN-10 peptide binding. The green α helix represents peptides unchanged by the presence of FLCN-10. The LDHA catalytic R106 is highlighted in orange. Data shown as mean±s.d. Structures rendered using Chimera v1.12 (USCF).

To summarize FIG. 11, the inventors have shown LDHA hyperactivity is abrogated by ex vivo FLCN peptide treatment in BHD kidney tumors. FIG. 11A presents structure of FLCN flexible loop with flanking α-helices (aa 178-267). Unstructured loop region is highlighted in orange, FLCN-10 peptide region with sidechains displayed in red (PDB ID: 6ulg). Structure rendered using Chimera v1.12 (USCF). FIG. 11B) Individual amino acid mutations in FLCN-10 residues (blue). FIG. 11C) Point mutations within the FLCN peptide region were transiently expressed in HEK293 cells and immunoprecipitated. Interaction with LDHA (Co-IP) was assessed by immunoblot. FIG. 11D) Extracellular acidification rate of UOK257 cells transfected with 8 μg of WT FLCN, M222A or F226A mutants (n=6). FIG. 11E) LDH activity of lysates collected from c (n=3). FIG. 11F H+E staining of normal and tumor renal tissues from a patient with BHD. FIG. 11G Fluorescence microscopy of normal and tumor renal tissues from a patient with BHD treated with FLCN-10-Rhodamine B and stained with anti-FLCN (green), anti-LDHA (pink) and DNA (Hoechst 33258; blue) Scale bar=20 μm. FIG. 11H) Western blots of lysates collected from FIG. 3f. Data shown as mean s.d. *P<0.05, P<0.005, *P<0.0005, ****P<0.0001.

To summarize FIG. 12, the inventors have shown FLCN peptide induces apoptosis in cancer cell lines. FIG. 12A Endogenous anti-LDHA immunoprecipitation from renal cell lines. Interaction with FLCN was observed by immunoblot. FIG. 12B Native Western blot using anti-LDHA in renal cell lines. SE=short exposure, LE=long exposure. FIG. 12C low cytometric assessment of cell death in renal cell lines following treatment with 1 or 2 h of 1 µM FLCN-10 as determined by propidium iodide staining. (Green=NT, Yellow=1 h FLCN-10 treatment, Red=2 h FLCN-10 treatment). Representative of three independent experiments. FIG. 12D IP of WT FLCN and M222A mutant from renal cell lines. Interaction with LDHA was observed by immunoblot. FIG. 12E Normalized FLCN-LDHA interaction from a panel of cancer cell lines (n=3). FIG. 12F in normal cells, FLCN regulates the activity of LDHA. In cancer cells going through the Warburg effect, FLCN and LDHA have lost the ability to interact, leading to the hyperactivity of LDHA.Data shown as mean}s.d. *P<0.05, **P<0.005.

Figure 13:
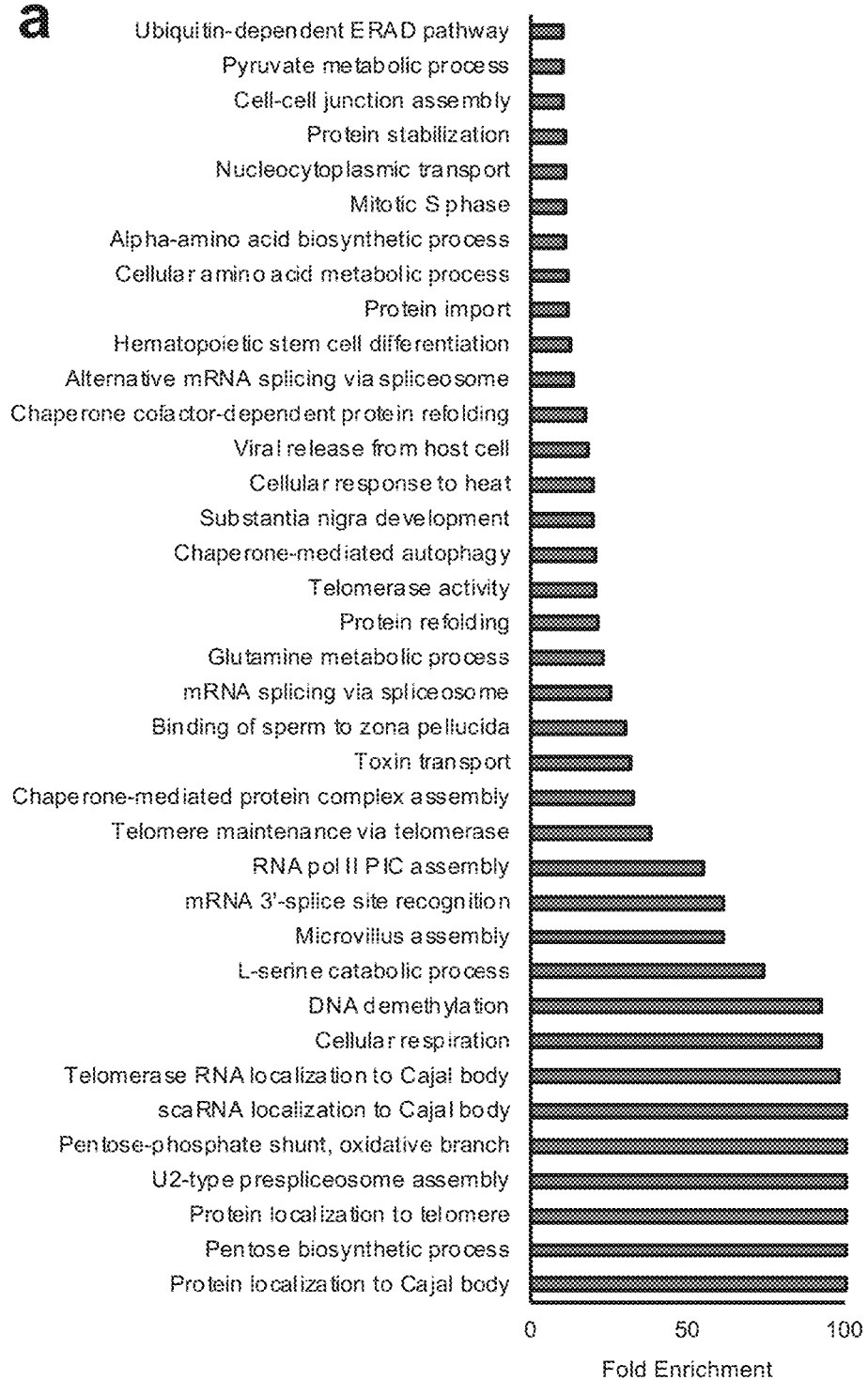
FIG. 13A presents illustrative data relating to GO term analysis of FLCN proteomic data using Panther v15.0 (pantherdb.org).
FIG. 13B presents illustrative data relating to LDHA-FLAG immunoblotting.
FIG. 13C presents illustrative data relating to FLCN-FLAG IP.
FIG. 13D presents illustrative data relating to tagged LDHA and LDHB subunits that were consecutively immunoprecipitated and immunoblotted with anti-FLCN.
FIG. 13E presents western blot of siRNA knockdown of FLCN for FIG. 9C.
Figure 13B:
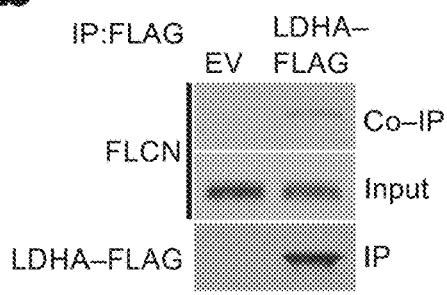
Figure 13C:
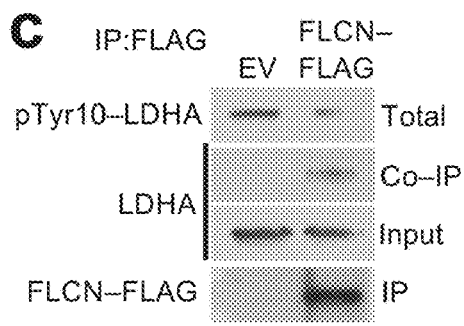
Figure 13D:
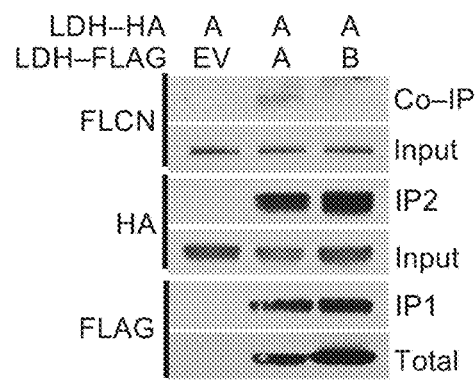
Figure 13E:
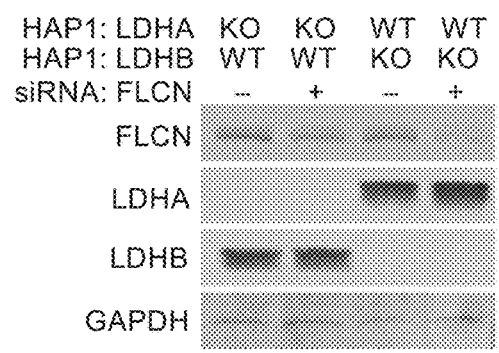

To summarize FIG. 13, the inventors have provided additional data. FIG. 13A, GO term analysis of FLCN proteomic data using Panther v15.0 (pantherdb.org). FIG. 13B) LDHA-FLAG or FIG. 13C) FLCN-FLAG IP from HEK293 cells was immunoblotted with anti-FLCN and anti-LDHA, respectively. FIG. 13D) Tagged LDHA and LDHB subunits were consecutively immunoprecipitated and immunoblotted with anti-FLCN. FIG. 13E) Western blot of siRNA knockdown of FLCN for FIG. 9C.

Figure 14C:
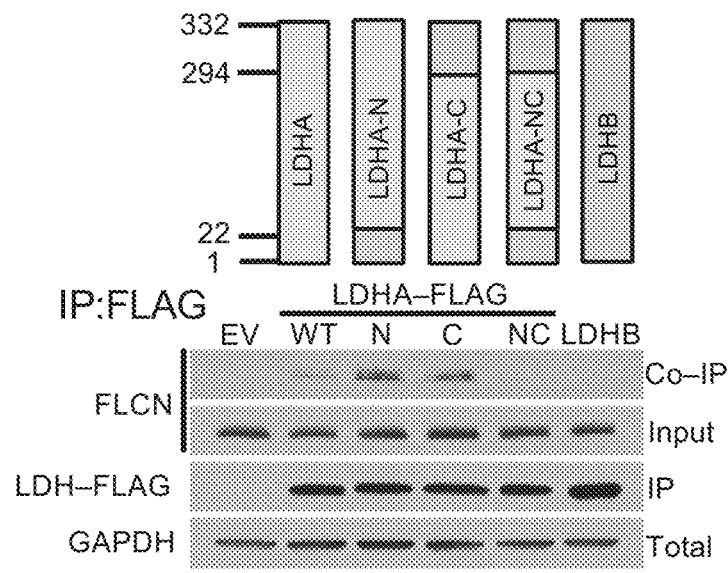
FIGS. 14C, 14D, and 14E present illustrative data relating to immunoblotting as described below.
Figure 14D:
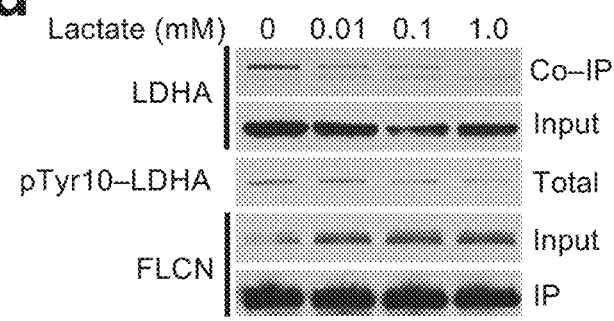
Figure 14E:
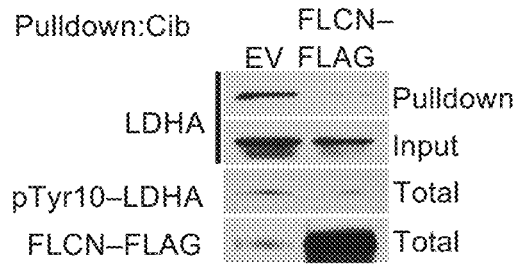

FIG. 14A shows a sequence alignment of human LDHA and human LDHB using https://clustalw.ddbj.nig.ac.jp/. The red N- and blue C-terminal residues that were swapped to generate the N, C and NC chimeric constructs used in FIG. 14C are highlighted. The active site loop (99-110) is colored cyan. FIG. 14B) LDHA tetramer (PDB ID: 1i10) in ribbon (top) and surface (bottom) models represented in the standard view (left) and 90° rotated view (right). The N-terminus (residues 1-22) is highlighted in red and the C-terminus (residues 294-332) is highlighted in blue. Note the proximity of the Cterminal helix (blue) to the active site loop (residues 99-110; cyan) within each subunit. In the tetrameric arrangement, the N- and C-terminal residues of adjacent subunits form a continuous surface. Structure rendered using PyMOL 2.3. FIG. 14C) LDHA/LDHB chimeric constructs were transfected into HEK293 cells and immunoprecipitated. Co-immunoprecipitation of FLCN was detected by immunoblot. FIG. 14D) Immunoblot of FLCN and LDHA interaction following exogenous addition of lactate to HEK293s. FIG. 14E) Pulldown of LDHA from cell lysate expressing EV or FLCN-FLAG using Cibacron blue agarose was evaluated by immunoblot.

Figures 15A, 15B, 15C, 15D, 15E, 15F:
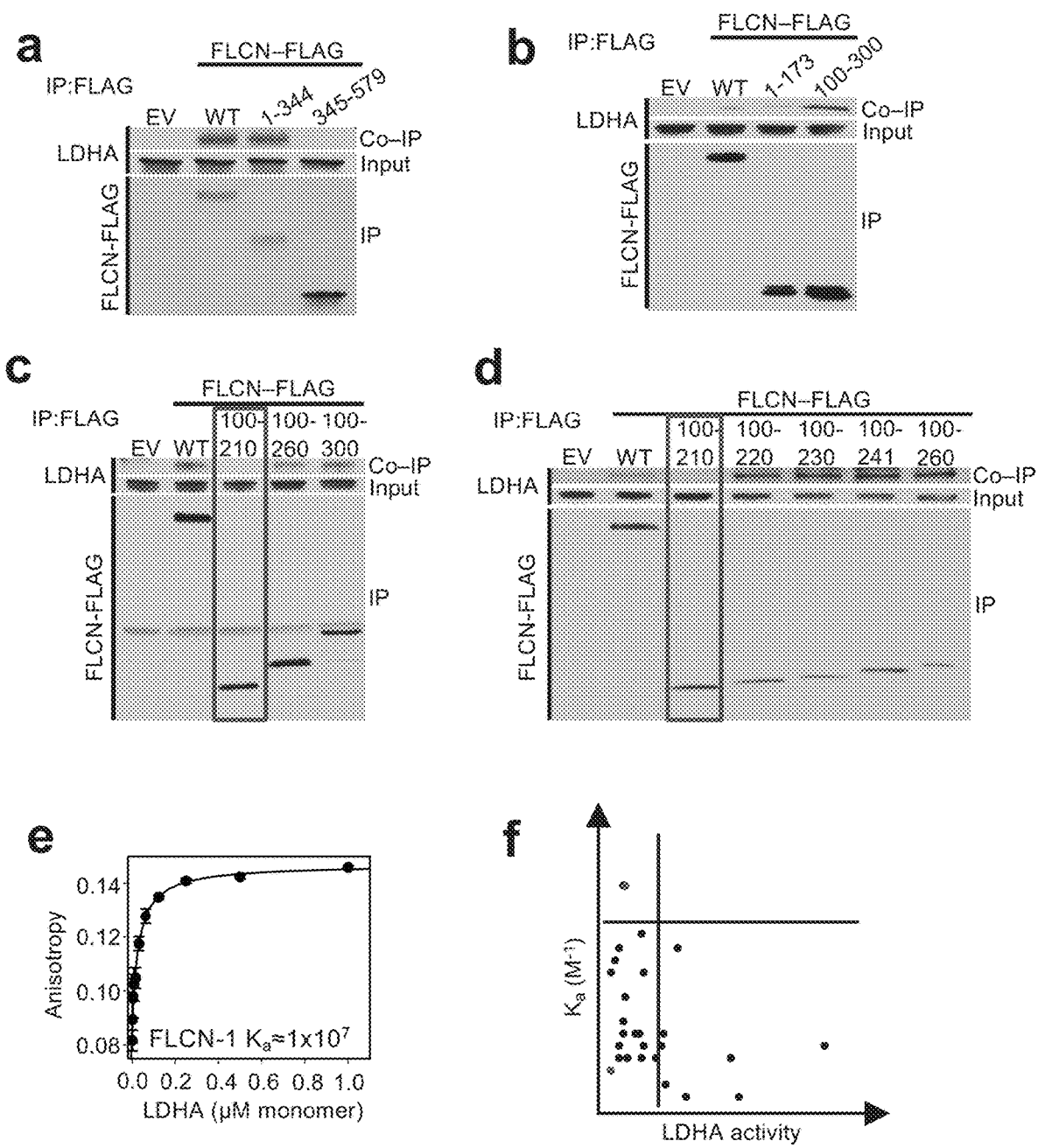
FIGS. 15A-15F present illustrative data as described further below.

FIGS. 15 A-D) Immunoprecipitation of transiently expressed short segments of FLCN-FLAG protein implies the critical interacting region with LDHA. FIG. 15E) Ka of LDHA with FLCN-1 peptide (See FIG. 10C), measured by fluorescence polarization anisotropy (n=3). FIG. 15F) Ka plotted against LDHA activity in the presence of peptides. FLCN-1 peptide (blue) and FLCN-10 peptide (red) are highlighted.

FIG. 16 provides Fluorescence microscopy of HEK293 cells treated with 1 µM Rhodamine B-labeled peptides from FIG. 10B. Peptides that are resident after two hours treatment have been denoted with a red number and box. NT=No treatment. Scale bar=10 µM.

Figures 17A, 17B, 17C, 17D:
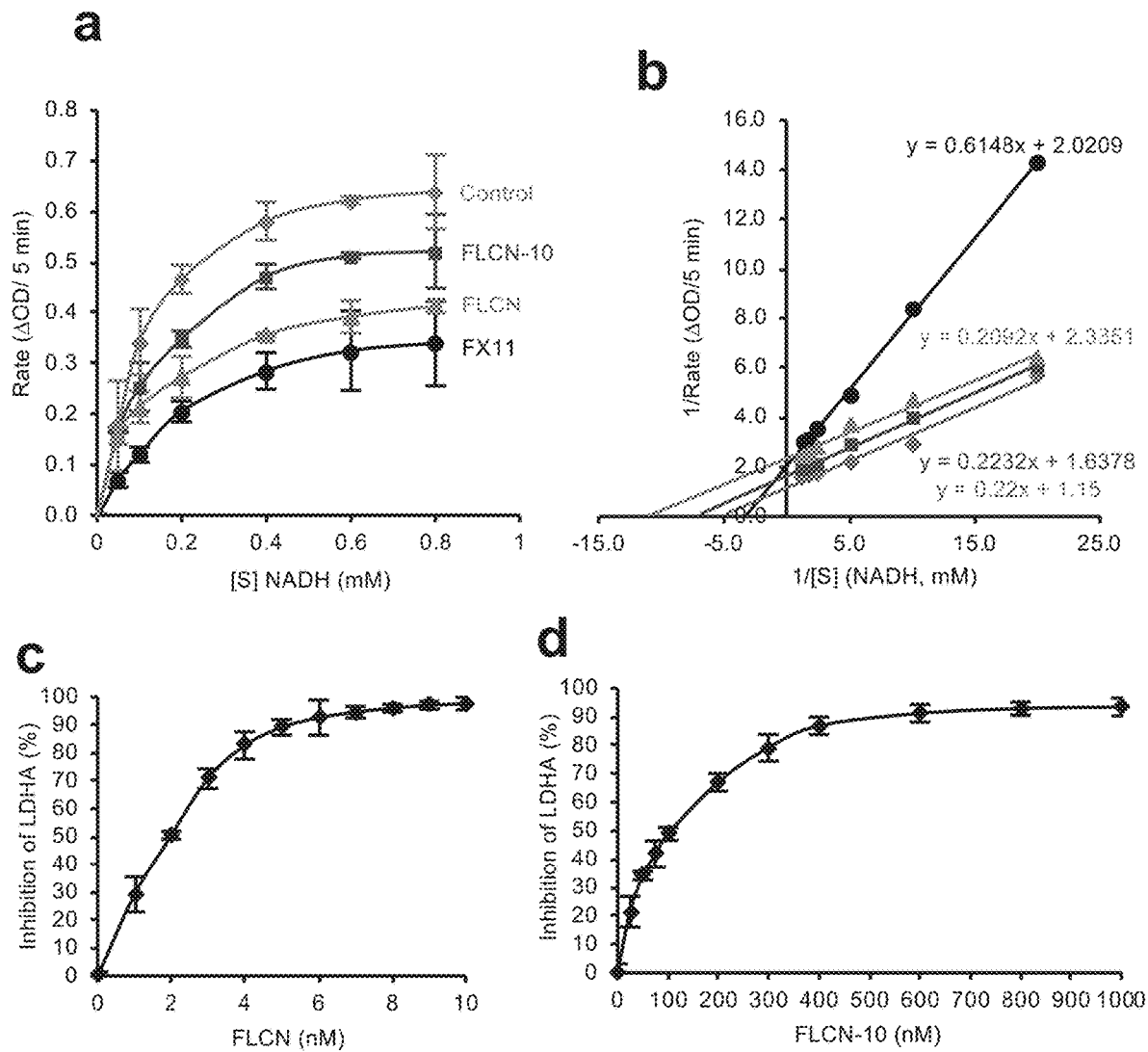

To summarize FIG. 17, FIG. 17 A shows Michaelis-Menten kinetics of LDHA in the presence of FLCN protein, FLCN-10 peptide, or FX11 (n=3). FIG. 17B shows FLCN-10 is an uncompetitive inhibitor of LDHA based on Lineweaver-Burke plot (n=3). FIGS. 17C-E show $IC_{50}$ measurements for LDHA in the presence of FLCN protein, FLCN-10 peptide, or FX-11 (n=3). FIG. 17F shows LDHA-R106-FLAG mutants were transiently transfected and immunoprecipitated from HEK293s. FLCN interaction assessed by immunoblotting. Binding to FLCN-10-Biotin peptide was assessed by Streptavidin pulldown.

To summarize FIG. 18, FIG. 18 shows at FIG. 18A HEK293 cells were treated with and without 1 µM Rhodamine B-labeled FLCN-10A. Scale bar=20 µM. FIG. 18B LDHA activity in HEK293 cells following 2 h treatment with FLCN-10A peptide. FIG. 18C, Western blot confirming transfection of FLCN-WT-FLAG and FLCN-M222A-FLAG in UOK257 cells in FIG. 11C-D. FIG. 18D shows expansion of FIG. 11c, extracellular acidification rate of high and low dose transfections of WT FLCN, M222A and F226A (n=6). FIG. 18E shows expansion of FIG. 11D, LDH activity in high and low dose transfections of WT FLCN, M222A and F226A. Only significant pairwise comparisons in addition to FIG. 3d have been shown (n=3). FIG. 11F shows Western blot confirming transfection of FLCN-WT-FLAG and FLCN-F226A-FLAG in UOK257 cells in FIGS. 18D-E. FIG. 18G shows extracellular acidification rate of UOK257 cells treated for 2 h with increasing doses of FLCN-10 peptide (n=6). FIG. 18H shows LDHA activity in UOK257 cells transfected with EV, WT FLCN, FLCN-F118D-FLAG and FLCN-R164A-FLAG (n=3). Data shown as mean±}s.d. *P<0.05, P<0.005, *P<0.0005.

FIG. 19 is summarized as, FIG. 19A refers to Caki-1 cells treated with FLCN-10 were blotted using anti-cleaved caspase-3 and anti-pTyr10-LDHA. FIG. 19B shows LDHA activity in HEK293 cells following 2 h treatment with FLCN-10 peptide. FIGS. 19C-D show flow cytometric assessment of cell death in renal cell lines following 1 µM FLCN-10 for 1 or 2 h (FIG. 4c) or 0.1 µM or 1 µM FLCN-10 treatment for 2 h (FIG. 12D) as determined by Annexin V/Propidium iodide staining. Representative of three independent experiments.

Figures 20A, 20B, 20C, 20D:
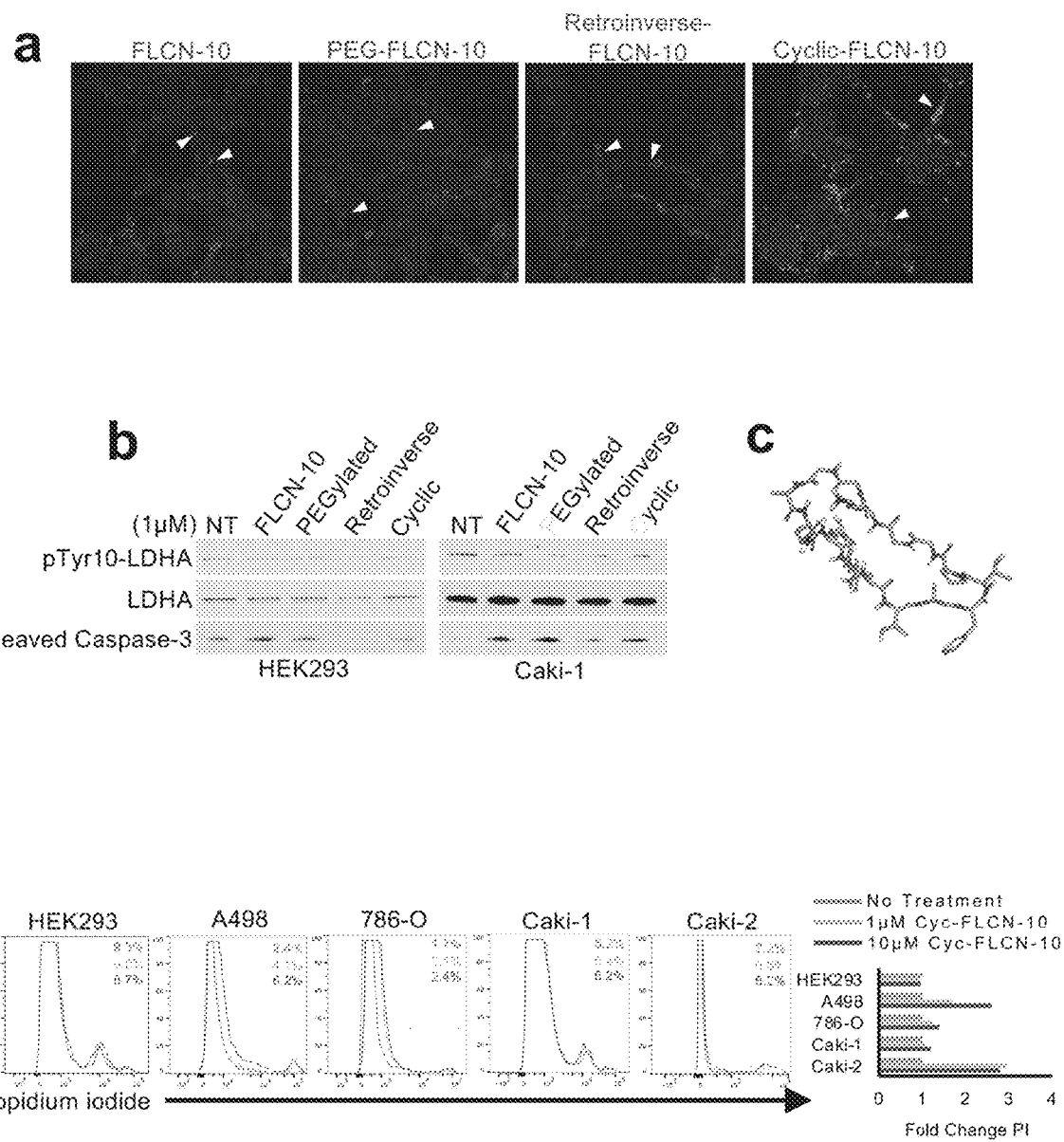

FIG. 20A shows fluorescence imaging of modified Rhodamine B-labeled FLCN-10 peptides in HEK293 cells. White arrows denote examples of FLCN-10 localization. Scale bar=10 µM. FIG. 20B shows Western blot of pTyr10-LDHA and cleaved caspase-3 in HEK293 and Caki-1 cells following treatment with modified FLCN peptides. FIG. 20C shows a structural representation of head-to-tail cyclic-FLCN-10 peptide, created using MAESTRO (Schrodinger.com). FIG. 20D shows flow cytometric assessment of cell death in renal cell lines following 1 µM or 10 µM cyclic-FLCN-10 treatment as determined by propidium iodide staining. Representative of three independent experiments. FIG. 20E shows the extracellular acidification rate of UOK257 cells treated with increasing doses of Cyc-FLCN-10 peptide for 2 h (n=6). FIG. 20F shows the densitometric ratio of normalized pTyr10-LDHA:FLCN expression in a panel of cancer cell lines (n=3). #=not statistically significant, ^=**P<0.005. FIG. 20G shows Immunoblots of endogenous FLCN and pTyr10-LDHA and interaction of FLCN and LDHA (from FIG. 12E and Extended Data FIG. 20). Data shown as mean±}s.d. *P<0.05, P<0.005, *P<0.0005, ****P<0.0001.

In some embodiments, the present disclosure relates to a peptide including a core sequence that differs from SEQ ID NO: 10 by a single amino acid substitution. In embodiments, the single amino acid substitution includes an alanine (A) residue substituted with an asparagine (N) or any non-alanine residue substituted with an alanine. In some embodiments, the single amino acid substitution includes a non-natural amino acid substitution. In some embodiments, the non-natural amino acid substitution includes substitution with a non-natural amino acid selected from a D-amino acid, a homo-amino acid, abeta homo amino acid, an N-methyl amino acid, and an alpha-methyl amino acid. In some embodiments, the core sequence is selected from the group consisting of SEQ ID NOs: 28-37. In some embodiments, the core sequence is selected from the group consisting of SEQ ID NOs: 29, 31, 32, 33 and 36. In some embodiments, the core sequence comprises SEQ ID NO: 31. In embodiments, the peptide includes a modification to increase stability. In embodiments, the modification is selected from the group consisting of PEGylation, cyclization, and retro-inversion. In embodiments, the peptide is between 10 and 30 amino acid long. In some embodiments, the peptide is disposed within a pharmaceutically acceptable carrier.

In some embodiments, the present disclosure relates to a method of inhibiting lactate dehydrogenase A (LDHA) activity in a cell, including contacting the cell with an effective amount of the peptide of the present disclosure. In some embodiments, the cell has increased LDHA activity. In some embodiments, the cell is from an individual having or suspected of having cancer. In some embodiments, the cancer is renal, prostate, or breast cancer. In some embodiments, the cell is from an individual having or suspected of having a metabolic disorder. In some embodiments, the metabolic disorder is diabetes. In some embodiments, the cell is from an individual having or suspected of having Birt-Hogg-Dube syndrome.

In some embodiments, the present disclosure relates to a method of treating an individual having elevated levels of lactate dehydrogenase A (LDHA) activity including administering to the individual a therapeutically effective amount of a peptide comprising a core sequence that differs from SEQ ID NO: 10 by a single amino acid substitution. In some embodiments, the peptide is disposed within a pharmaceutically suitable composition.

REFERENCES

1. Warburg, O. The Metabolism of Carcinoma Cells. *The Journal of Cancer Research* 9, 148, doi:10.1158/jcr.1925.148 (1925).
2. Vander Heiden, M. G. & DeBerardinis, R. J. Understanding the Intersections between Metabolism and Cancer Biology. *Cell* 168, 657-669, doi:10.1016/j.cell.2016.12.039 220 (2017).
3. Dawson, D. M., Goodfriend, T. L., Kaplan, N. O. & Kaplan, N. O. Lactic Dehydrogenases: Functions of the Two Types. *Science* 143, 929, doi:10.1126/science.143.3609.929 (1964).
4. Hathaway, G. & Criddle, R. S. Substrate-dependent association of lactic dehydrogenase subunits to active tetramer. *Proc Natl Acad Sci USA* 56, 680-685, 225 doi:10.1073/pnas.56.2.680 (1966).
5. Preston, R. S. et al. Absence of the Birt-Hogg-Dube gene product is associated with increased hypoxia-inducible factor transcriptional activity and a loss of metabolic flexibility. *Oncogene* 30, 1159-1173, doi:10.1038/onc.2010.497 (2011).
6. Schmidt, L. S. Birt-Hogg-Dube syndrome: from gene discovery to molecularly targeted therapies. *Fam Cancer* 12, 357-364, doi:10.1007/s0689-012-9574-y (2013).
7. Tsun, Z. Y. et al. The folliculin tumor suppressor is a GAP for the RagC/D GTPases that signal amino acid levels to mTORC1. *Mol Cell* 52, 495-505, doi:10.1016/j.molcel.2013.09.016 (2013).
8. Petit, C. S., Roczniak-Ferguson, A. & Ferguson, S. M. Recruitment of folliculin to 235 lysosomes supports the amino acid-dependent activation of Rag GTPases. *J Cell Biol* 202, 1107-1122, doi:10.1083/jcb.201307084 (2013).
9. Fan, J. et al. Tyrosine phosphorylation of lactate dehydrogenase A is important for NADH/NAD(+) redox homeostasis in cancer cells. *Mol Cell Biol* 31, 4938-4950, doi:10.1128/MCB.06120-11 (2011).
10. Jin, L. et al. Phosphorylation-mediated activation of LDHA promotes cancer cell invasion and tumour metastasis. *Oncogene* 36, 3797-3806, doi:10.1038/onc.2017.6 (2017).
11. Read, J. A., Winter, V. J., Eszes, C. M., Sessions, R. B. & Brady, R. L. Structural Basis for Altered Activity of M- and H-Isoenzyme Forms of Human Lactate Dehydrogenase. *PROTEINS: Structure, Function, and Genetics* 43, 175-185 (2001).
12. Yamamoto, S. & Storey, K. B. Dissociation-association of lactate dehydrogenase 246 isozymes: influences on the formation of tetramers versus dimers of M4-LDH and H4-LDH. *Int J Biochem* 20, 1261-1265 (1988).
13. Zheng, Y., Guo, S., Guo, Z. & Wang, X. Effects of N-terminal deletion mutation on rabbit muscle lactate dehydrogenase. *Biochemistry (Mosc)* 69, 401-406 (2004).
14. Valvona, C. J., Fillmore, H. L., Nunn, P. B. & Pilkington, G. J. The Regulation and Function of Lactate Dehydrogenase A: Therapeutic Potential in Brain Tumor. *Brain Pathol* 26, 3-17, doi:10.1111/bpa.12299 (2016).
15. Tarmy, E. M. & Kaplan, N. O. Kinetics of *Escherichia coli* B D-lactate dehydrogenase and evidence for pyruvate-controlled change in conformation. *J Biol Chem* 243, 2587-2596 (1968).
16. Jiang, G. R., Nikolova, S. & Clark, D. P. Regulation of the ldhA gene, encoding the fermentative lactate dehydrogenase of *Escherichia coli*. *Microbiology* 147, 2437-2446, doi:10.1099/00221287-147-9-2437 (2001).
17. Yamamoto, S. & Storey, K. B. Influence of glycerol on the activity and tetramer-dimer state of lactate dehydrogenase isozymes. *Int J Biochem* 20, 1267-1271 (1988).
18. Bohabova, V., Dočolomansky, P., Breier, A., Gemeiner, P. & Ziegelhoffer, A. Interaction of lactate dehydrogenase with anthraquinone dyes: characterization of ligands for dye-ligand chromatography. *Journal of Chromatography B: Biomedical Sciences and Applications* 715, 273-281, doi://doi.org/0.1016/S378-4347(98)00088-7 (1998).
19. Cahn, R. D., Zwilling, E., Kaplan, N. O. & Levine, L. Nature and Development of Lactic Dehydrogenases: The two major types of this enzyme form molecular hybrids which change in makeup during development. *Science* 136, 962-969, doi:10.1126/science.136.3520.962 (1962).
20. Shen, K. et al. Cryo-EM Structure of the Human FLCN-FNIP2-Rag-Ragulator Complex. *Cell* 179, 1319-1329.e1318, doi:10.1016/j.cell.2019.10.036 (2019).
21. Lawrence, R. E. et al. Structural mechanism of a Rag GTPase activation checkpoint by the lysosomal folliculin complex. *Science* 366, 971-977, doi:10.1126/science.aax0364 (2019).
22. Le, A. et al. Inhibition of lactate dehydrogenase A induces oxidative stress and inhibits tumor progression. *Proc Natl Acad Sci USA* 107, 2037-2042, doi:10.1073/pnas.0914433107 (2010).
23. Schopper, S. et al. Measuring protein structural changes on a proteome-wide scale using limited proteolysis-coupled mass spectrometry. *Nat Protoc* 12, 2391-2410, doi:10.1038/nprot.2017.100 (2017).
24. Woodford, M. R., Chen, V. Z., Backe, S. J., Bratslavsky, G. & Mollapour, M. Structural and functional regulation of lactate dehydrogenase-A in cancer. *Future Medicinal Chemistry* 12, 439-455, doi:10.4155/fmc-2019-0287 (2020).
25. Clarke, A. R. et al. Site-directed mutagenesis reveals role of mobile arginine residue in lactate dehydrogenase catalysis. *Nature* 324, 699-702, doi:10.1038/324699a0 (1986).
26. Nookala, R. K. et al. Crystal structure of folliculin reveals a hidDENN function in genetically inherited renal cancer. *Open Biol* 2, 120071, doi:10.1098/rsob.120071 (2012).
27. Nickerson, M. L. et al. Mutations in a novel gene lead to kidney tumors, lung wall defects, and benign tumors of the hair follicle in patients with the Birt-Hogg-Dubé syndrome. 288 *Cancer Cell* 2, 157-164 (2002).
28. Yang, Y. et al. The UOK 257 cell line: a novel model for studies of the human Birt-Hogg-Dube gene pathway. *Cancer Genet Cytogenet* 180, 100-109, doi:10.1016/j.cancergencyto.2007.10.010 (2008).
29. Linehan, W. M. et al. The Metabolic Basis of Kidney Cancer. *Cancer Discov* 9, 1006-1021, doi:10.1158/2159-8290.CD-18-1354 (2019).
30. Unkles, S. E. et al. Physiological and biochemical characterization of AnNitA, the *Aspergillus nidulans* high-affinity nitrite transporter. *Eukaryot Cell* 10, 1724-1732, doi:10.1128/EC.05199-11 (2011).
31. Yamamoto, S. S., K. B. Dissociation-Association of Lactate Dehydrogenase Isozymes:Influences on the Formation of Tetramers versus Dimers of M4-LDH and H4-LDH. *Int. J. Biochem.* 20, 1261-1265 (1988).
32. Fosgerau, K. & Hoffmann, T. Peptide therapeutics: current status and future directions. *Drug Discovery Today* 20, 122-128, doi:10.1016/j.drudis.2014.10.003 (2015).
33. Cox, J. & Mann, M. MaxQuant enables high peptide identification rates, individualized p.p.b.-range mass accuracies and proteome-wide protein quantification. *Nat Biotechnol* 26, 1367-1372, doi:10.1038/nbt.1511 (2008).
34. Woodford, M. R. et al. The FNIP co-chaperones decelerate the Hsp90 chaperone cycle and enhance drug binding. *Nat Commun* 7, 12037, doi:10.1038/ncomms12037 (2016).
35. Gay, R. J., McComb, R. B. & Bowers Jr., G. N. Optimum Reaction Conditions for Human Lactate Dehydrogenase Isoenzymes as They Affect Total Lactate Dehydrogenase Activity. *Clinical Chemistry* 14, 740-753 (1968).
36. Powers, J. L., Kiesman, N. E., & Tran, C. M., Brown, J. H., Bevilacqua, V. L. H. Lactate Dehydrogenase Kinetics and Inhibition Using a Microplate Reader*. *Biochemistry and Molecular Biology Education* 35, 287-292, doi: 10.1002/bambed.74 (2007).
37. Cer, R. Z., Mudunuri, U., Stephens, R. & Lebeda, F. J. IC50-to-Ki: a web-based tool for converting IC50 to Ki values for inhibitors of enzyme activity and ligand binding. *Nucleic Acids Res* 37, W441-445, doi:10.1093/nar/gkp253 (2009).

The entire disclosure of all applications, patents, and publications cited herein are herein incorporated by reference in their entirety. While the foregoing is directed to embodiments of the present disclosure, other and further embodiments of the disclosure may be devised without departing from the basic scope thereof.

What is claimed:

1. A peptide comprising a core sequence that differs from SEQ ID NO: 10 by a single amino acid substitution, wherein the single amino acid substitution comprises an alanine (A) residue substituted with an asparagine (N) or any non-alanine residue substituted with an alanine.

2. A peptide consisting of a sequence that differs from SEQ ID NO: 10 by a single amino acid substitution, wherein the single amino acid substitution comprises a non-natural amino acid substitution.

3. The peptide of claim 1, wherein the non-natural amino acid substitution comprises substitution with a non-natural amino acid selected from a D-amino acid, a homo-amino acid, a beta homo amino acid, an N-methyl amino acid, and an alpha-methyl amino acid.

4. The peptide of claim 1, wherein the core sequence is selected from the group consisting of SEQ ID NOs: 28-37.

5. The peptide of claim 1, wherein the core sequence is selected from the group consisting of SEQ ID NOs: 29, 31, 32, 33, and 36.

6. The peptide of claim 1, wherein the core sequence comprises SEQ ID NO: 31.

7. The peptide of claim 1, wherein the peptide is between 10 and 30 amino acid long.

8. A method of inhibiting lactate dehydrogenase A (LDHA) activity in a cell, comprising contacting the cell with an effective amount of the peptide of claim 1.

9. The method of claim 8, wherein the cell has increased LDHA activity.

10. The method of claim 9, wherein the cell is from an individual having or suspected of having cancer.

11. The method of claim 10, wherein the cancer is renal, prostate, or breast cancer.

12. The method of claim 8, wherein the cell is from an individual having or suspected of having a metabolic disorder.

13. The method of claim 12, wherein the metabolic disorder is diabetes.

14. The method of claim 8, wherein the cell is from an individual having or suspected of having Birt-Hogg-Dube syndrome.

15. A method of treating an individual having elevated levels of lactate dehydrogenase A (LDHA) activity comprising administering to the individual a therapeutically effective amount of a peptide of claim 1.

16. The method of claim 15, wherein the peptide is disposed within a pharmaceutically suitable composition.

* * * * *

SEQUENCE LISTING

```
<160> NUMBER OF SEQ ID NOS: 41

<210> SEQ ID NO 1
<211> LENGTH: 11
<212> TYPE: PRT
<213> ORGANISM: Artificial Sequence
<220> FEATURE:
<223> OTHER INFORMATION: Oligopeptide

<400> SEQUENCE: 1

Gln Arg Met Asn Thr Ala Phe Thr Pro Phe Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Oligopeptide

<400> SEQUENCE: 2

Gln Arg Met Asn Thr Ser Phe Thr Pro Phe Leu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Oligopeptide

<400> SEQUENCE: 3

Gln Arg Met Asn Thr Gly Phe Thr Pro Phe Leu
```

```
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Oligopeptide

<400> SEQUENCE: 4

Gln Arg Met Asn Thr Ala Tyr Thr Pro Phe Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Oligopeptide

<400> SEQUENCE: 5

Gln Arg Met Asn Thr Ala Phe Thr Pro Tyr Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Oligopeptide

<400> SEQUENCE: 6

Gln Arg Met Asn Ser Ala Phe Thr Pro Phe Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Oligopeptide

<400> SEQUENCE: 7

Gln Arg Met Asn Thr Ala Phe Ser Pro Phe Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Oligopeptide

<400> SEQUENCE: 8

Gln Arg Met Asp Thr Ala Phe Thr Pro Phe Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Oligopeptide

<400> SEQUENCE: 9

Glu Arg Met Asn Thr Ala Phe Thr Pro Phe Leu
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: Oligopeptide

<400> SEQUENCE: 10

Ala Gln Arg Met Asn Thr Ala Phe Thr Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Oligopeptide

<400> SEQUENCE: 11

Ala Gln Arg Met Asn Thr Ala Phe Thr Pro Phe Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Oligopeptide

<400> SEQUENCE: 12

Gln Arg Ala Gln Arg Met Asn Thr Ala Phe Thr
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Oligopeptide

<400> SEQUENCE: 13

Gln Arg Met Asn Thr Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Oligopeptide

<400> SEQUENCE: 14

Arg Met Asn Thr Ala Phe Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Oligopeptide

<400> SEQUENCE: 15

Arg Met Asn Thr Ala Phe Thr Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Oligonucleotide

<400> SEQUENCE: 16

Arg Met Asn Thr Ala Phe Thr Pro Phe
1               5

<210> SEQ ID NO 17
<211> LENGTH: 10
<212> TYPE: PRT
<213> ORGANISM: Artificial Sequence
<220> FEATURE:
<223> OTHER INFORMATION: Oligopeptide

<400> SEQUENCE: 17

Arg Met Asn Thr Ala Phe Thr Pro Phe Leu
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Oligopeptide

<400> SEQUENCE: 18

Thr Ala Phe Thr Pro Phe Leu
1               5

<210> SEQ ID NO 19
<211> LENGTH: 15
<212> TYPE: PRT
<213> ORGANISM: Artificial Sequence
<220> FEATURE:
<223> OTHER INFORMATION: Oligopeptide

<400> SEQUENCE: 19

Arg Met Asn Thr Ala Phe Thr Pro Phe Leu His Gln Arg Asn Gly
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Oligopeptide

<400> SEQUENCE: 20

Phe Thr Pro Phe Leu His Gln
1               5

<210> SEQ ID NO 21
<211> LENGTH: 10
<212> TYPE: PRT
<213> ORGANISM: Artificial Sequence
<220> FEATURE:
<223> OTHER INFORMATION: Oligopeptide

<400> SEQUENCE: 21

Glu Gln Phe Gly Cys Pro Gln Arg Ala Gln
1               5                   10

```
<210> SEQ ID NO 22
<211> LENGTH: 20
<212> TYPE: PRT
<213> ORGANISM: Artificial Sequence
<220> FEATURE:
<223> OTHER INFORMATION: Oligopeptide

<400> SEQUENCE: 22

Glu Gln Phe Gly Cys Pro Gln Arg Ala Gln Arg Met Asn Thr Ala Phe
1               5                   10                  15

Thr Pro Phe Leu
            20

<210> SEQ ID NO 23
<211> LENGTH: 11
<212> TYPE: PRT
<213> ORGANISM: Artificial Sequence
<220> FEATURE:
<223> OTHER INFORMATION: Oligopeptide

<400> SEQUENCE: 23

Gln Arg Ala Asn Thr Ala Phe Thr Pro Phe Leu
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Oligopeptide

<400> SEQUENCE: 24

Cys Pro Gln Arg Ala Gln Arg Met Asn Thr Ala
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Oligopeptide

<400> SEQUENCE: 25

Ala Phe Thr Pro Phe Leu His Gln Arg Asn Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Oligopeptide

<400> SEQUENCE: 26

Cys Pro Gln Arg Ala Gln Arg Met Asn Thr Ala Phe Thr Pro Phe Leu
1               5                   10                  15

<210> SEQ ID NO 27
<211> LENGTH: 11
<212> TYPE: PRT
<213> ORGANISM: Artificial Sequence
<220> FEATURE:
<223> OTHER INFORMATION: Oligopeptide
<220> FEATURE:
<221> NAME/KEY: MOD_RES
<222> LOCATION: (8)..(8)
<223> OTHER INFORMATION: PHOSPHORYLATION OF T
```

```
<400> SEQUENCE: 27

Gln Arg Met Asn Thr Ala Phe Thr Pro Phe Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Oligopeptide

<400> SEQUENCE: 28

Asn Gln Arg Met Asn Thr Ala Phe Thr Pro
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Oligopeptide

<400> SEQUENCE: 29

Ala Ala Arg Met Asn Thr Ala Phe Thr Pro
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Oligopeptide

<400> SEQUENCE: 30

Ala Gln Ala Met Asn Thr Ala Phe Thr Pro
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Oligopeptide

<400> SEQUENCE: 31

Ala Gln Arg Ala Asn Thr Ala Phe Thr Pro
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Oligopeptide

<400> SEQUENCE: 32

Ala Gln Arg Met Ala Thr Ala Phe Thr Pro
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Oligopeptide

<400> SEQUENCE: 33
```

```
Ala Gln Arg Met Asn Ala Ala Phe Thr Pro
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Oligopeptide

<400> SEQUENCE: 34

Ala Gln Arg Met Asn Thr Asn Phe Thr Pro
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Oligopeptide

<400> SEQUENCE: 35

Ala Gln Arg Met Asn Thr Ala Ala Thr Pro
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Oligopeptide

<400> SEQUENCE: 36

Ala Gln Arg Met Asn Thr Ala Phe Ala Pro
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Oligopeptide

<400> SEQUENCE: 37

Ala Gln Arg Met Asn Thr Ala Phe Ala Pro
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Oligopeptide

<400> SEQUENCE: 38

Tyr Gly Arg Lys Lys Arg Arg Gln Arg Arg
1               5                   10

<210> SEQ ID NO 39
<211> LENGTH: 332
<212> TYPE: PRT
<213> ORGANISM: homo sapiens

<400> SEQUENCE: 39

Met Ala Thr Leu Lys Asp Gln Leu Ile Tyr Asn Leu Leu Lys Glu Glu
1               5                   10                  15
```

Gln Thr Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Asp Leu Gly Thr Asp Lys Asp Lys
210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Val Ser Thr Met Ile Lys Gly Leu Tyr Gly Ile Lys Asp Asp Val Phe
        275                 280                 285

Leu Ser Val Pro Cys Ile Leu Gly Gln Asn Gly Ile Ser Asp Leu Val
290                 295                 300

Lys Val Thr Leu Thr Ser Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 40
<211> LENGTH: 334
<212> TYPE: PRT
<213> ORGANISM: homo sapiens

<400> SEQUENCE: 40

Met Ala Thr Leu Lys Glu Lys Leu Ile Ala Pro Val Ala Glu Glu Glu
1               5                   10                  15

Ala Thr Val Pro Asn Asn Lys Ile Thr Val Val Gly Val Gly Gln Val
            20                  25                  30

Gly Met Ala Cys Ala Ile Ser Ile Leu Gly Lys Ser Leu Ala Asp Glu
        35                  40                  45

Leu Ala Leu Val Asp Val Leu Glu Asp Lys Leu Lys Gly Glu Met Met

```
                50                  55                  60
Asp Leu Gln His Gly Ser Leu Phe Leu Gln Thr Pro Lys Ile Val Ala
 65                  70                  75                  80

Asp Lys Asp Tyr Ser Val Thr Ala Asn Ser Lys Ile Val Val Thr
                 85                  90                  95

Ala Gly Val Arg Gln Gln Glu Gly Glu Ser Arg Leu Asn Leu Val Gln
                100                 105                 110

Arg Asn Val Asn Val Phe Lys Phe Ile Ile Pro Gln Ile Val Lys Tyr
                115                 120                 125

Ser Pro Asp Cys Ile Ile Ile Val Val Ser Asn Pro Val Asp Ile Leu
                130                 135                 140

Thr Tyr Val Thr Trp Lys Leu Ser Gly Leu Pro Lys His Arg Val Ile
145                 150                 155                 160

Gly Ser Gly Cys Asn Leu Asp Ser Ala Arg Phe Arg Tyr Leu Met Ala
                165                 170                 175

Glu Lys Leu Gly Ile His Pro Ser Ser Cys His Gly Trp Ile Leu Gly
                180                 185                 190

Glu His Gly Asp Ser Ser Val Ala Val Trp Ser Gly Val Asn Val Ala
                195                 200                 205

Gly Val Ser Leu Gln Glu Leu Asn Pro Glu Met Gly Thr Asp Asn Asp
                210                 215                 220

Ser Glu Asn Trp Lys Glu Val His Lys Met Val Val Glu Ser Ala Tyr
225                 230                 235                 240

Glu Val Ile Lys Leu Lys Gly Tyr Thr Asn Trp Ala Ile Gly Leu Ser
                245                 250                 255

Val Ala Asp Leu Ile Glu Ser Met Leu Lys Asn Leu Ser Arg Ile His
                260                 265                 270

Pro Val Ser Thr Met Val Lys Gly Met Tyr Gly Ile Glu Asn Glu Val
                275                 280                 285

Phe Leu Ser Leu Pro Cys Ile Leu Asn Ala Arg Gly Leu Thr Ser Val
                290                 295                 300

Ile Asn Gln Lys Leu Lys Asp Asp Glu Val Ala Gln Leu Lys Lys Ser
305                 310                 315                 320

Ala Asp Thr Leu Trp Asp Ile Gln Lys Asp Leu Lys Asp Leu
                325                 330

<210> SEQ ID NO 41
<211> LENGTH: 579
<212> TYPE: PRT
<213> ORGANISM: Homo sapiens

<400> SEQUENCE: 41

Met Asn Ala Ile Val Ala Leu Cys His Phe Cys Glu Leu His Gly Pro
 1               5                  10                  15

Arg Thr Leu Phe Cys Thr Glu Val Leu His Ala Pro Leu Pro Gln Gly
                20                  25                  30

Asp Gly Asn Glu Asp Ser Pro Gly Gln Gly Glu Gln Ala Glu Glu Glu
                35                  40                  45

Glu Gly Gly Ile Gln Met Asn Ser Arg Met Arg Ala His Ser Pro Ala
                50                  55                  60

Glu Gly Ala Ser Val Glu Ser Ser Pro Gly Pro Lys Lys Ser Asp
 65                  70                  75                  80

Met Cys Glu Gly Cys Arg Ser Leu Ala Ala Gly His Pro Gly Tyr Ile
                85                  90                  95
```

-continued

```
Ser His Asp Lys Glu Thr Ser Ile Lys Tyr Val Ser His Gln His Pro
                100                 105                 110

Ser His Pro Gln Leu Phe Ser Ile Val Arg Gln Ala Cys Val Arg Ser
        115                 120                 125

Leu Ser Cys Glu Val Cys Pro Gly Arg Glu Gly Pro Ile Phe Phe Gly
    130                 135                 140

Asp Glu Gln His Gly Phe Val Phe Ser His Thr Phe Phe Ile Lys Asp
145                 150                 155                 160

Ser Leu Ala Arg Gly Phe Gln Arg Trp Tyr Ser Ile Ile Thr Ile Met
                165                 170                 175

Met Asp Arg Ile Tyr Leu Ile Asn Ser Trp Pro Phe Leu Leu Gly Lys
        180                 185                 190

Val Arg Gly Ile Ile Asp Glu Leu Gln Gly Lys Ala Leu Lys Val Phe
    195                 200                 205

Glu Ala Glu Gln Phe Gly Cys Pro Gln Arg Ala Gln Arg Met Asn Thr
210                 215                 220

Ala Phe Thr Pro Phe Leu His Gln Arg Asn Gly Asn Ala Ala Arg Ser
225                 230                 235                 240

Leu Thr Ser Leu Thr Ser Asp Asp Asn Leu Trp Ala Cys Leu His Thr
                245                 250                 255

Ser Phe Ala Trp Leu Leu Lys Ala Cys Gly Ser Arg Leu Thr Glu Lys
        260                 265                 270

Leu Leu Glu Gly Ala Pro Thr Glu Asp Thr Leu Val Gln Met Glu Lys
    275                 280                 285

Leu Ala Asp Leu Glu Glu Glu Ser Glu Ser Trp Asp Asn Ser Glu Ala
290                 295                 300

Glu Glu Glu Glu Lys Ala Pro Val Leu Pro Glu Ser Thr Glu Gly Arg
305                 310                 315                 320

Glu Leu Thr Gln Gly Pro Ala Glu Ser Ser Leu Ser Gly Cys Gly
                325                 330                 335

Ser Trp Gln Pro Arg Lys Leu Pro Val Phe Lys Ser Leu Arg His Met
        340                 345                 350

Arg Gln Val Leu Gly Ala Pro Ser Phe Arg Met Leu Ala Trp His Val
    355                 360                 365

Leu Met Gly Asn Gln Val Ile Trp Lys Ser Arg Asp Val Asp Leu Val
370                 375                 380

Gln Ser Ala Phe Glu Val Leu Arg Thr Met Leu Pro Val Gly Cys Val
385                 390                 395                 400

Arg Ile Ile Pro Tyr Ser Ser Gln Tyr Glu Glu Ala Tyr Arg Cys Asn
                405                 410                 415

Phe Leu Gly Leu Ser Pro His Val Gln Ile Pro Pro His Val Leu Ser
        420                 425                 430

Ser Glu Phe Ala Val Ile Val Glu Val His Ala Ala Ala Arg Ser Thr
    435                 440                 445

Leu His Pro Val Gly Cys Glu Asp Asp Gln Ser Leu Ser Lys Tyr Glu
450                 455                 460

Phe Val Val Thr Ser Gly Ser Pro Val Ala Ala Asp Arg Val Gly Pro
465                 470                 475                 480

Thr Ile Leu Asn Lys Ile Glu Ala Ala Leu Thr Asn Gln Asn Leu Ser
                485                 490                 495

Val Asp Val Val Asp Gln Cys Leu Val Cys Leu Lys Glu Glu Trp Met
        500                 505                 510

Asn Lys Val Lys Val Leu Phe Lys Phe Thr Lys Val Asp Ser Arg Pro
```

```
                515                 520                 525
Lys Glu Asp Thr Gln Lys Leu Leu Ser Ile Leu Gly Ala Ser Glu Glu
        530                 535                 540

Asp Asn Val Lys Leu Leu Lys Phe Trp Met Thr Gly Leu Ser Lys Thr
545                 550                 555                 560

Tyr Lys Ser His Leu Met Ser Thr Val Arg Ser Pro Thr Ala Ser Glu
                565                 570                 575

Ser Arg Asn
```